United States Patent
Hong et al.

(10) Patent No.: US 11,653,562 B2
(45) Date of Patent: May 16, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD, Chungcheongnam-do (KR)

(72) Inventors: Jin-Ri Hong, Gyeonggi-do (KR); Doo-Hyeon Moon, Gyeonggi-do (KR); Du-Yong Park, Gyeonggi-do (KR); Young-Mook Lim, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

(21) Appl. No.: 17/267,469

(22) PCT Filed: Aug. 7, 2019

(86) PCT No.: PCT/KR2019/009877
§ 371 (c)(1),
(2) Date: Feb. 9, 2021

(87) PCT Pub. No.: WO2020/032574
PCT Pub. Date: Feb. 13, 2020

(65) Prior Publication Data
US 2021/0320252 A1    Oct. 14, 2021

(30) Foreign Application Priority Data
Aug. 10, 2018  (KR) .................. 10-2018-0093813
Aug. 1, 2019   (KR) .................. 10-2019-0093605

(51) Int. Cl.
*H01L 51/00* (2006.01)
*C07C 211/61* (2006.01)
*C09K 11/06* (2006.01)

(52) U.S. Cl.
CPC .......... *H10K 85/633* (2023.02); *C07C 211/61* (2013.01); *C09K 11/06* (2013.01); *C09K 2211/1014* (2013.01); *H10K 50/15* (2023.02); *H10K 85/626* (2023.02)

(58) Field of Classification Search
CPC .............. H01L 51/006; H01L 51/0058; H01L 51/5056; C09K 11/06; C09K 2211/1014; C07C 211/61
See application file for complete search history.

(56) References Cited

U.S. PATENT DOCUMENTS

| | | | |
|---|---|---|---|
| 2015/0318487 A1* | 11/2015 | Ito | H01L 51/5076 257/40 |
| 2015/0318510 A1* | 11/2015 | Ito | H01L 51/5072 257/40 |
| 2015/0318511 A1 | 11/2015 | Kim et al. | |
| 2016/0111663 A1* | 4/2016 | Kim | H01L 51/006 257/40 |
| 2016/0254450 A1 | 9/2016 | Herron et al. | |
| 2018/0182972 A1* | 6/2018 | So | C07D 209/88 |
| 2018/0282299 A1 | 10/2018 | Dogra et al. | |
| 2019/0055187 A1* | 2/2019 | Kim | C09K 11/06 |
| 2021/0328150 A1* | 10/2021 | Park | H01L 51/0061 |

FOREIGN PATENT DOCUMENTS

| | | | | |
|---|---|---|---|---|
| CN | 107805242 A | * | 3/2018 | |
| CN | 107814774 A | * | 3/2018 | |
| CN | 107827809 A | * | 3/2018 | |
| CN | 108795419 A | * | 11/2018 | |
| KR | 20180027195 A | | 3/2018 | |
| KR | 10-2017-0105081 | * | 8/2018 | |
| KR | 20190007789 A | * | 1/2019 | |
| KR | 20190007789 A | | 1/2019 | |
| WO | 2015084114 A1 | | 6/2015 | |
| WO | WO-2016200070 A2 | * | 12/2016 | C07C 211/60 |

OTHER PUBLICATIONS

CAS Abstract and Indexed Compounds H. So et al., US 20180182972 (2018) (Year: 2018).*
CAS Abstract and Indexed Compounds J. Kim et al., US 2019/0055187 (2019) (Year: 2019).*
Email communication to CAS Customer Center, Subject: "My reference 17-267,469, Assistance in locating RN 2052967-07-2 within US 20160351817" (Transmitted Apr. 5, 2022) (Year: 2022).*
CAS Abstract RN 2052967-07-2 (Dec. 21, 2016) (Year: 2016).*
CAS Abstract S. Kim et al., US 20160351817 (2016) (Year: 2016).*
CAS Abstract of X. Dong et al., CN 107827809 (Mar. 23, 2018). (Year: 2018).*

* cited by examiner

Primary Examiner — Alexander R Pagano
(74) Attorney, Agent, or Firm — G. Creston Campbell

(57) ABSTRACT

The present disclosure relates to an organic electroluminescent compound represented by formula 1 and an organic electroluminescent device comprising the same. By comprising the organic electroluminescent compound of the present disclosure, an organic electroluminescent device having improved driving voltage, luminous efficiency, and/or lifespan characteristics can be provided.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules, and aluminum complexes as materials for forming a light-emitting layer [Appl. Phys. Lett. 51, 913, 1987].

In order to enhance the efficiency and stability of an organic EL device, it has a structure of a multilayer comprising a hole injection layer, a hole transport layer, a light-emitting layer, an electron transport layer, and an electron injection layer. The selection of a compound comprised in the hole transport layer, etc., is known as one of the methods for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4''-tris(3-methylphenylphenylamino)triphenylamine (MTDATA), etc., were used as a hole injection and transport material in an organic EL device. However, an organic EL device using these materials is problematic in quantum efficiency and lifespan. It is because, when an organic EL device is driven under high current, thermal stress occurs between an anode and the hole injection layer. Thermal stress significantly reduces the lifespan of the device. Further, since the organic material used in the hole injection layer has very high hole mobility, the hole-electron charge balance may be broken and quantum yield (cd/A) may decrease.

Therefore, a hole transport material for improving performance of an organic EL device still needs to be developed.

Korean Patent Application Laying-Open No. 10-2015-0066202 discloses an organic electroluminescent compound in which a diarylamino is bonded to a benzofluorene structure. However, this compound is not sufficiently satisfactory to be used in a hole transport zone.

DISCLOSURE OF INVENTION

Technical Problem

The objective of the present disclosure is first to provide an organic electroluminescent compound which is efficient for producing an organic electroluminescent device having improved driving voltage, luminous efficiency, and/or lifespan characteristics, and second to provide an organic electroluminescent device comprising the organic electroluminescent compound.

Solution to Problem

The present inventors found that the above objective can be achieved by an organic electroluminescent compound represented by the following formula 1:

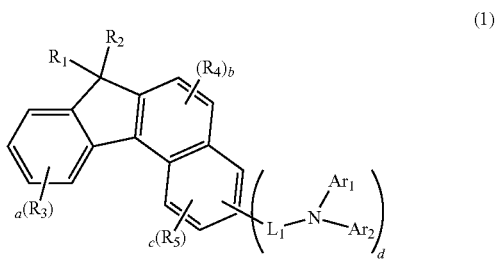

(1)

wherein $Ar_1$ and $Ar_2$ each independently represent hydrogen, deuterium, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, where if a plurality of $Ar_1$ or $Ar_2$ is present, each of $Ar_1$ or each of $Ar_2$ may be the same or different;

where if $Ar_1$ and $Ar_2$ each independently represent a substituted or unsubstituted (C6-C30)aryl, or a substituted or unsubstituted (3- to 30-membered)heteroaryl, $Ar_1$ and $Ar_2$ may be linked to each other via a single bond to form a ring(s);

$L_1$ represents a single bond, a substituted or unsubstituted (C6-C30)arylene, or a substituted or unsubstituted (3- to 30-membered)heteroarylene, where if a plurality of $L_1$ is present, each of $L_1$ may be the same or different;

$R_1$ and $R_2$ each independently represent a substituted or unsubstituted (C1-C30)alkyl, a substituted or unsubstituted (C6-C30)aryl, or a substituted or unsubstituted (3-to 30-membered)heteroaryl;

$R_3$ to $R_5$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, where if a plurality of $R_3$ to $R_5$ is present, each of $R_3$, each of $R_4$, and each of $R_5$ may be the same or different; and a represents an integer of 1 to 4, b represents 1 or 2, c represents an integer of 1 to 3, d represents 1 or 2, and c+d is 4, where if a, b, c, and d each independently are 2 or more, each of $R_3$, each of $R_4$, each of $R_5$, and each of $-L_1-NAr_1Ar_2$ may be the same or different.

Advantageous Effects of Invention

By using the organic electroluminescent compound of the present disclosure, an organic electroluminescent device having improved driving voltage, luminous efficiency, and/or lifespan characteristics can be provided.

MODE FOR THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in at least one layer constituting a hole transport zone, but is not limited thereto. When the compound of formula 1 is comprised in a hole transport layer, a hole auxiliary layer, or a light-emitting auxiliary layer, it may be comprised as a hole transport material, a hole auxiliary material, or a light-emitting auxiliary material. In addition, the compound represented by formula 1 may be comprised in a light-emitting layer, but is not limited thereto. When the compound of formula 1 is comprised in a light-emitting layer, it may be comprised as a host.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, includes a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. More specifically, the above aryl(ene) may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4''-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, and a 9,9-diphenyl-4-fluorenyl group. "(3- to 30-membered)heteroaryl(ene)" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); includes a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. More specifically, the above hereroaryl(ene) may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, an azacarbazolyl-8-yl group, an azacarbazolyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. "Halogen" includes F, Cl, Br, and I.

In addition, "ortho," "meta," and "para" signify substitution positions of two substituents. The ortho position represents a just neighboring position, and, for example, in the case of benzene, represents 1,2 positions. The meta position represents the position next to the just neighboring position, and, for example, in the case of benzene, represents 1,3 positions. The para position represents the position next to the meta position, and, for example, in the case of benzene, represents 1,4 positions.

Herein, "substituted" in the expression "substituted or unsubstituted" means that a hydrogen atom in a certain functional group is replaced with another atom or functional group, i.e., a substituent. The substituents of the substituted alkyl, the substituted aryl(ene), the substituted heteroaryl (ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino in $Ar_1$, $Ar_2$, $L_1$, and $R_1$ to $R_5$ in formula 1 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl(s), a (C6-C30)aryl unsubstituted or substituted with a (3- to 30-membered) heteroaryl(s), a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino unsubstituted or substituted with a (C1-C30)alkyl(s), a (C1-C30)alkyl(C6-C30) arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl; and preferably each independently are at least one of (C1-C6)alkyl and a (C6-C20)aryl. Specifically, the substituent may be at least one of methyl, phenyl, and naphthyl.

Formula 1 may be represented by any one of the following formulas 2 to 7:

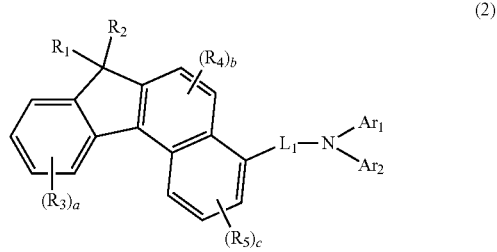

(2)

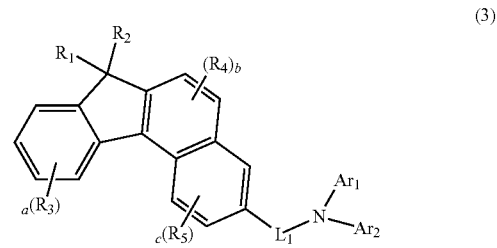

(3)

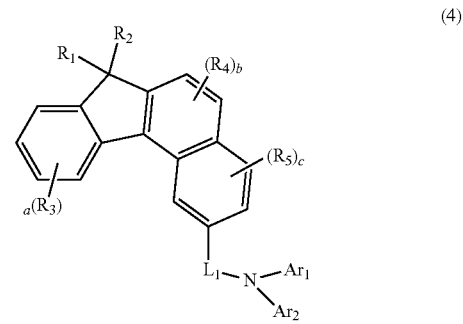

(4)

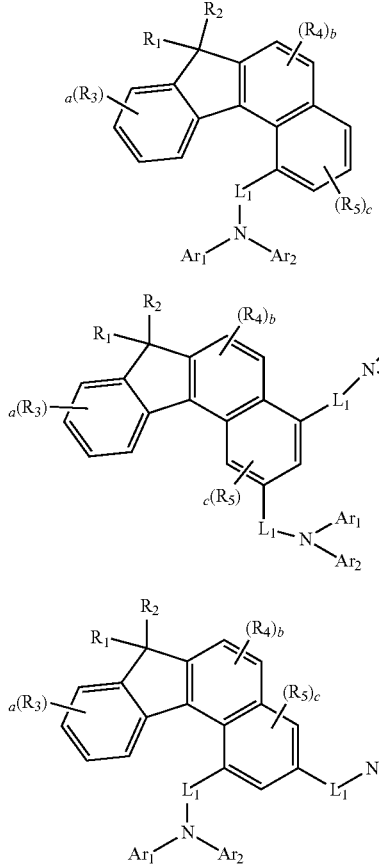

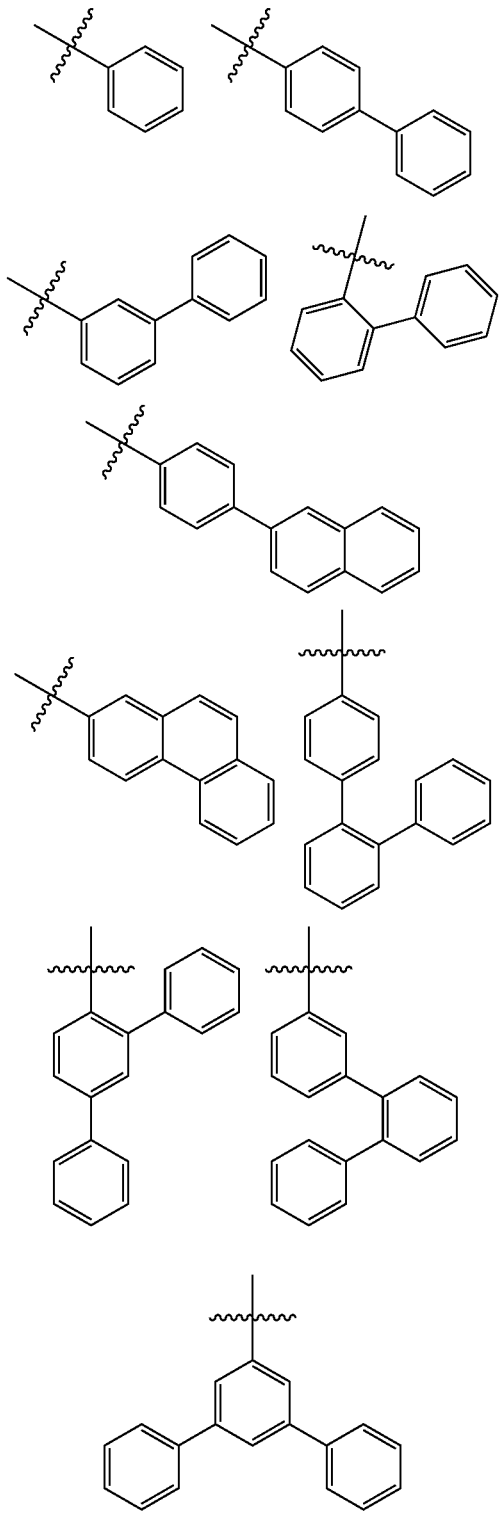

wherein $Ar_1$, $Ar_2$, $L_1$, $R_1$ to $R_5$, and a to c are as defined in formula 1, and in formulas 6 and 7, each of $L_1$, each of $Ar_1$, and each of $Ar_2$ may be the same or different.

In formula 1 above, $Ar_1$ and $Ar_2$ each independently represent hydrogen, deuterium, a substituted or unsubstituted (C1-C30)alkyl, a substituted or unsubstituted (C6-C30)aryl, a substituted or unsubstituted (3- to 30-membered) heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, where if a plurality of $Ar_1$ or $Ar_2$ is present, each of $Ar_1$ or each of $Ar_2$ may be the same or different. According to one embodiment of the present disclosure, $Ar_1$ and $Ar_2$ each independently represent a substituted or unsubstituted (C6-C30)aryl, or a substituted or unsubstituted (5- to 20-membered)heteroaryl, and $Ar_1$ and $Ar_2$ may be linked to each other via a single bond to form a ring(s). According to another embodiment of the present disclosure, $Ar_1$ and $Ar_2$ each independently represent a (C6-C30)aryl unsubstituted or substituted with one or more of a (C1-C6)alkyl(s) and a (C6-C12)aryl(s), or a (5- to 20-membered)heteroaryl unsubstituted or substituted with a (C6-C12)aryl(s), and $Ar_1$ and $Ar_2$ may be linked to each other via a single bond to form a ring(s). Specifically, $Ar_1$ and $Ar_2$ may each independently represent a phenyl, a biphenyl, a naphthylphenyl, a terphenyl, a dimethylfluorenyl, a diphenylfluorenyl, a spirobifluorenyl, a dimethylbenzofluorenyl, a dibenzofuranyl, a dibenzothiophenyl, a benzonaphthofuranyl, a phenylcarbazolyl, a naphthylcarbazolyl, etc., or $Ar_1$ and $Ar_2$ are both a phenyl and are linked to each other via a single bond to form a carbazole ring.

$Ar_1$ and $Ar_2$ each independently may be selected from the following structures, where if a plurality of $Ar_1$ or $Ar_2$ is present, each of $Ar_1$ or each of $Ar_2$ may be the same or different.

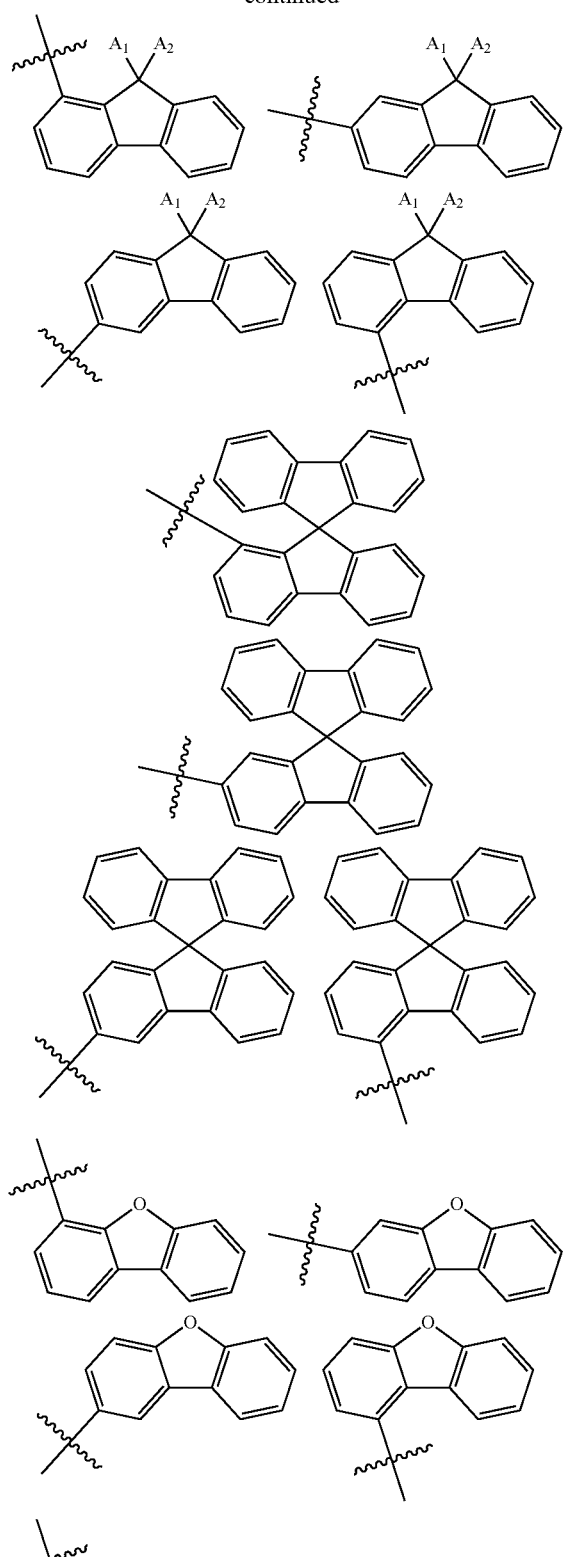
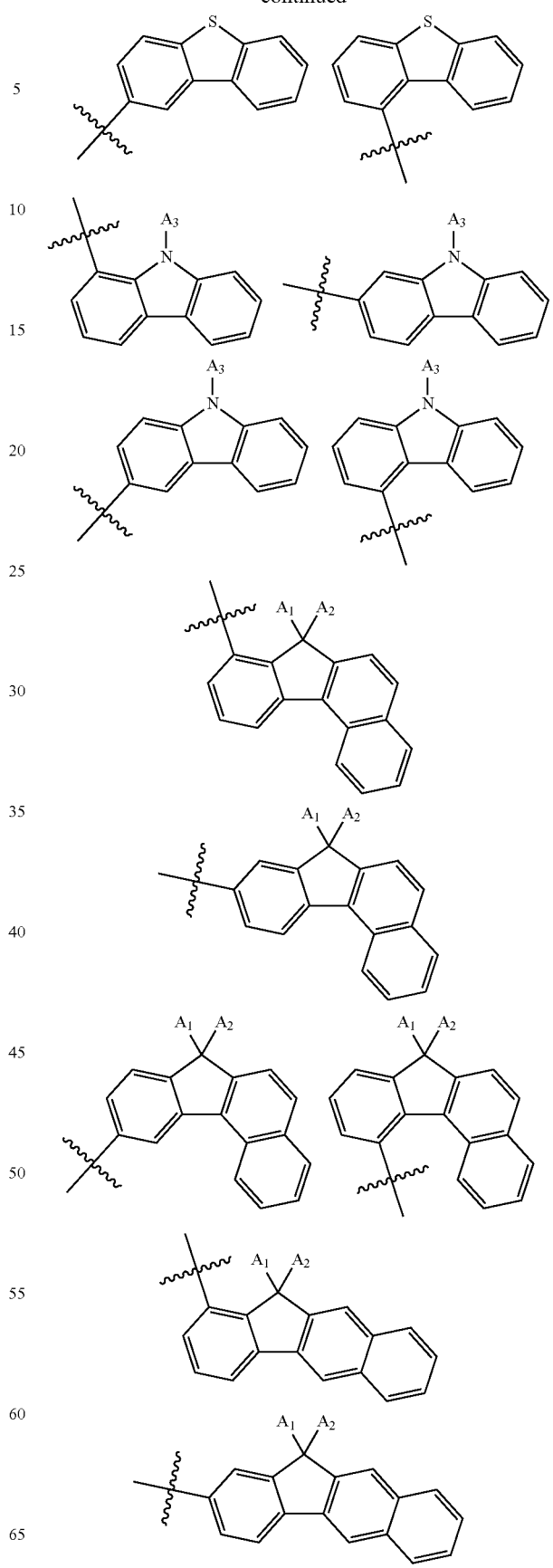

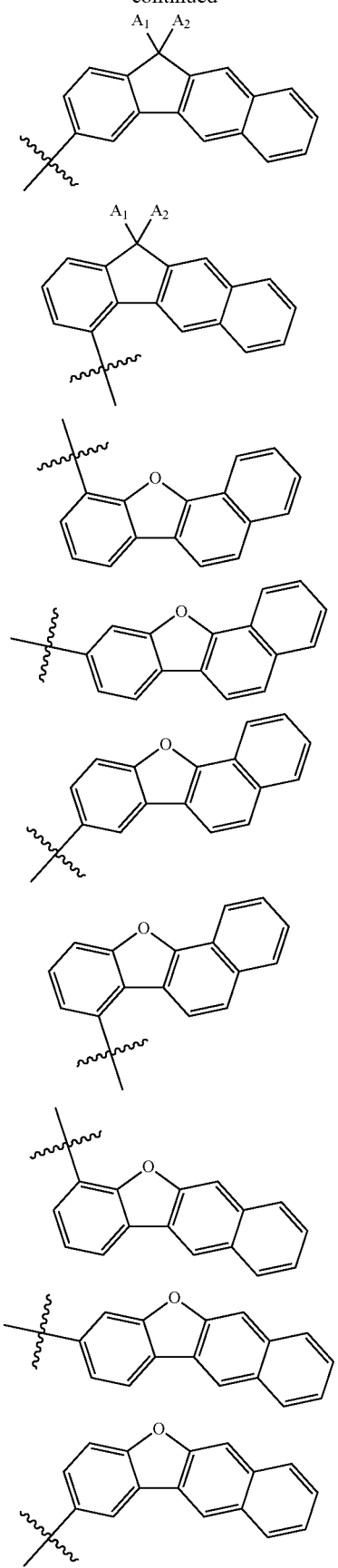

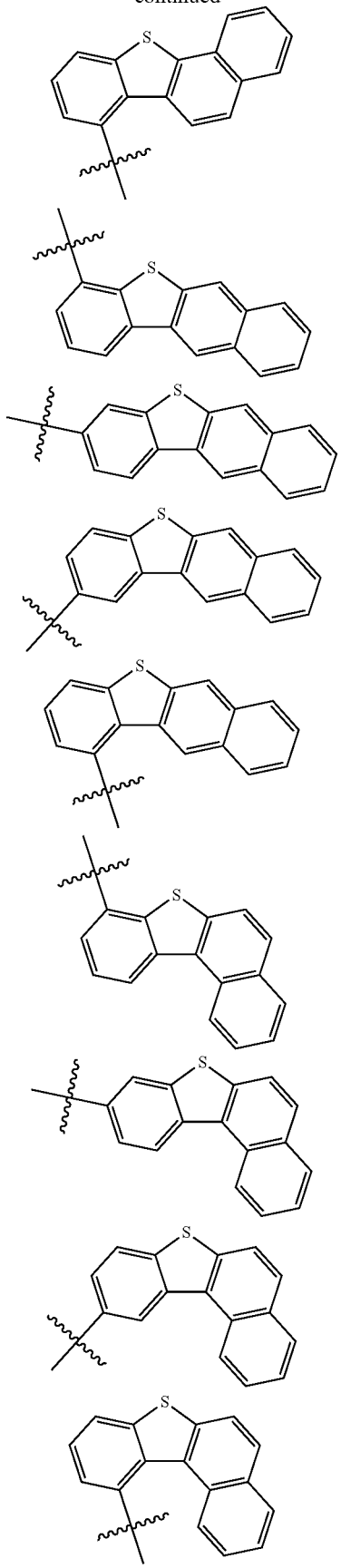
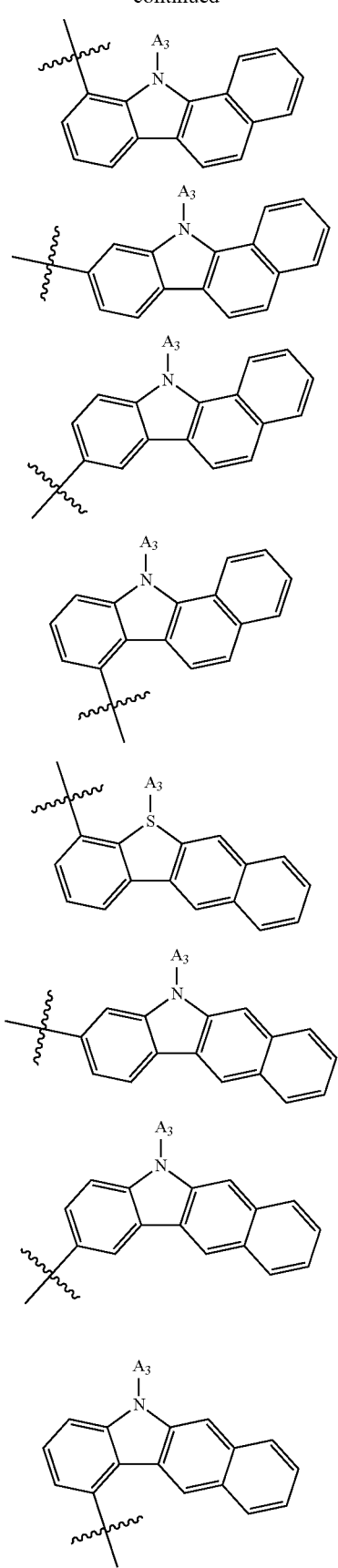

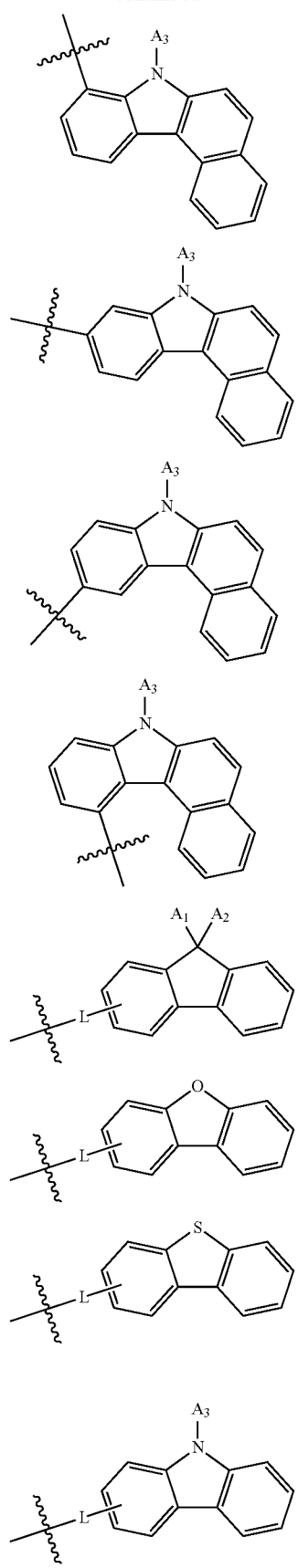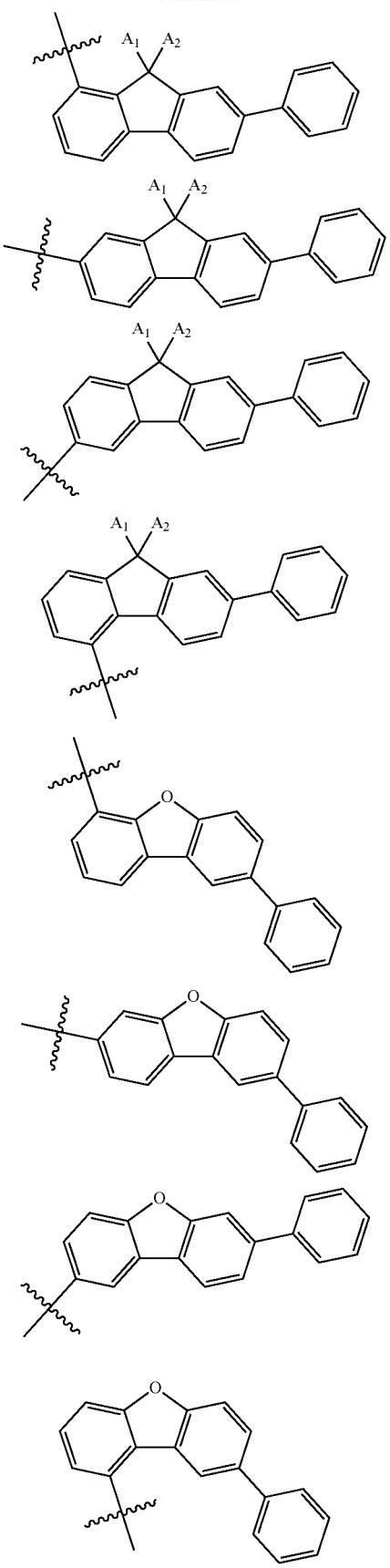

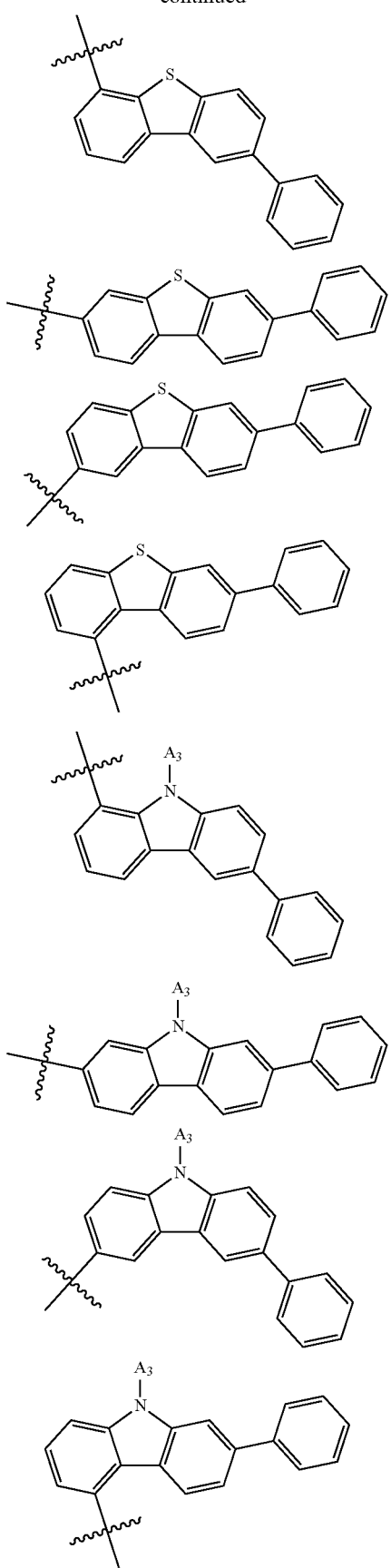

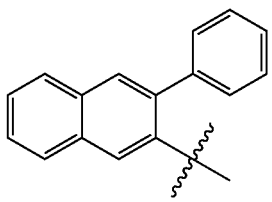

wherein

A₁ to A₃ each independently represent a substituted or unsubstituted (C1-C30)alkyl, a substituted or unsubstituted (C6-C30)aryl, or a substituted or unsubstituted (3- to 30-membered)heteroaryl; and L represents a substituted or unsubstituted (C6-C30) arylene, or a substituted or unsubstituted (3- to 30-membered)heteroarylene.

$L_1$ represents a single bond, a substituted or unsubstituted (C6-C30)arylene, or a substituted or unsubstituted (3- to 30-membered)heteroarylene, where if a plurality of $L_1$ is present, each of $L_1$ may be the same or different. According to one embodiment of the present disclosure, $L_1$ represents a single bond, a substituted or unsubstituted (C6-C12) arylene, or a substituted or unsubstituted (5- to 15-membered)heteroarylene. According to another embodiment of the present disclosure, $L_1$ represents a single bond, an unsubstituted (C6-C12)arylene, or an unsubstituted (5- to 15-membered)heteroarylene. Specifically, $L_1$ represents a single bond, a phenylene, a carbazolylene, etc.

$R_1$ and $R_2$ each independently represent a substituted or unsubstituted (C1-C30)alkyl, a substituted or unsubstituted (C6-C30)aryl, or a substituted or unsubstituted (3- to 30-membered)heteroaryl. According to one embodiment of the present disclosure, $R_1$ and $R_2$ each independently represent a substituted or unsubstituted (C1-C6)alkyl, or a substituted or unsubstituted (C6-C12)aryl. According to another embodiment of the present disclosure, $R_1$ and $R_2$ each independently represent an unsubstituted (C1-C6)alkyl, or an unsubstituted (C6-C12)aryl. Specifically, $R_1$ and $R_2$ may each independently represent a methyl, a phenyl, etc.

$R_3$ to $R_5$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, where if a plurality of $R_3$ to $R_5$ is present, each of $R_3$, each of $R_4$, and each of $R_5$ may be the same or different. According to one embodiment of the present disclosure, $R_3$ to $R_5$ each independently represent hydrogen, or a substituted or unsubstituted (C6-C12)aryl. According to another embodiment of the present disclosure, $R_3$ to $R_5$ each independently represent hydrogen, or an unsubstituted (C6-C12)aryl. Specifically, $R_3$ to $R_5$ may each independently represent hydrogen, a phenyl, etc.

According to one embodiment of the present disclosure, in formula 1 above, $Ar_1$ and $Ar_2$ each independently represent a substituted or unsubstituted (C6-C30)aryl, or a substituted or unsubstituted (5- to 20-membered)heteroaryl, in which $Ar_1$ and $Ar_2$ may be linked to each other via a single bond to form a ring(s); $L_1$ represents a single bond, a substituted or unsubstituted (C6-C12)arylene, or a substituted or unsubstituted (5- to 15-membered)heteroarylene; $R_1$ and $R_2$ each independently represent a substituted or unsubstituted (C1-C6)alkyl, or a substituted or unsubstituted (C6-C12)aryl; and $R_3$ to $R_5$ each independently represent hydrogen, or a substituted or unsubstituted (C6-C12)aryl.

According to another embodiment of the present disclosure, in formula 1 above, $Ar_1$ and $Ar_2$ each independently represent a (C6-C30)aryl unsubstituted or substituted with one or more of a (C1-C6)alkyl(s) and a (C6-C12)aryl(s), or a (5- to 20-membered)heteroaryl unsubstituted or substituted with a (C6-C12)aryl(s), in which $Ar_1$ and $Ar_2$ may be linked to each other via a single bond to form a ring(s); $L_1$ represents a single bond, an unsubstituted (C6-C12)arylene, or an unsubstituted (5- to 15-membered)heteroarylene; $R_1$ and $R_2$ each independently represent an unsubstituted (C1-C6)alkyl, or an unsubstituted (C6-C12)aryl; and $R_3$ to $R_5$ each independently represent hydrogen, or an unsubstituted (C6-C12)aryl.

In the formulas of the present disclosure, if a substituent is linked to an adjacent substituent to form a ring, the ring, which is formed by linkages of at least two adjacent substituents, may be a substituted or unsubstituted, mono- or polycyclic, alicyclic or aromatic (3- to 30-membered) ring, or the combination thereof, in which the formed ring may contain at least one heteroatom selected from nitrogen, oxygen, and sulfur. For example, the fused ring may be a substituted or unsubstituted dibenzothiophene ring, a substituted or unsubstituted dibenzofurane ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl(ene) may each independently contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C8-C30)arylamino.

The compound represented by formula 1 includes the following compounds, but is not limited thereto.

C-1
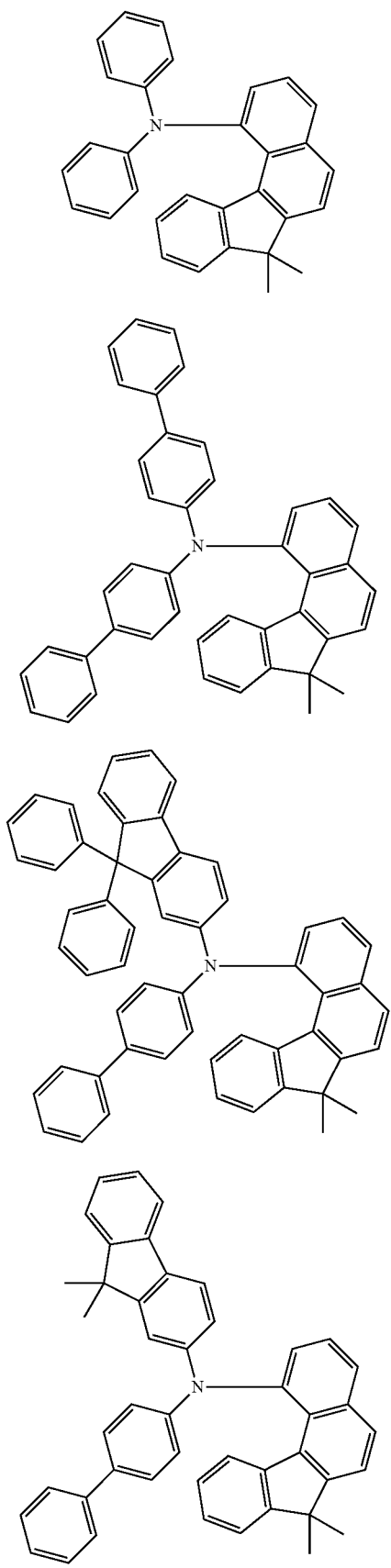
C-2
C-3
C-4
C-5
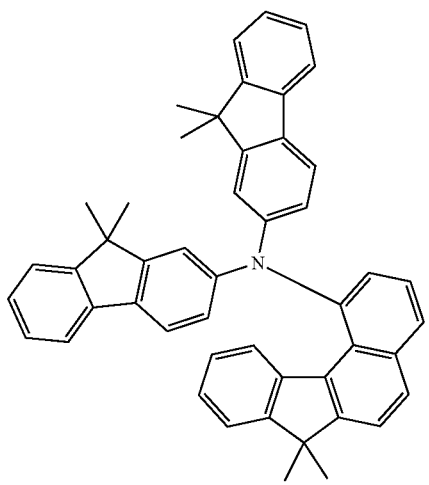
C-6
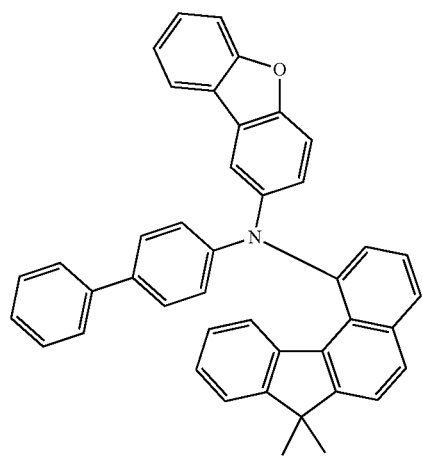
C-7
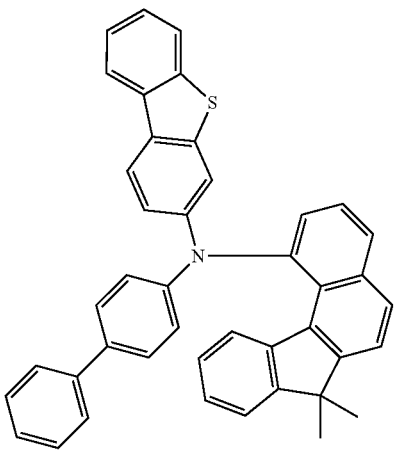

C-8
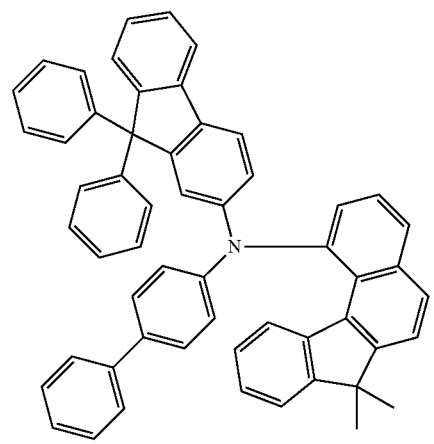
C-9
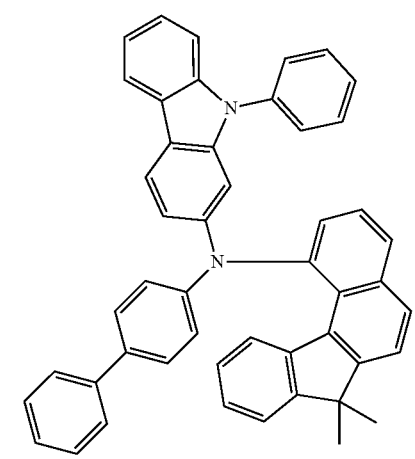
C-10
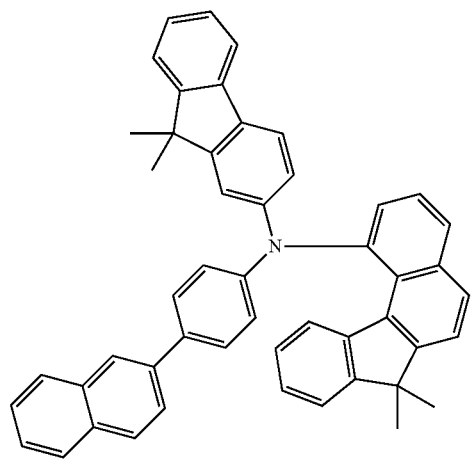
C-11
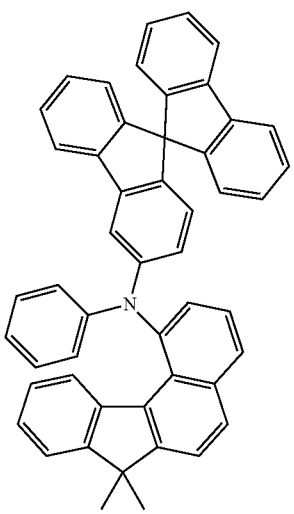
C-12
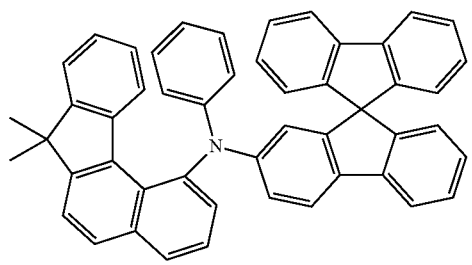
C-13
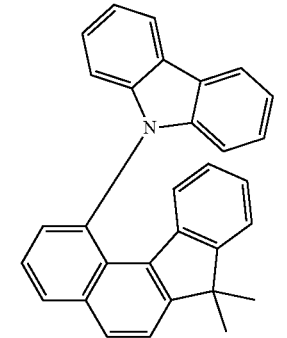
C-14
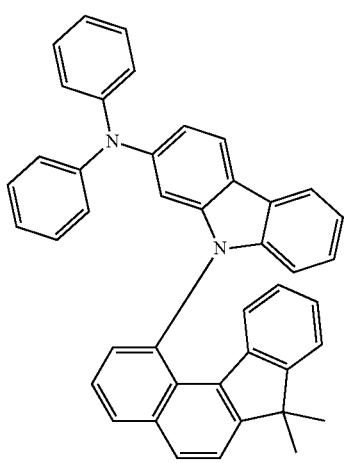

C-15
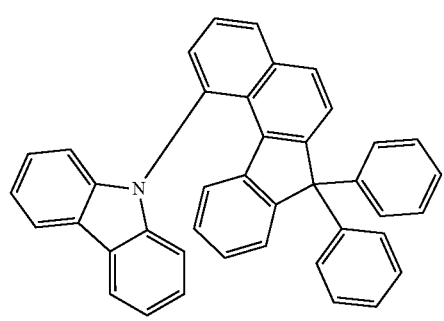
C-16
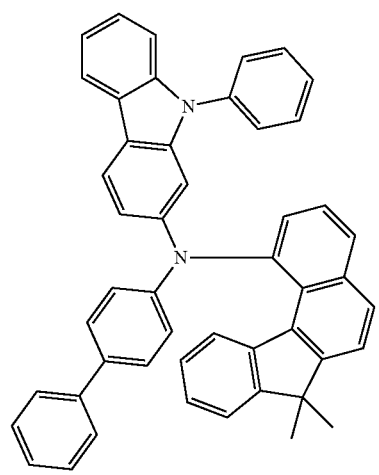
C-17
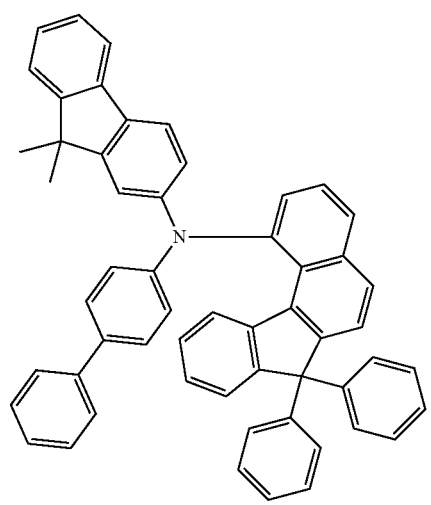
C-18
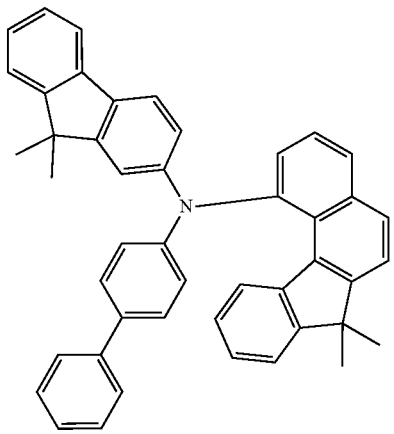
C-19
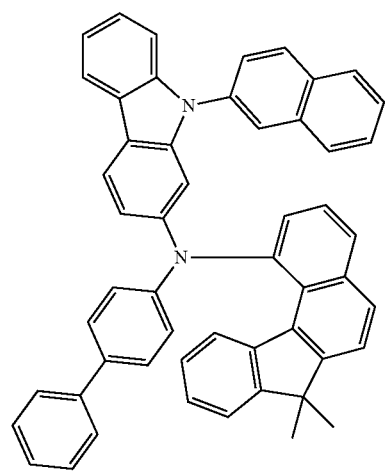
C-20
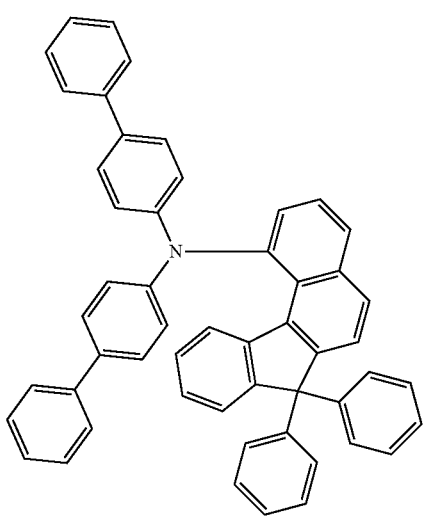

C-21
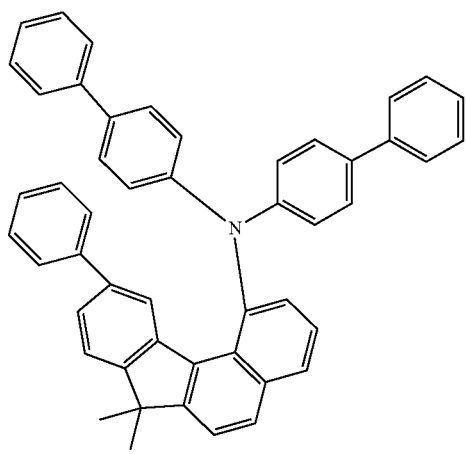
C-22
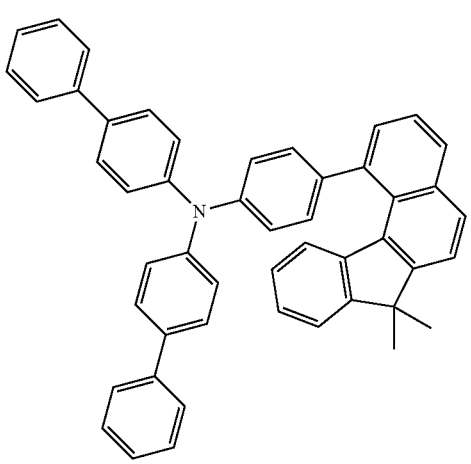
C-23
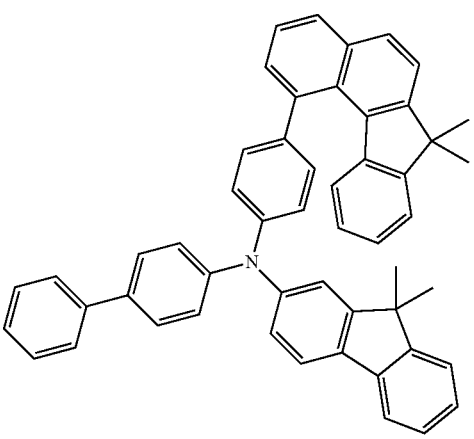
C-24
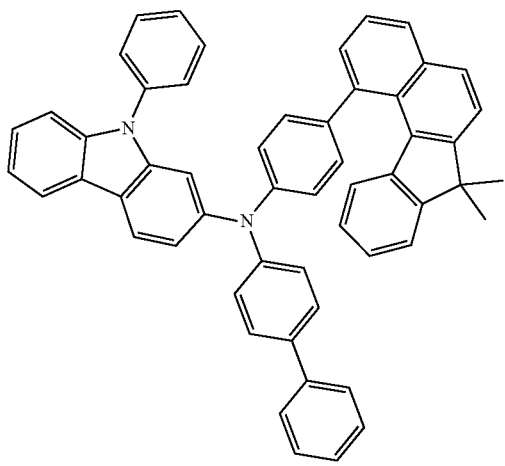
C-25
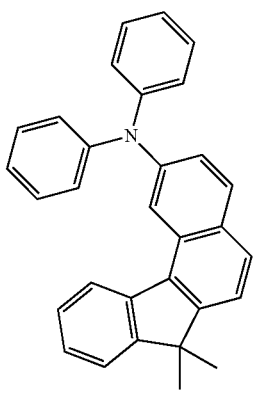
C-26
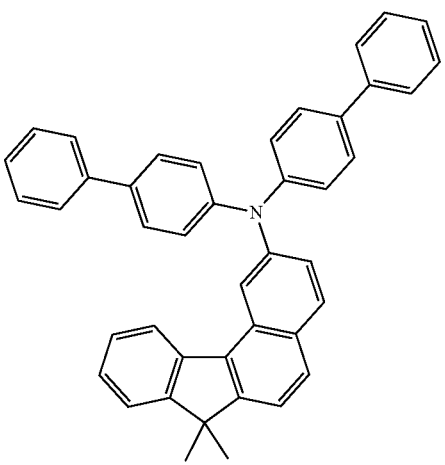

C-27
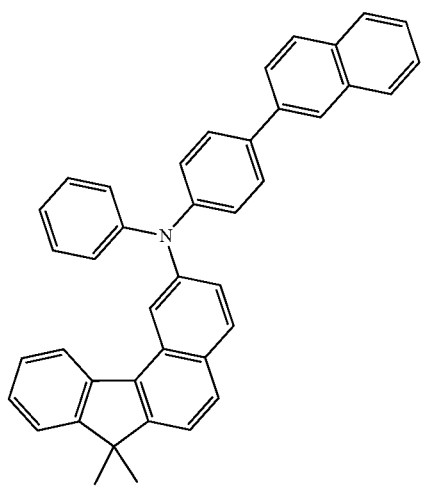
C-30
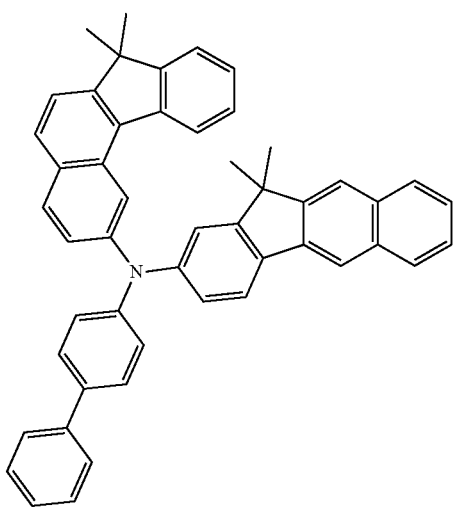
C-28
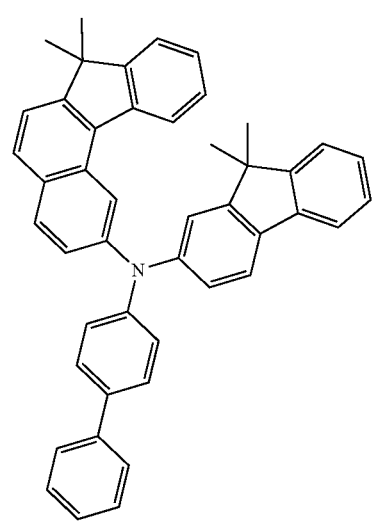
C-31
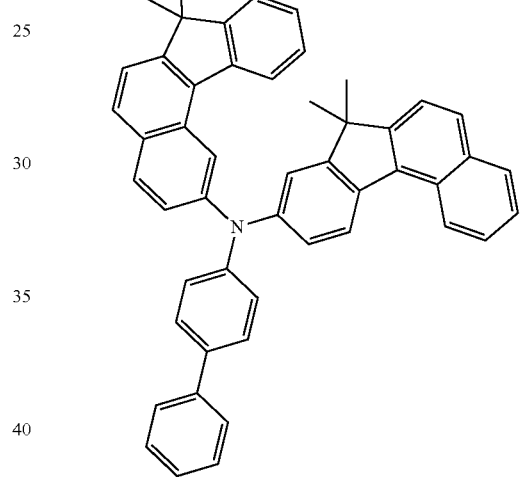
C-29
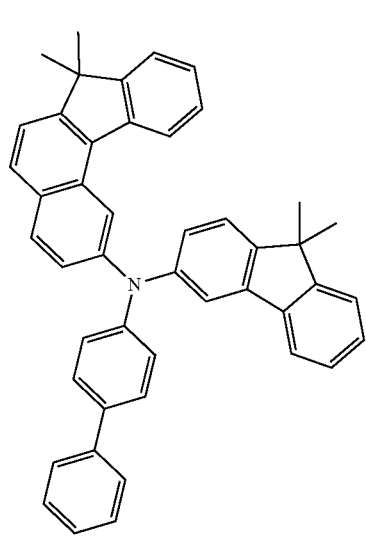
C-32
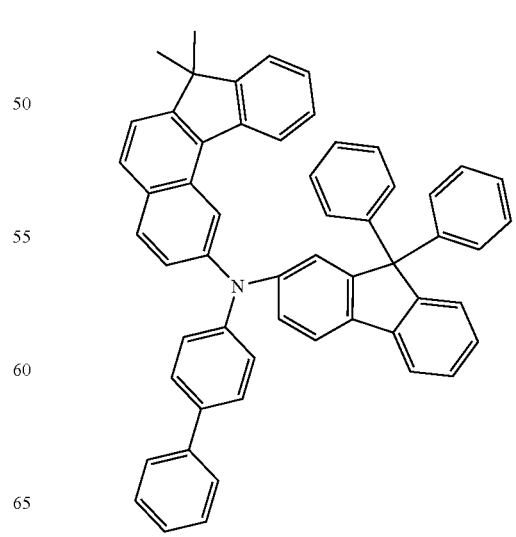

C-33
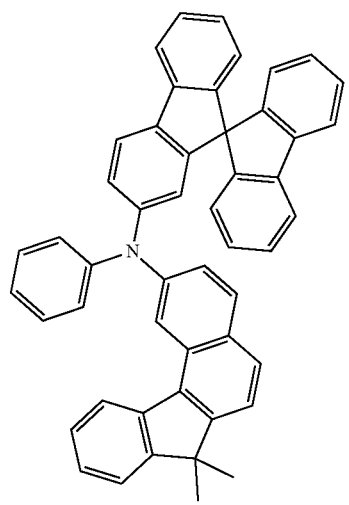
C-34
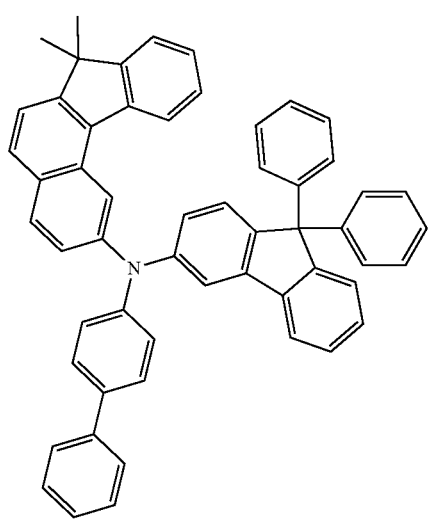
C-36
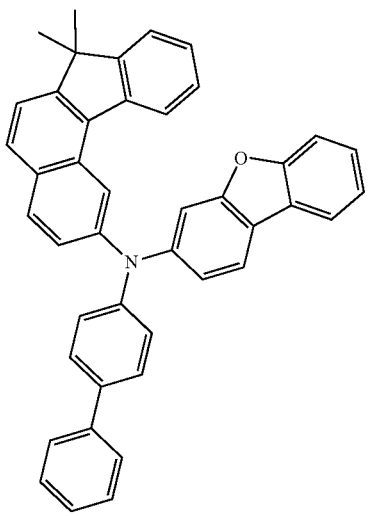
C-37
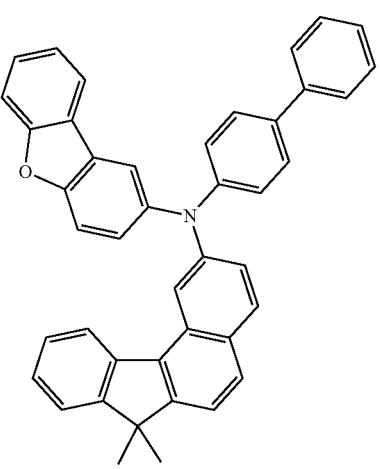
C-35
C-38
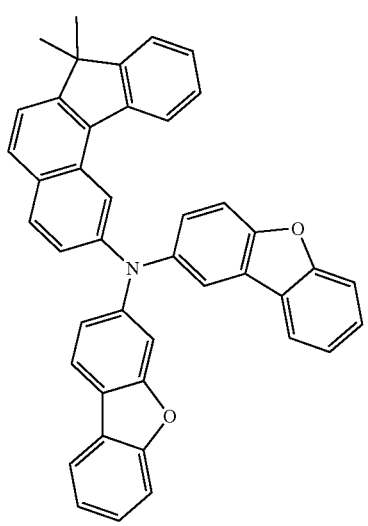

C-39
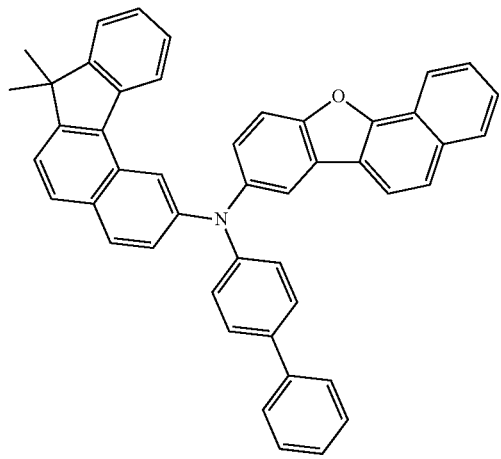
C-40
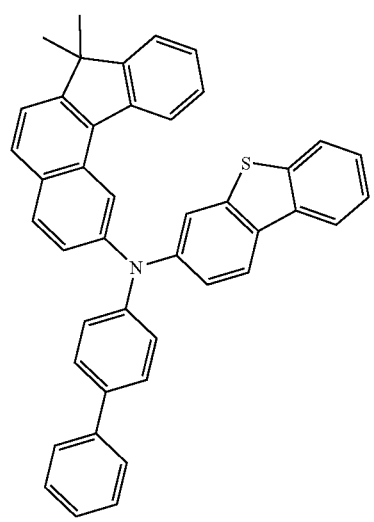
C-41
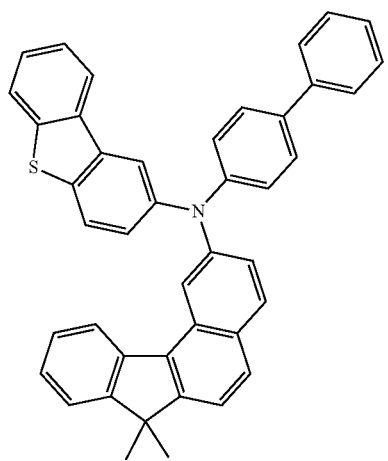
C-42
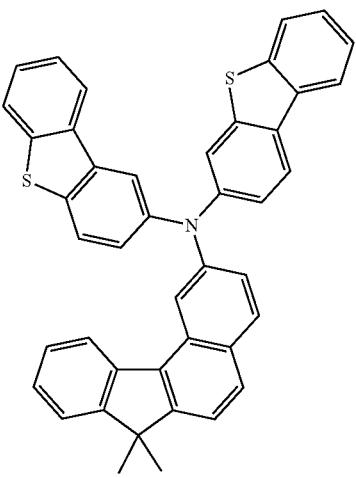
C-43
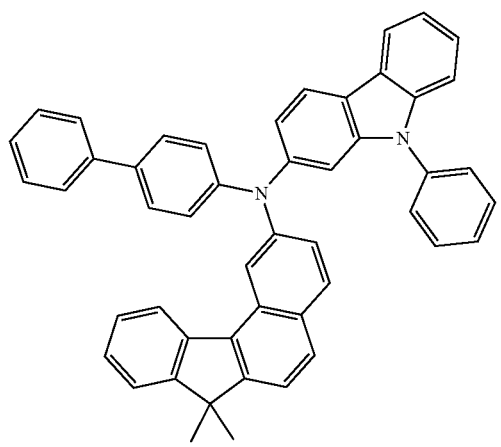
C-44
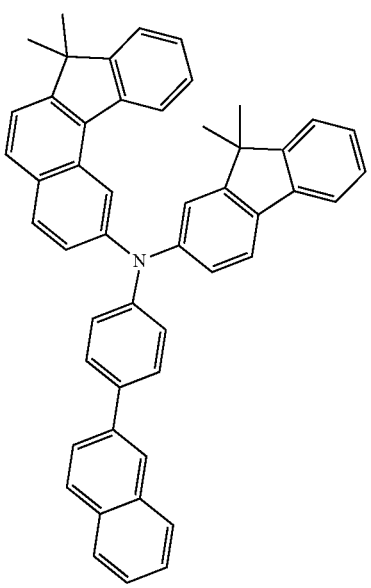

C-45
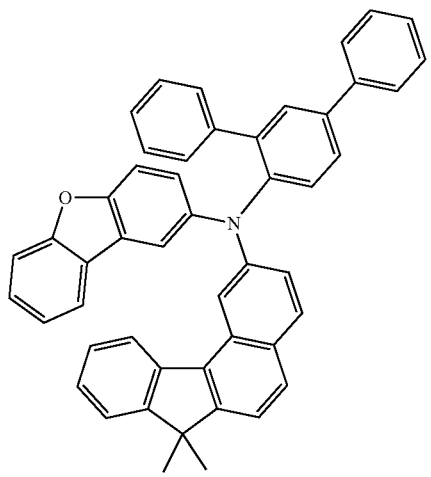
C-46
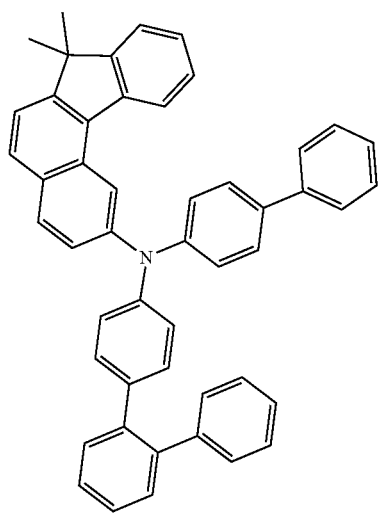
C-47
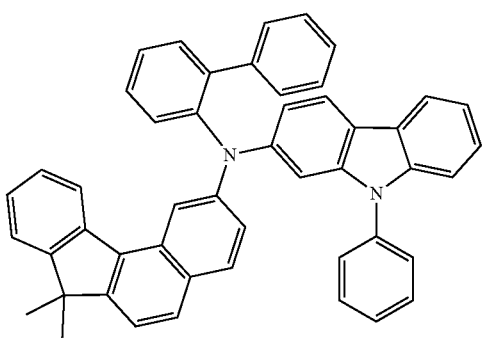
C-48
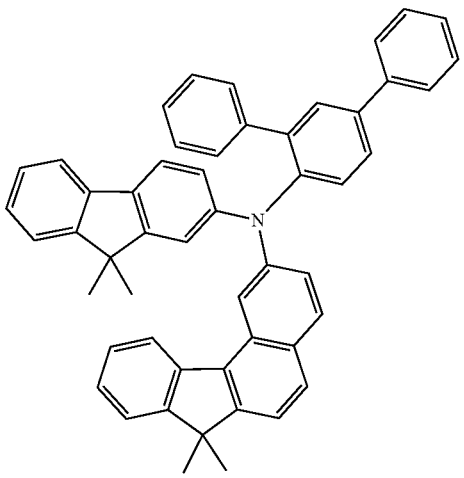
C-49
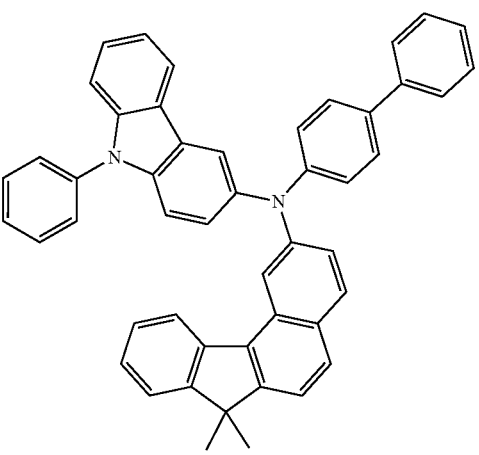
C-50
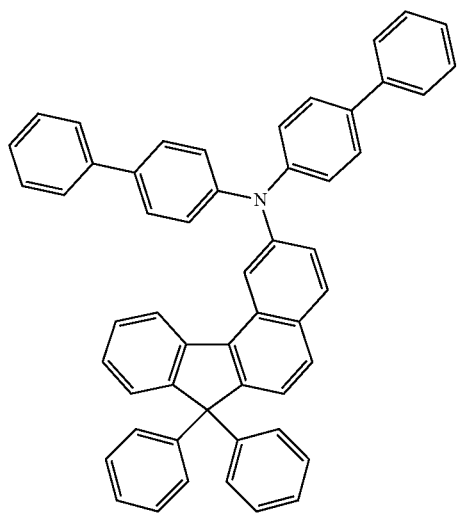

C-51
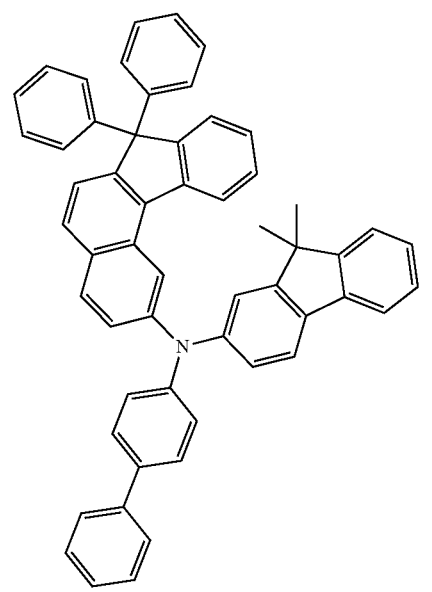
C-52
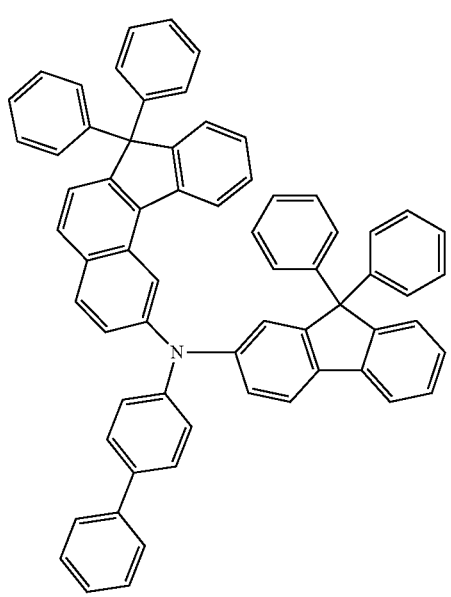
C-53
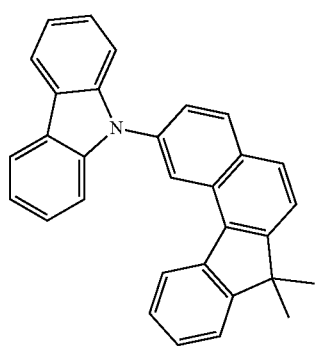
C-54
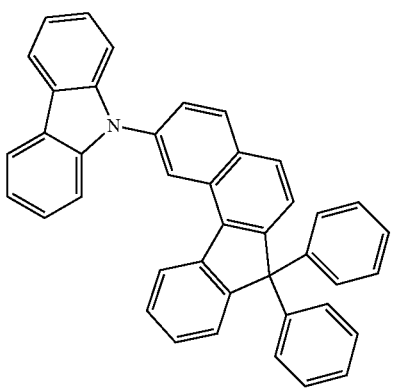
C-55
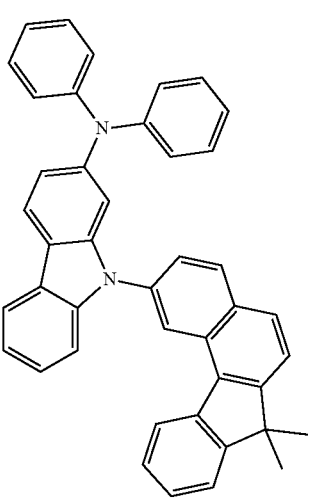
C-56
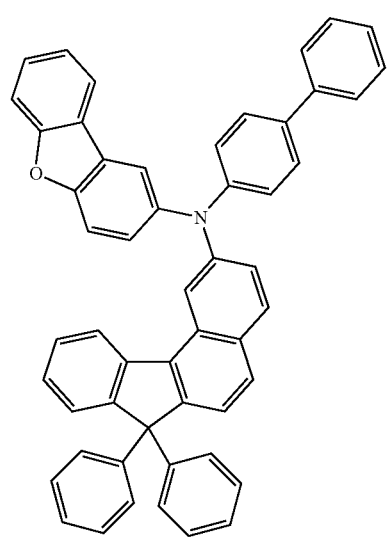

C-57
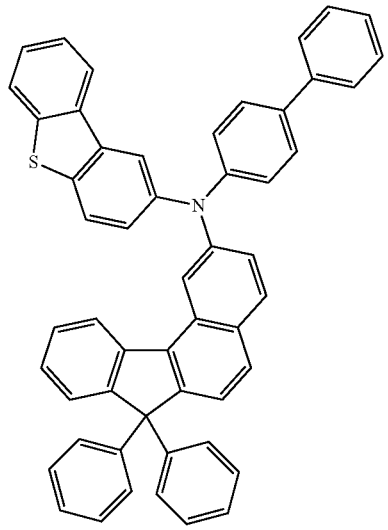
C-58
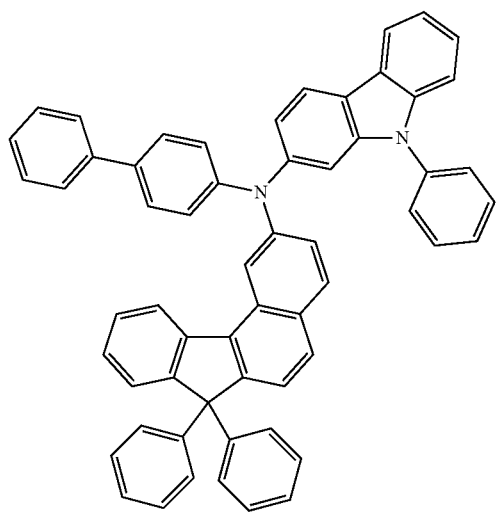
C-59
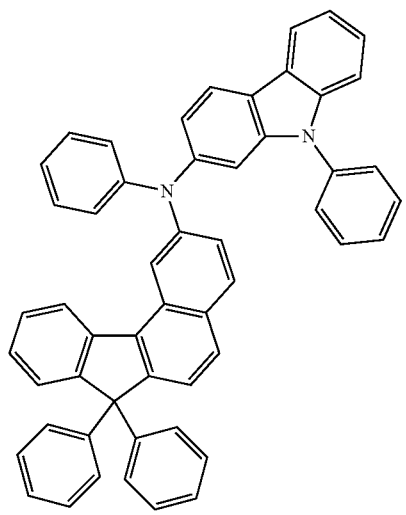
C-60
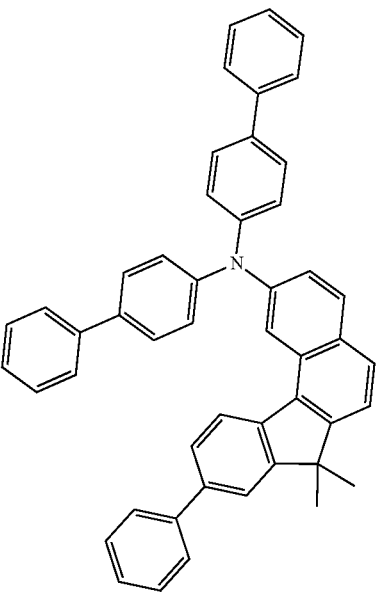
C-61
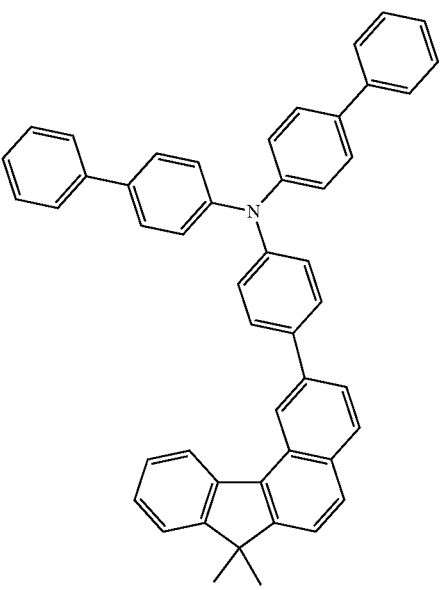

C-62
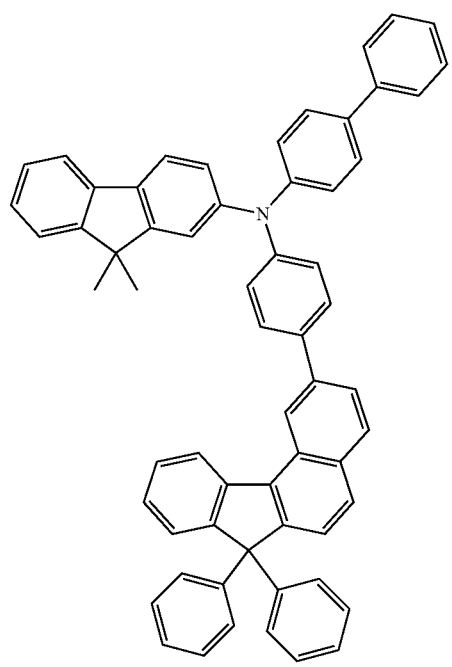
C-63
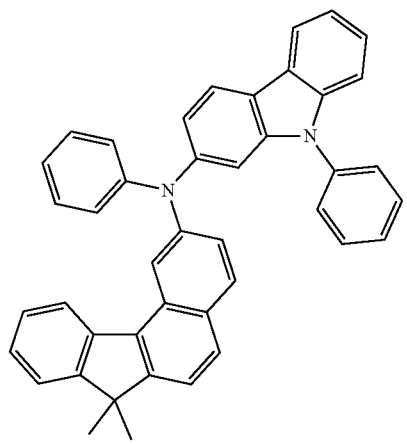
C-64
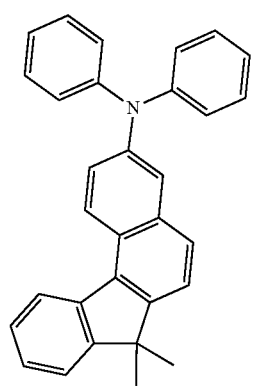
C-65
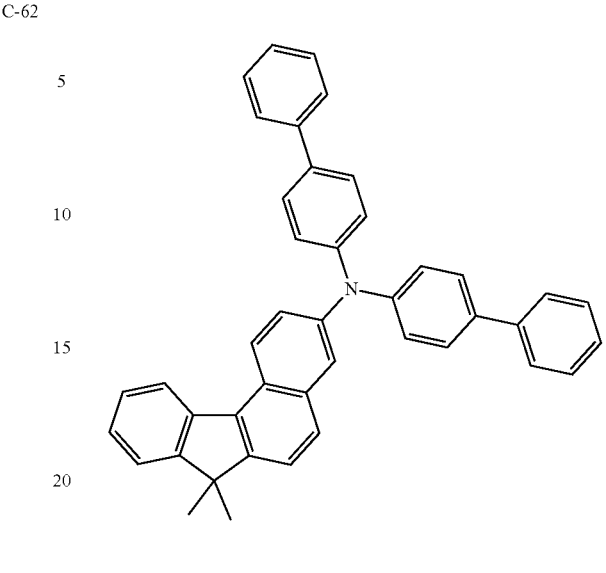
C-66
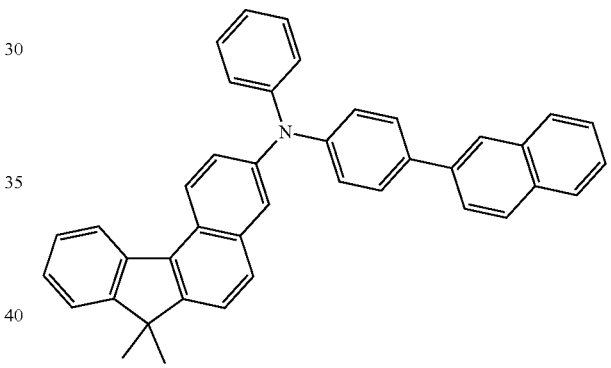
C-67
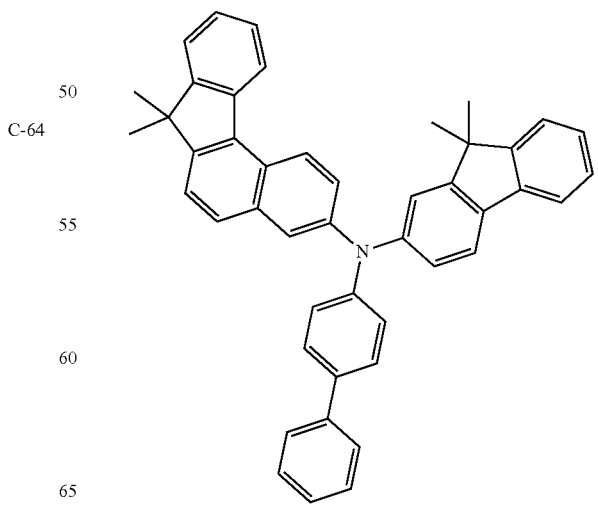

C-68
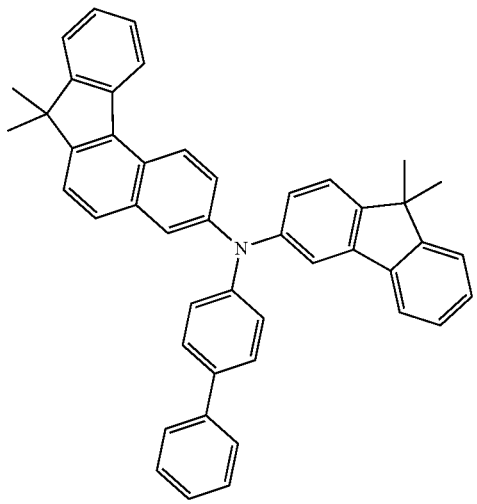
C-69
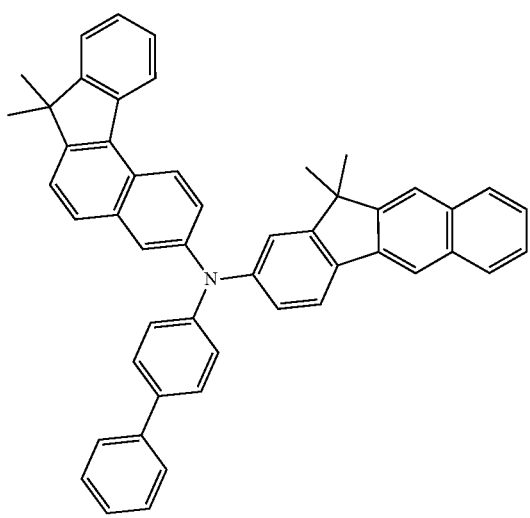
C-70
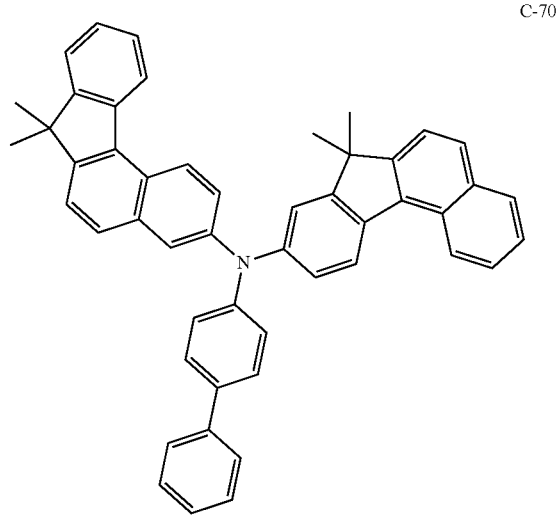
C-71
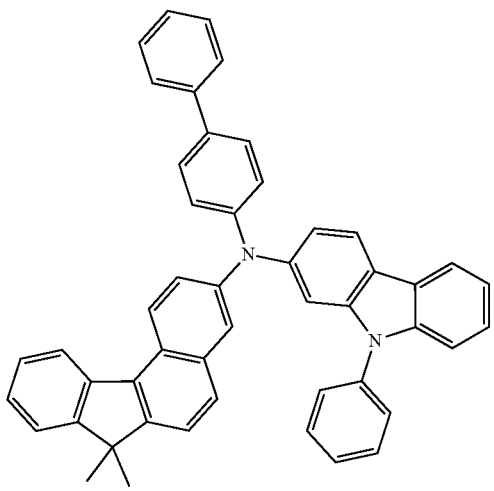
C-72
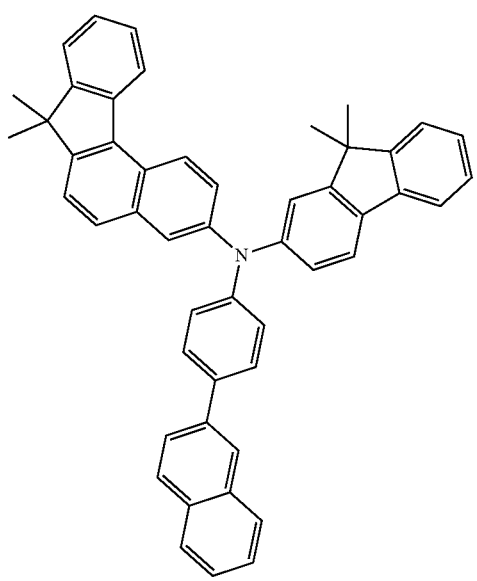
C-73
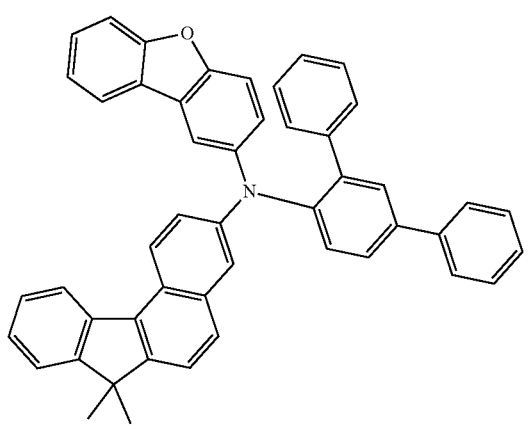

-continued
C-74
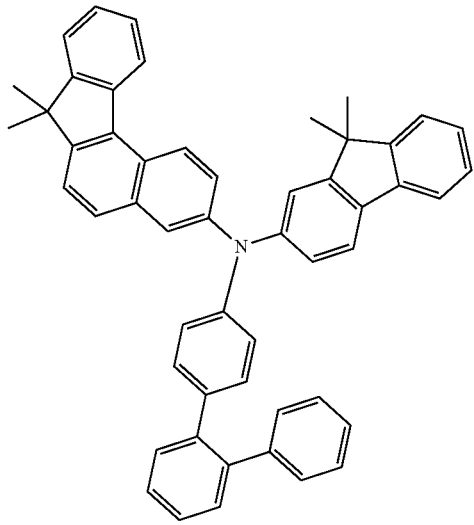
C-75
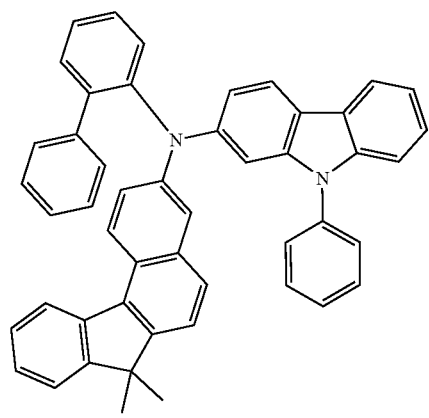
C-76
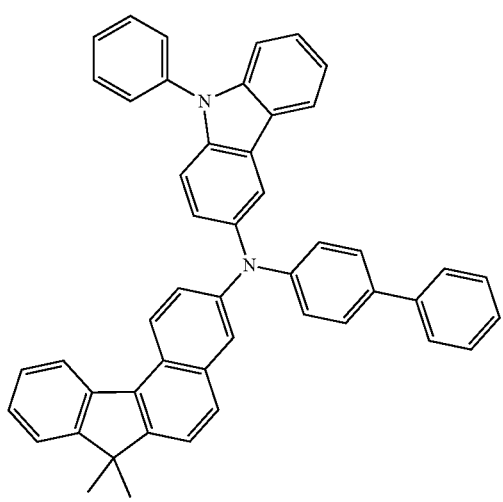
C-77
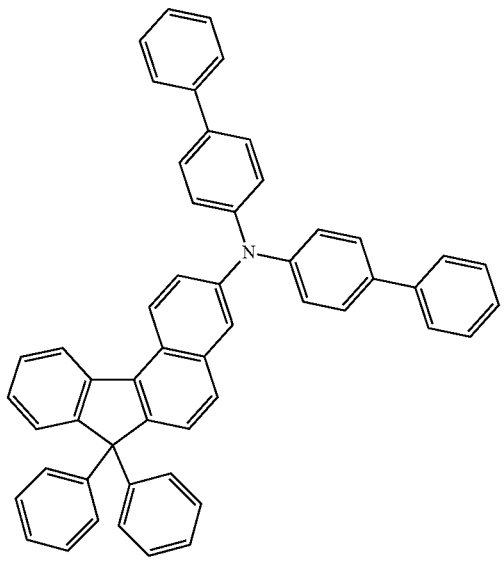
C-78
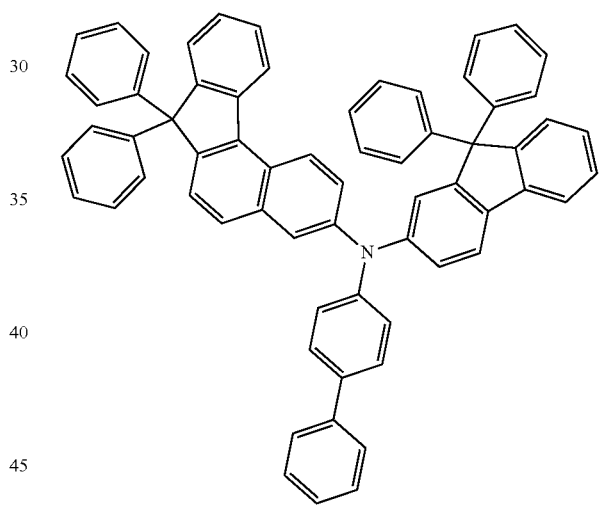
C-79
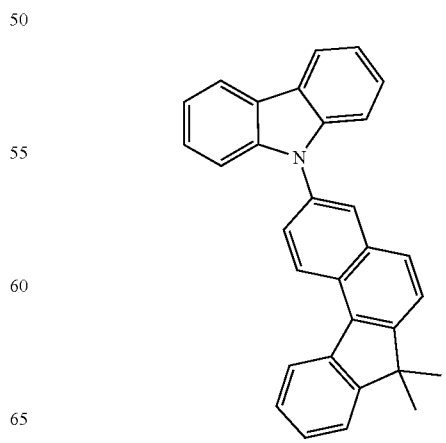

C-80
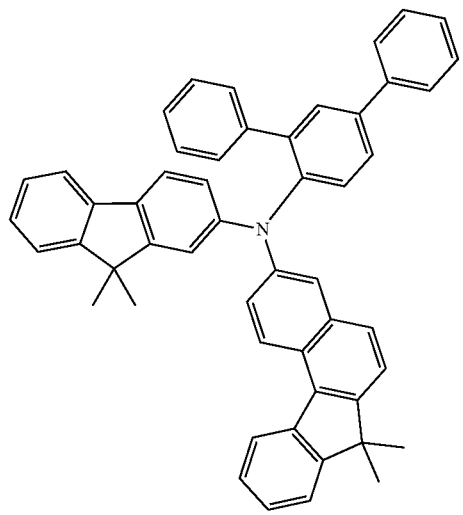
C-81
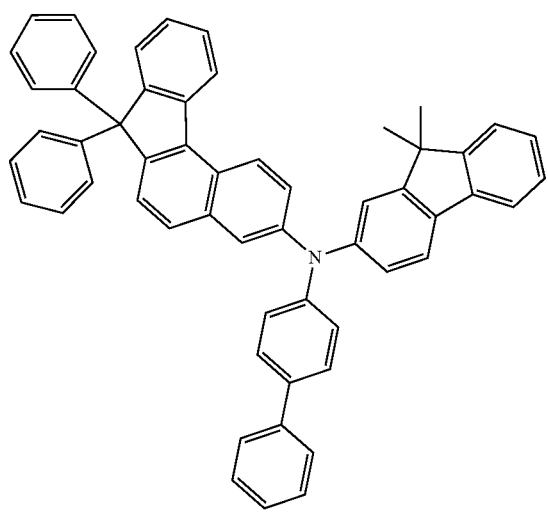
C-82
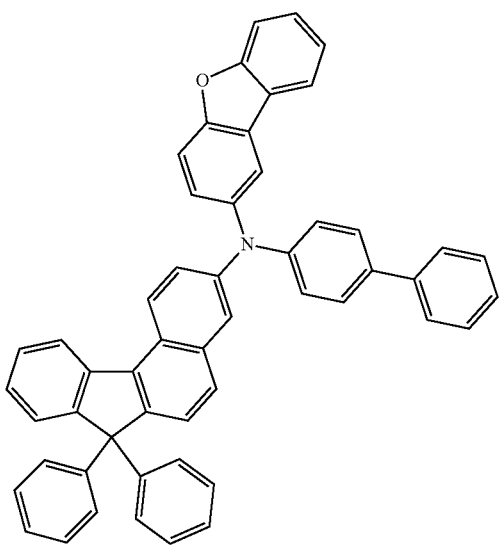
C-83
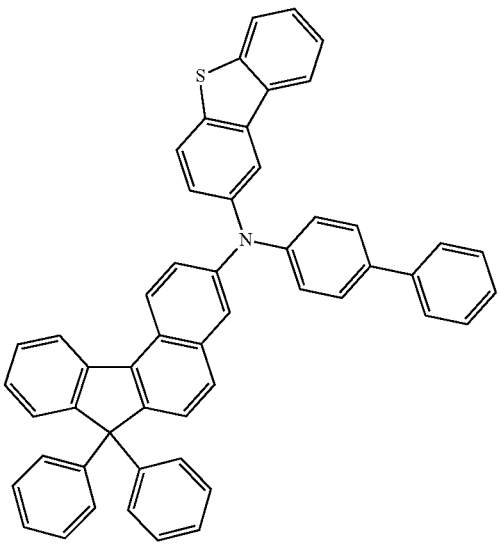
C-84
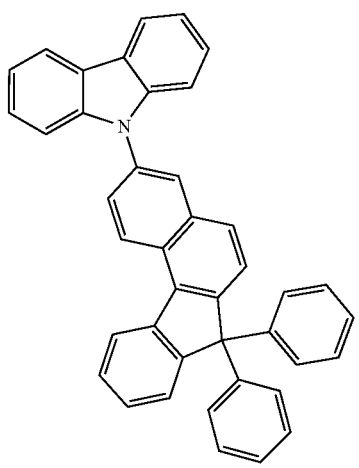
C-85
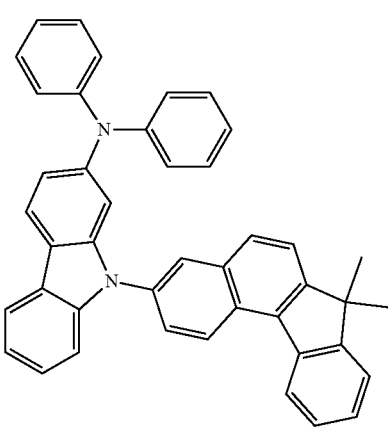

C-86
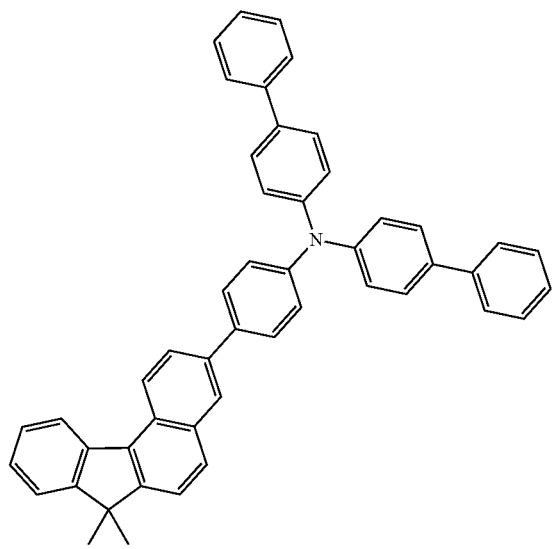
C-87
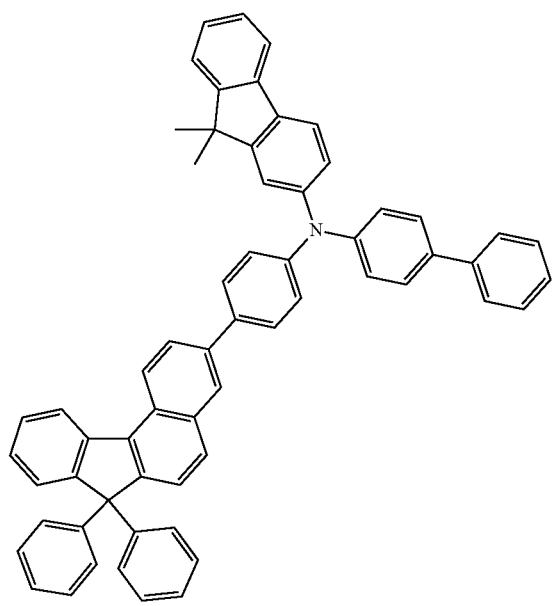
C-88
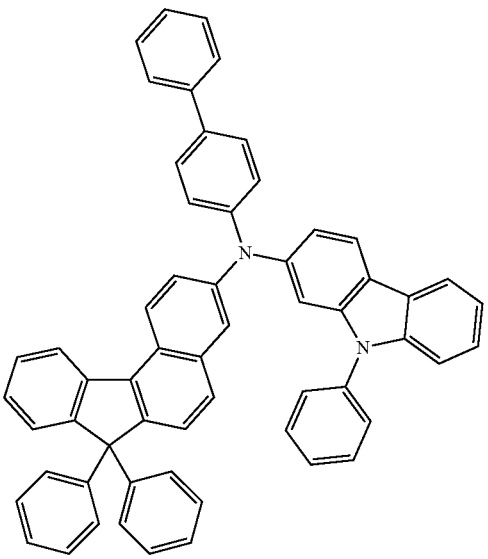
C-89
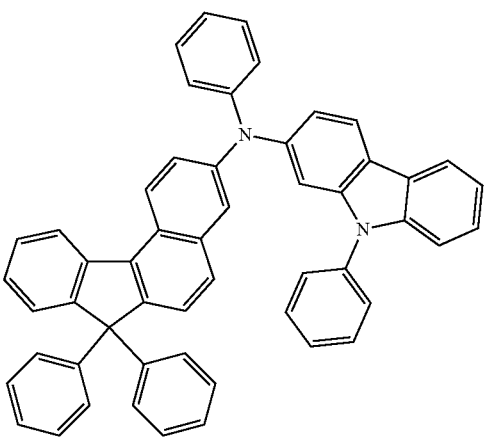
C-90
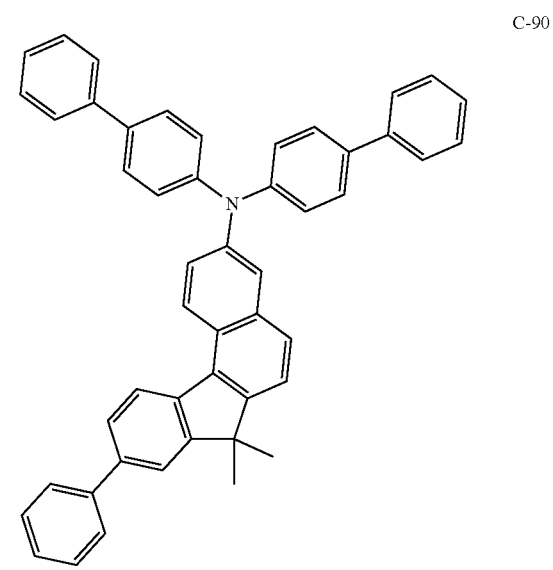 [SMILES: CC1(C)c2cc(-c3ccccc3)ccc2-c2c1ccc1cc(N(c3ccc(-c4ccccc4)cc3)c3ccc(-c4ccccc4)cc3)ccc21]

C-91
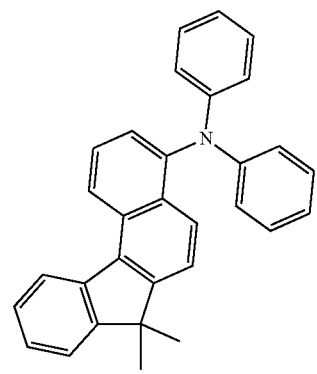
C-94
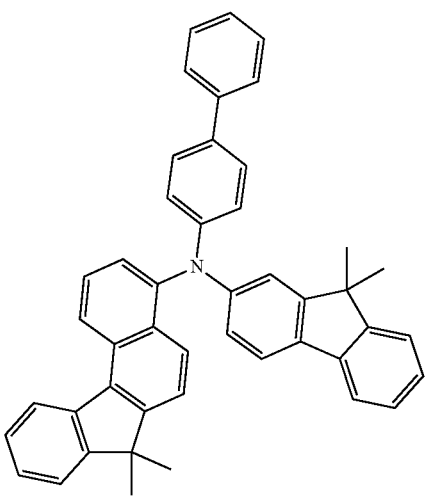
C-92
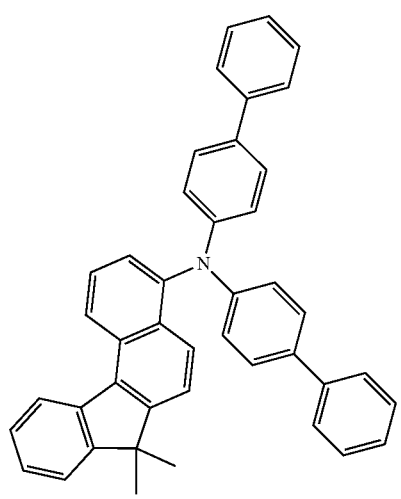
C-95
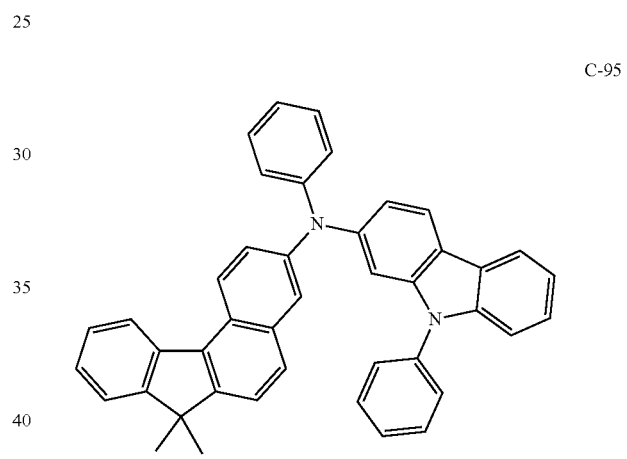
C-93
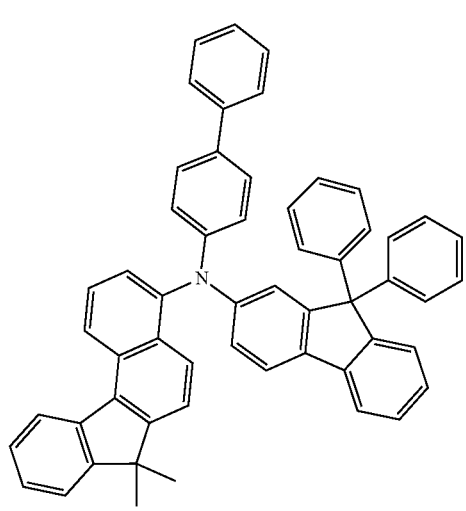
C-96
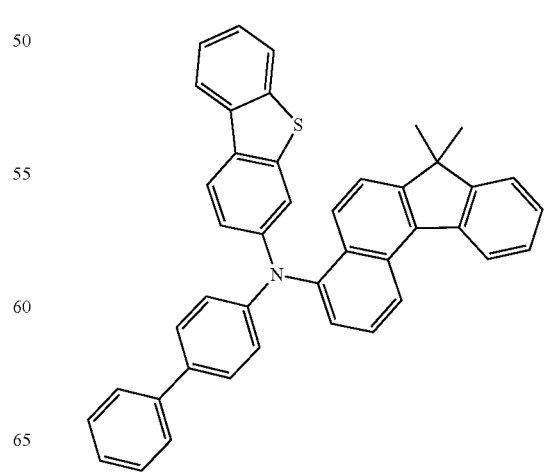

C-97
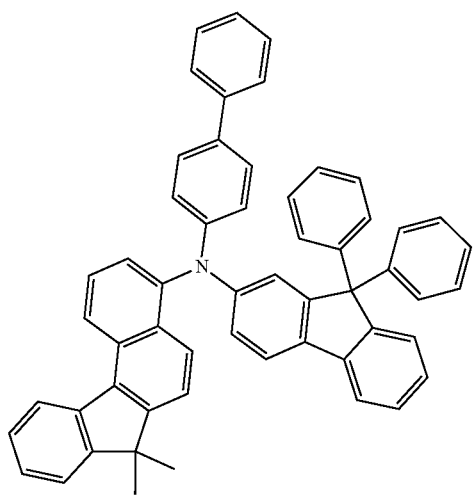
C-98
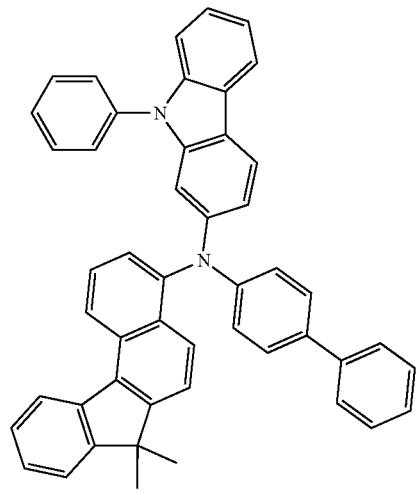
C-99
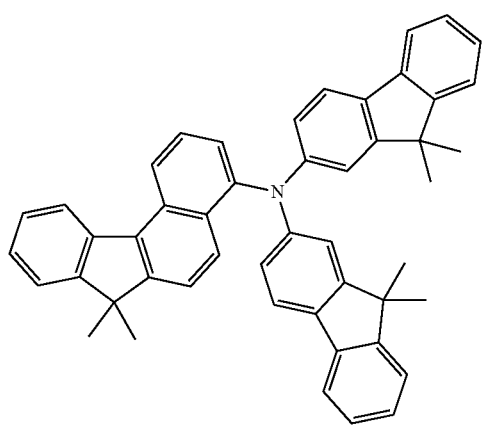
C-100
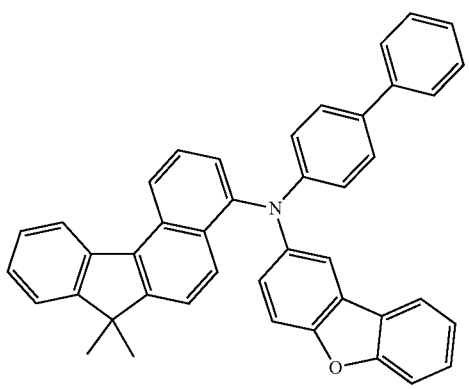
C-101
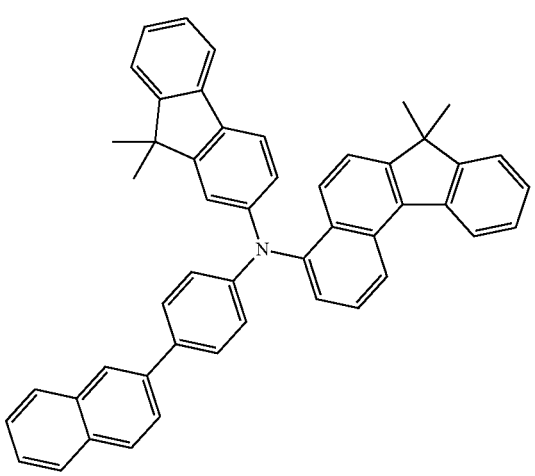
C-102
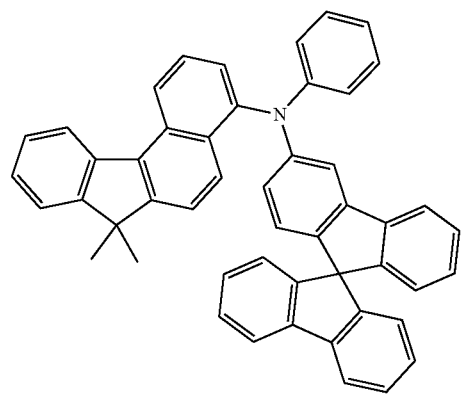

C-103
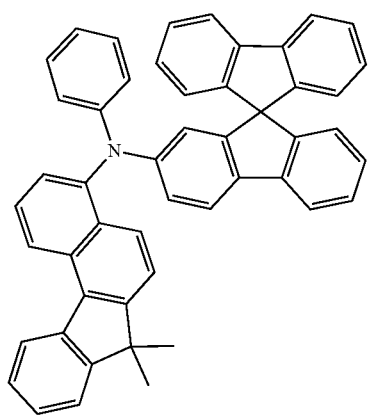
C-104
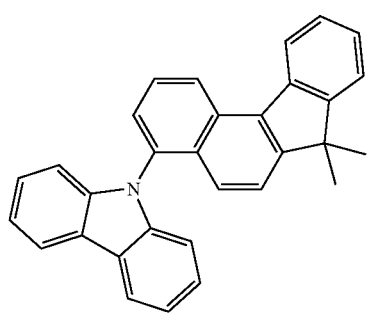
C-105
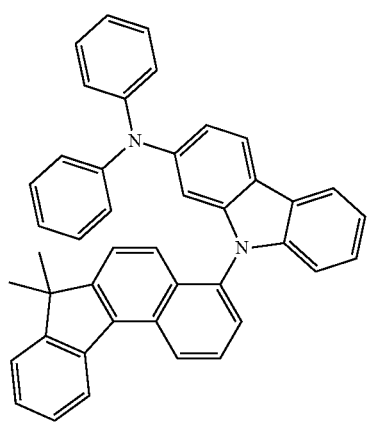
C-106
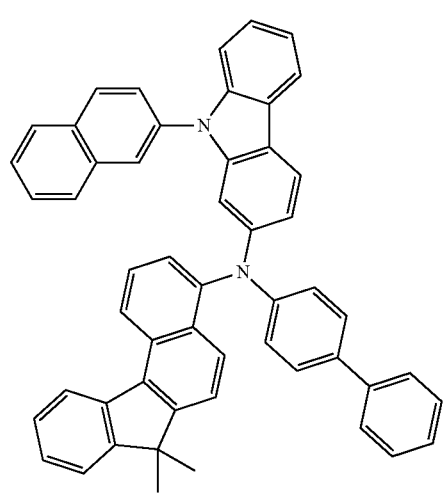
C-107
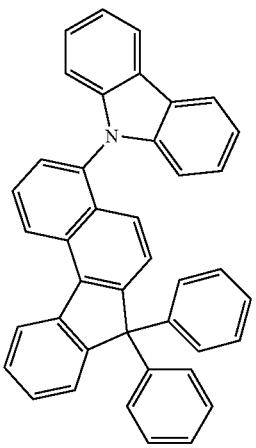
C-108
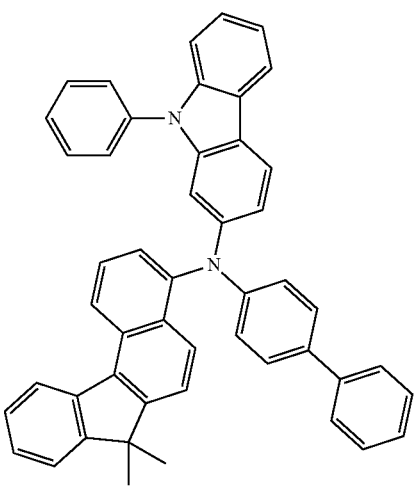
C-109
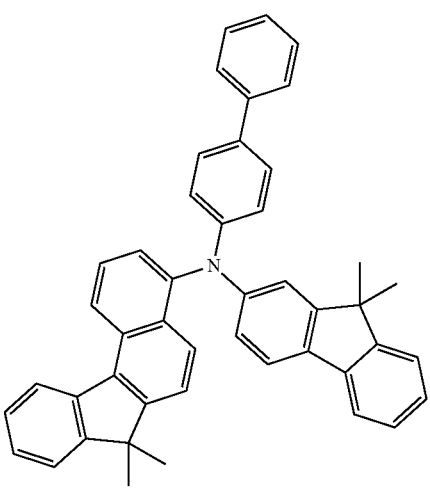

-continued
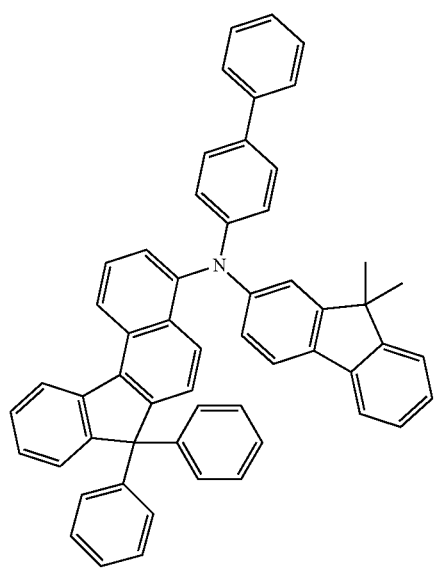
C-110
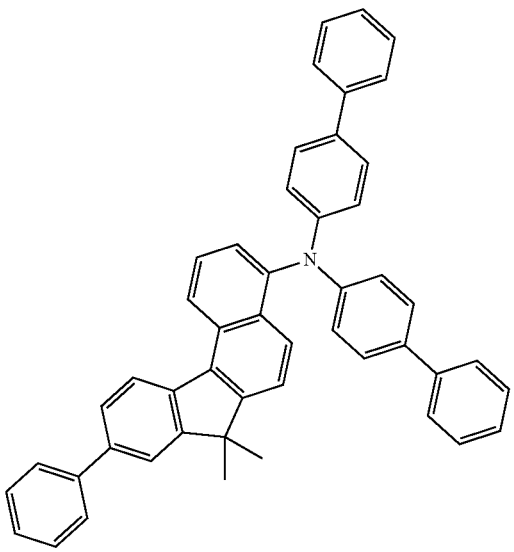
C-112
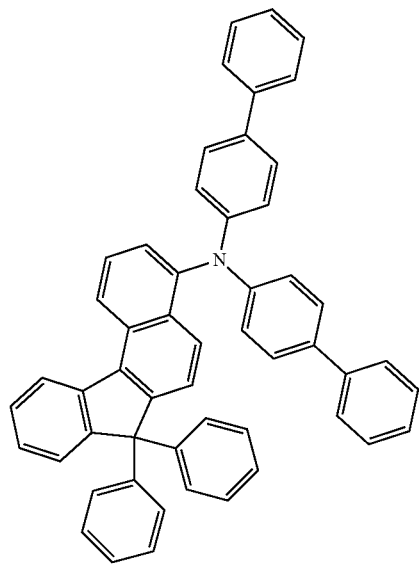
C-111
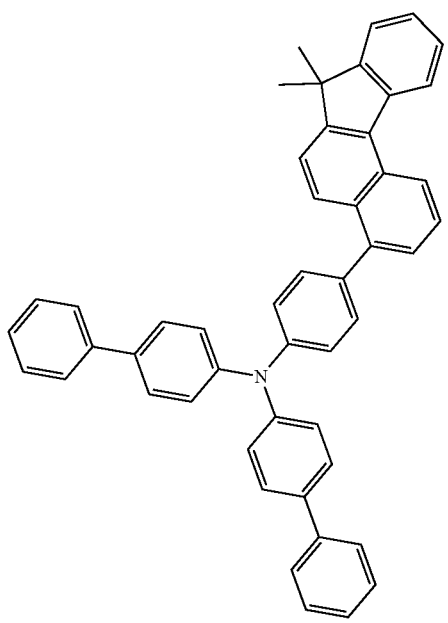
C-113

C-114
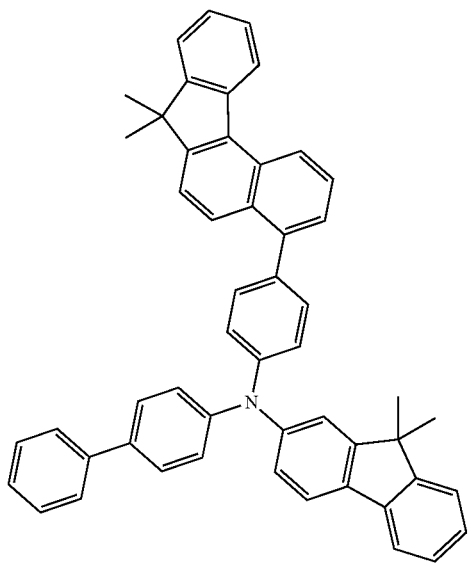
C-115
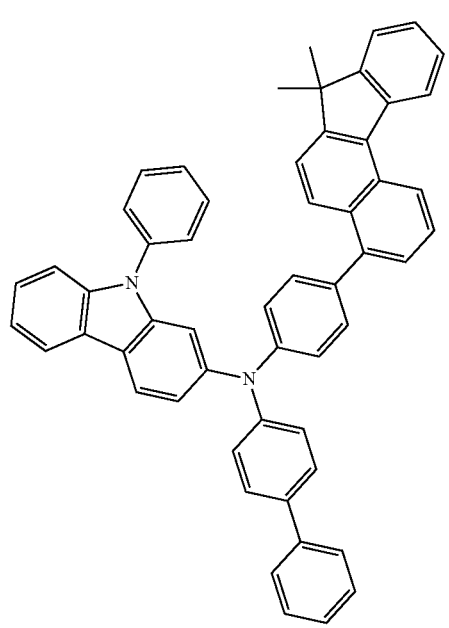
C-116
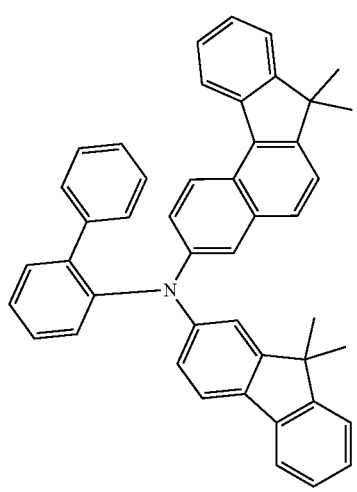
C-117
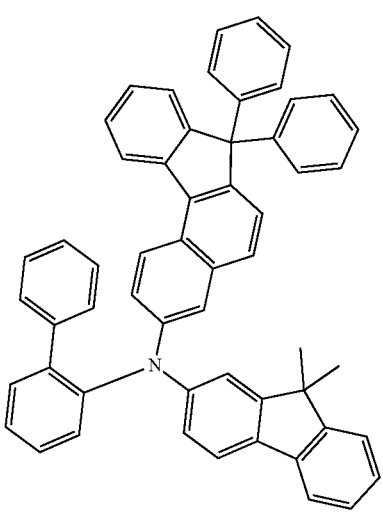
C-118
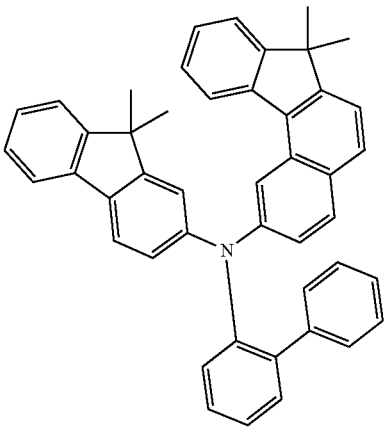
C-119
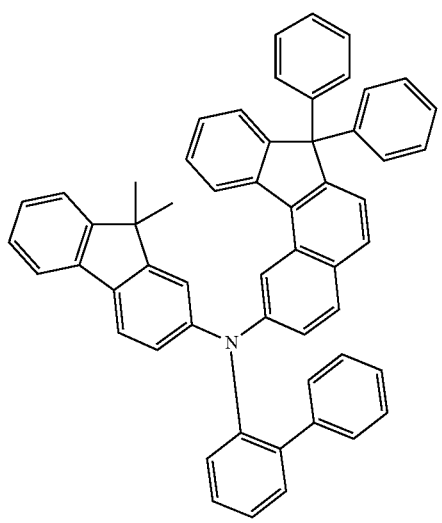

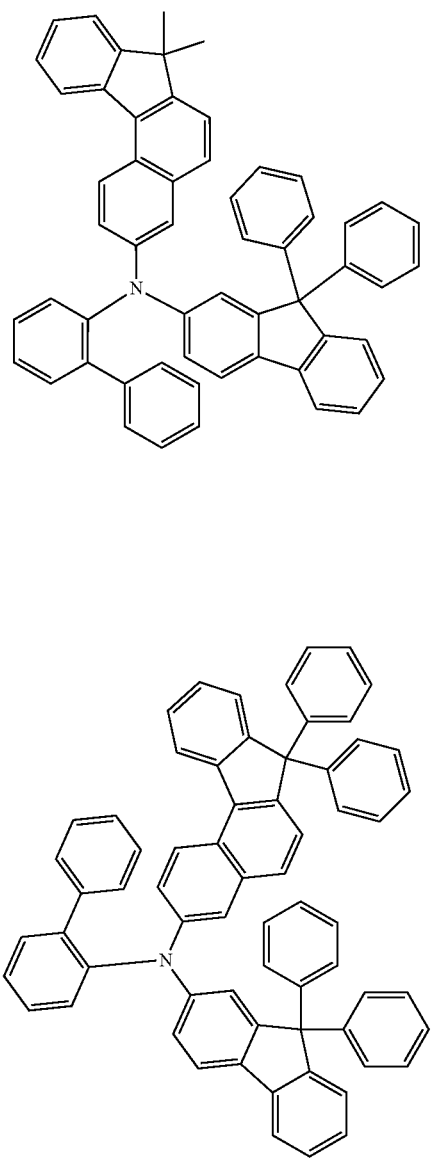
C-120
C-121
The compound of formula 1 according to the present disclosure can be prepared by a synthetic method known to a person skilled in the art. For example, it can be prepared according to the following reaction schemes.
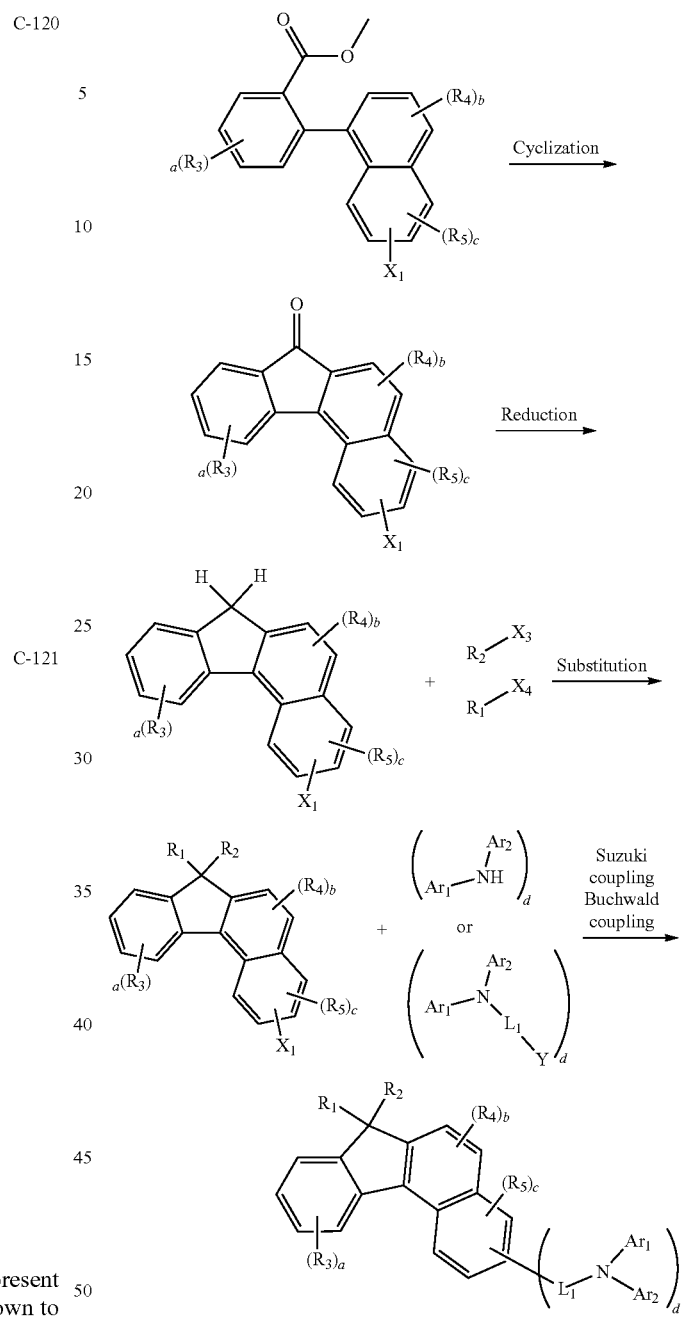
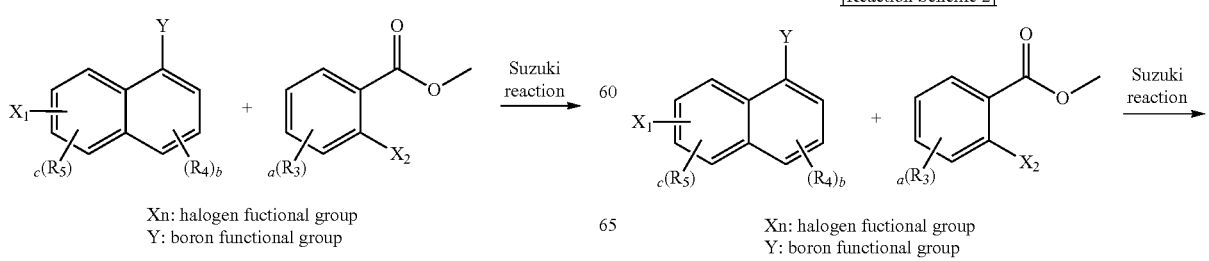

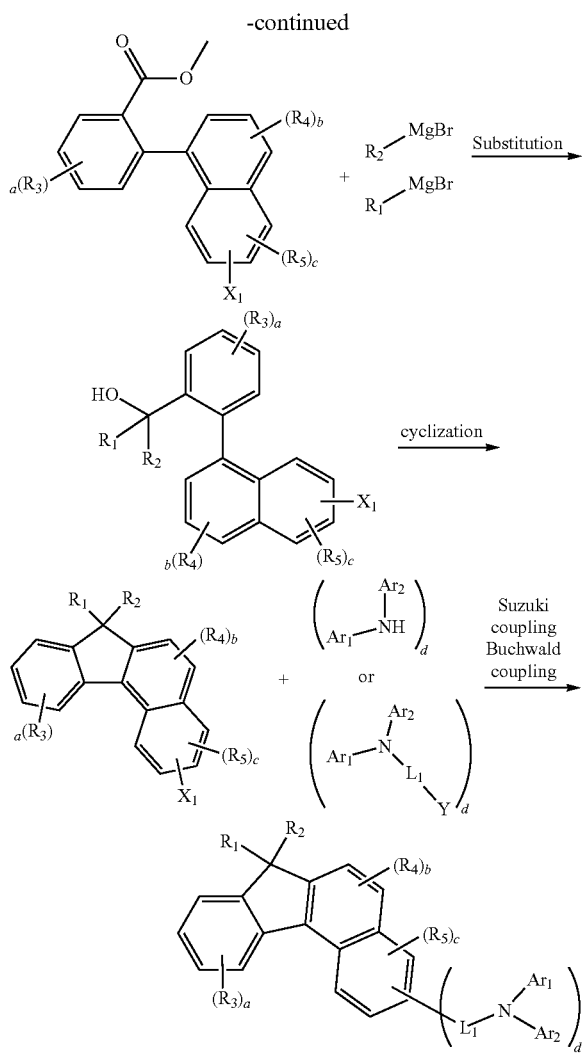

wherein Ar₁, Ar₂, L₁, R₁ to R₅, and a to d are as defined in formula 1.

The hole transport zone of the present disclosure may be composed of one or more layers selected from the group consisting of a hole transport layer, a hole injection layer, an electron blocking layer, and a hole auxiliary layer. Each layer may consist of one or more layers.

According to one embodiment of the present disclosure, the hole transport zone comprises a hole transport layer. In addition, the hole transport zone may comprise a hole transport layer and further comprise one or more layers of a hole injection layer, an electron blocking layer, and a hole auxiliary layer.

In addition, the present disclosure provides an organic electroluminescent material comprising the organic electroluminescent compound of formula 1, and an organic electroluminescent device comprising the material.

The above material may be a hole transport material, a hole auxiliary material, or a light-emitting auxiliary material, specifically a hole transport material, a hole auxiliary material, or a light-emitting auxiliary material of an organic electroluminescent device emitting red light. When there are two or more hole transport layers, the material may be a hole transport material (hole auxiliary material) comprised in the hole transport layer adjacent to the light-emitting layer.

The above material may consist of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

According to one embodiment of the present disclosure, the organic electroluminescent device of the present disclosure may further comprise an azine-based compound as one or more of an electron transport material, an electron injection material, an electron buffer material, and a hole blocking material, besides the organic electroluminescent compound of the present disclosure.

The organic electroluminescent compound of formula 1 of the present disclosure may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in at least one layer of the hole transport layer, the hole auxiliary layer, the light-emitting auxiliary layer, and the light-emitting layer. When there are two or more hole transport layers, the organic electroluminescent compound can be used in at least one of the layers. For example, when used in the hole transport layer, the organic electroluminescent compound of the present disclosure may be comprised as a hole transport material. In addition, when used in the light-emitting layer, the organic electroluminescent compound of the present disclosure may be comprised as a host material.

The light-emitting layer may comprise one or more hosts and one or more dopants. If necessary, the light-emitting layer may comprise a co-host material, i.e., a plurality of host materials of two or more. The organic electroluminescent compound of the present disclosure can be used as a co-host material.

The host used in the present disclosure may be a phosphorescent host compound or a fluorescent host compound, and the host compounds are not particularly limited.

The dopant comprised in the organic electroluminescent device according to the present disclosure may be at least one phosphorescent or fluorescent dopant, preferably at least one phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may include the compound represented by the following formula 101, but is not limited thereto.

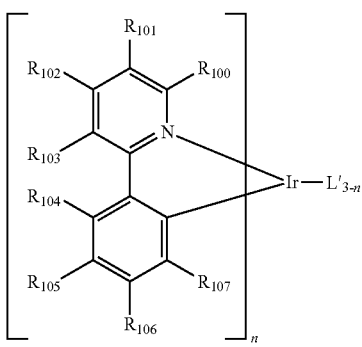

(101)

In formula 101, L' is selected from any one of the following structures 1 to 3:

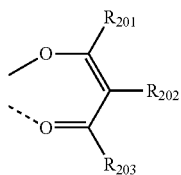

[Structure 1]

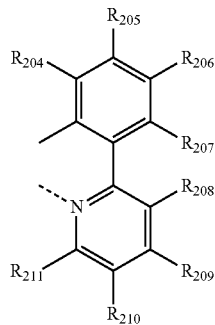

[Structure 2]

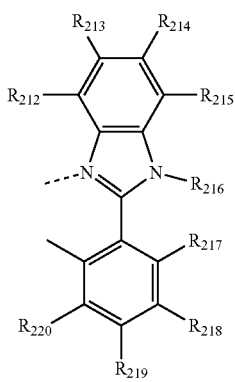

[Structure 3]

$R_{100}$ to $R_{103}$ each independently represent hydrogen, deuterium, a halogen, a (C1-C30)alkyl unsubstituted or substituted with deuterium(s) or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine;

$R_{104}$ to $R_{107}$ each independently represent hydrogen, deuterium, a halogen, a (C1-C30)alkyl unsubstituted or substituted with deuterium(s) or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring, e.g., a substituted or unsubstituted, naphthalene, fluorene, dibenzothiophene, dibenzofuran, indenopyridine, benzofuropyridine or benzothienopyridine ring, together with benzene;

$R_{201}$ to $R_{220}$ each independently, represent hydrogen, deuterium, a halogen, a (C1-C30)alkyl unsubstituted or substituted with deuterium(s) or a halogen(s), a substituted or unsubstituted (C3-C30)cycloalkyl, or a substituted or unsubstituted (C6-C30)aryl; or may be linked to an adjacent substituent to form a ring; and n represents an integer of 1 to 3.

The specific examples of the dopant compound are as follows, but are not limited thereto.

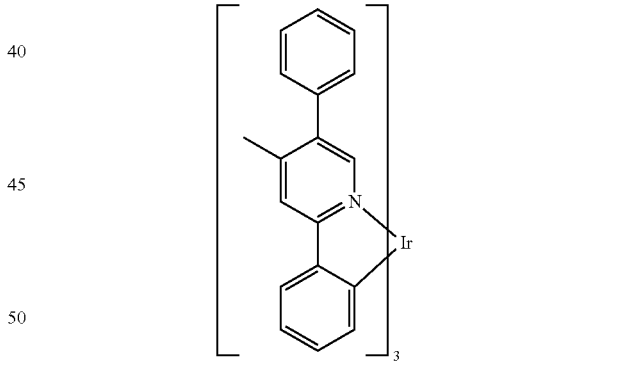

D-1

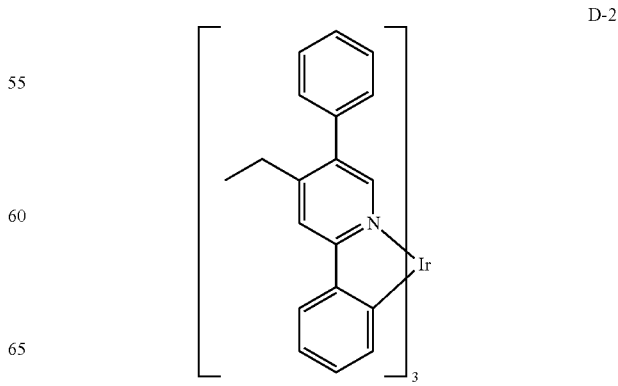

D-2

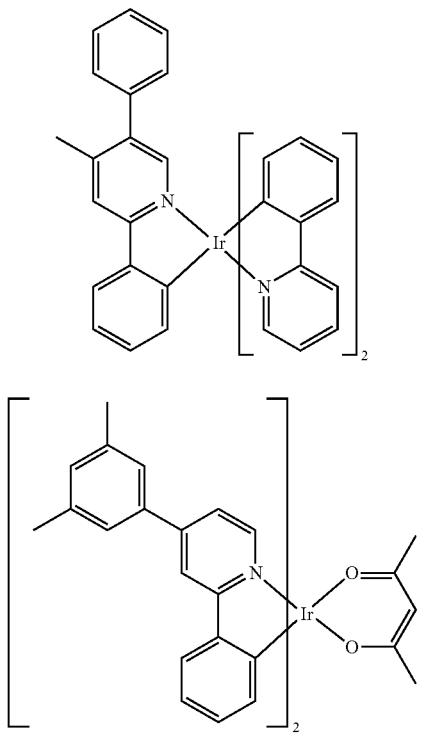
D-3
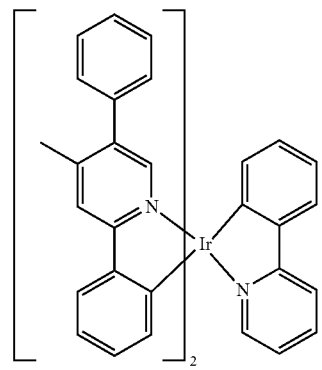
D-4
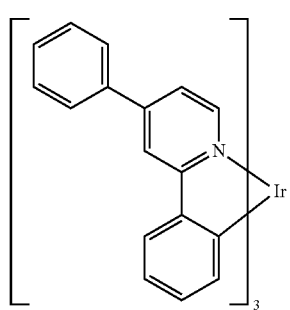
D-5
D-6
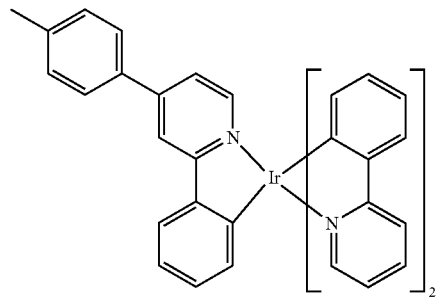
D-7
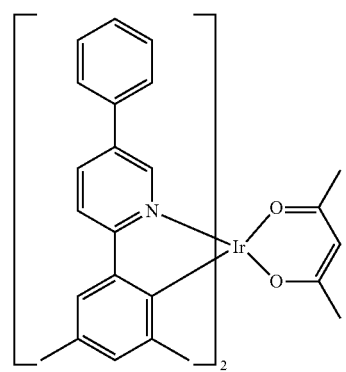
D-8
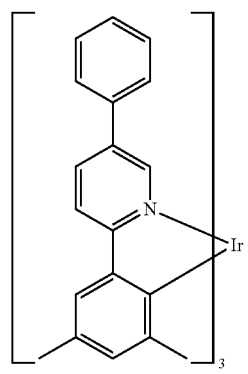
D-9
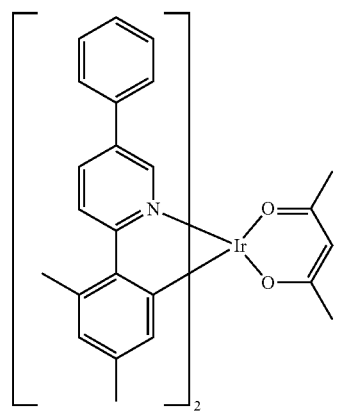
D-10

D-11
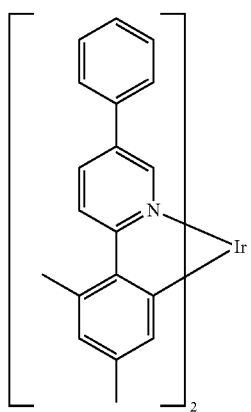
D-12
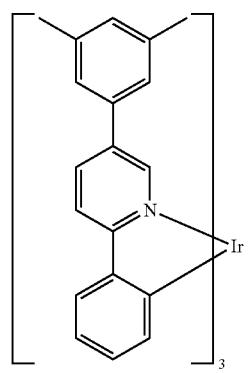
D-13
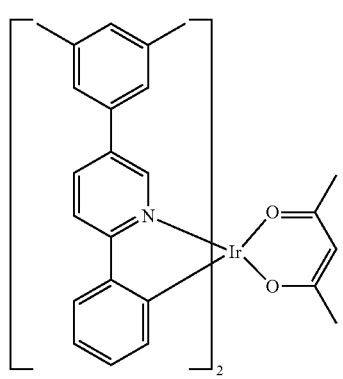
D-14
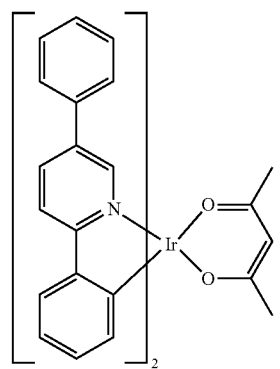
D-15
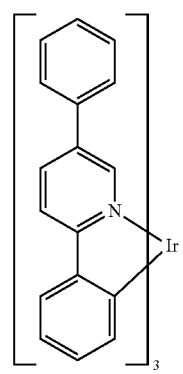
D-16
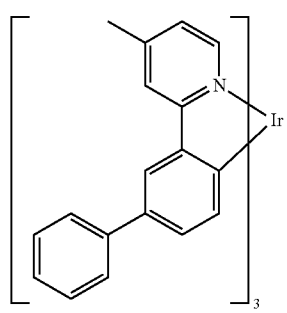
D-17
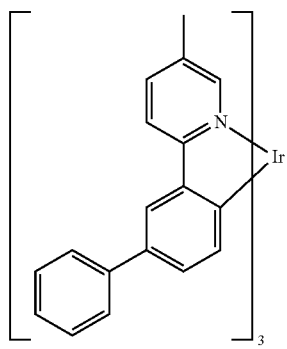
D-18
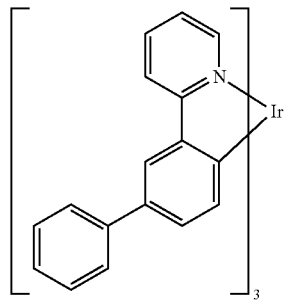

D-19
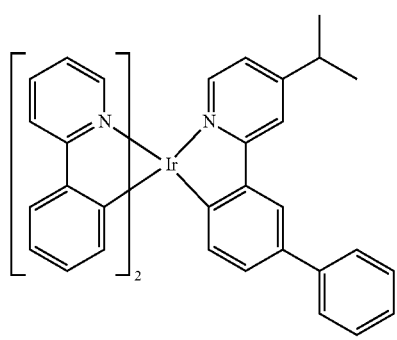
D-20
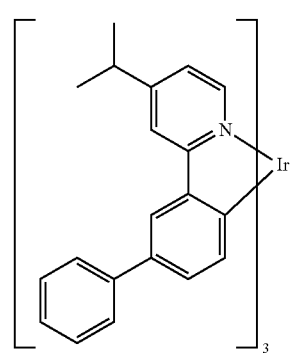
D-21
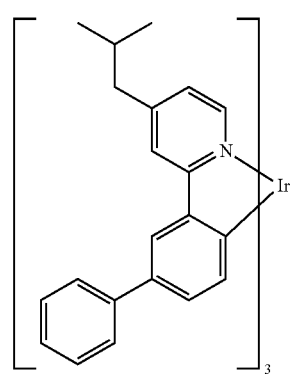
D-22
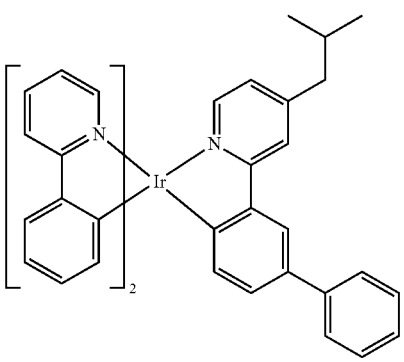
D-23
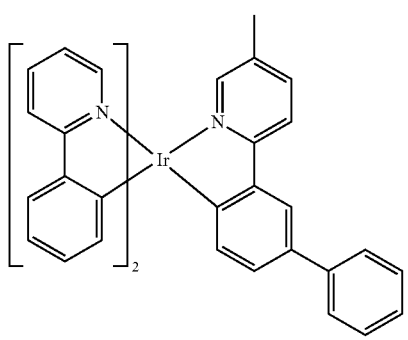
D-24
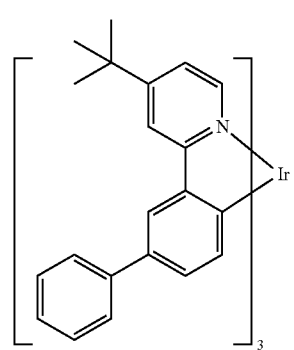
D-25
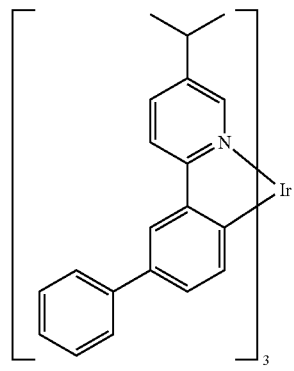
D-26
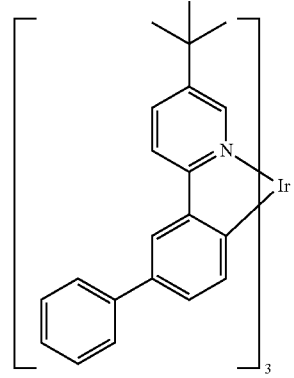

D-27
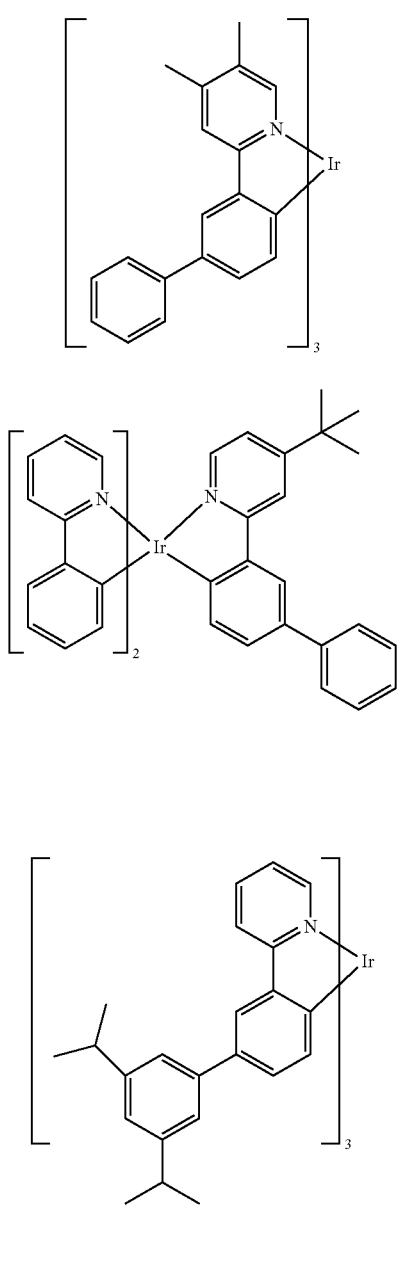
D-28
D-29
D-30
D-31
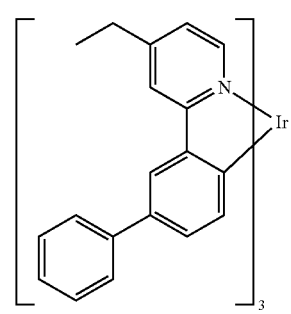
D-32
D-33
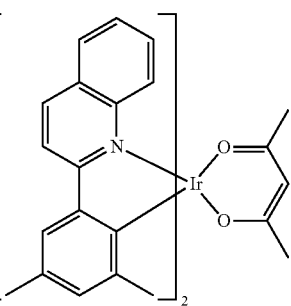
D-34
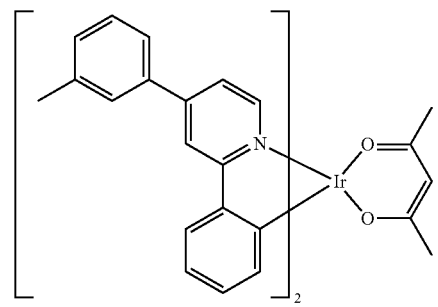
D-35
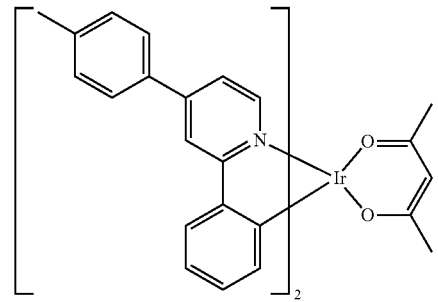

-continued
D-36
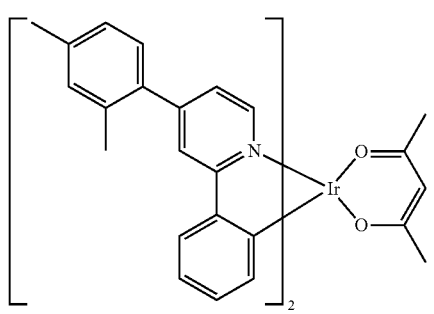
D-37
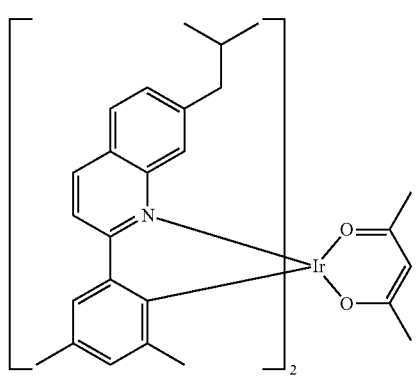
D-38
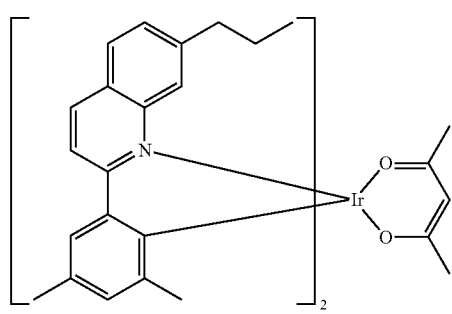
D-39
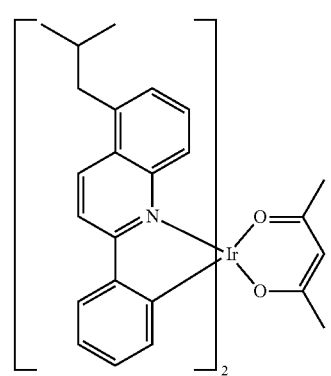
-continued
D-40
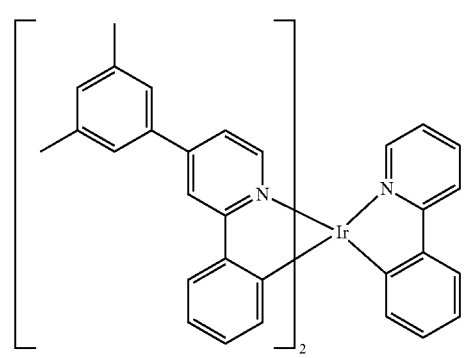
D-41
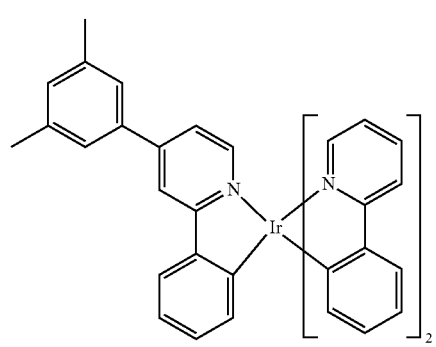
D-42
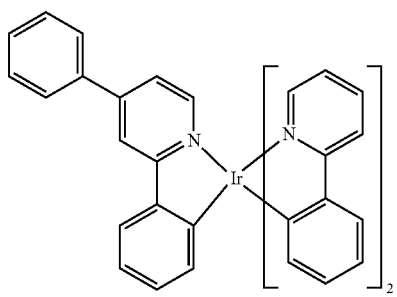
D-43
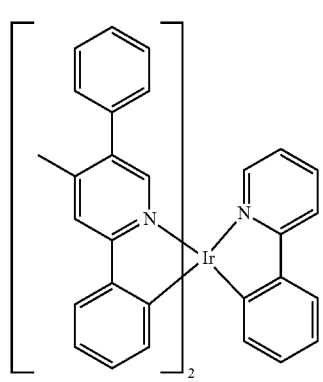

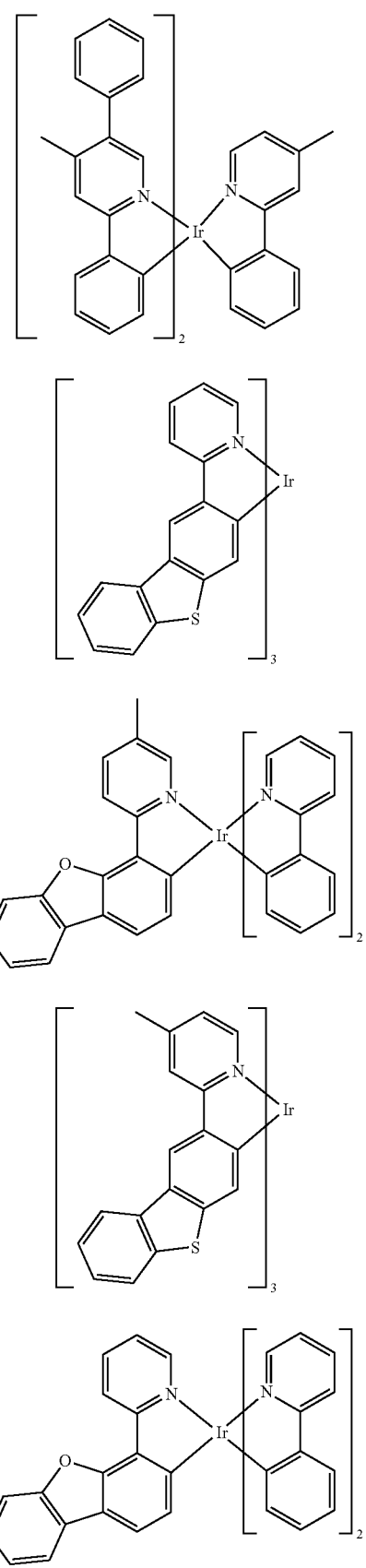
D-44
D-45
D-46
D-47
D-48
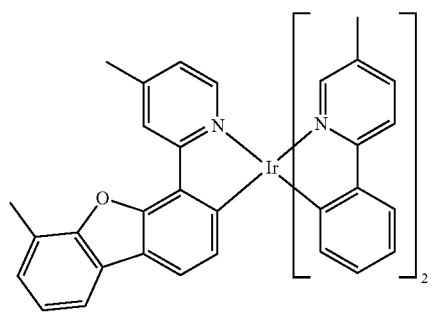
D-49
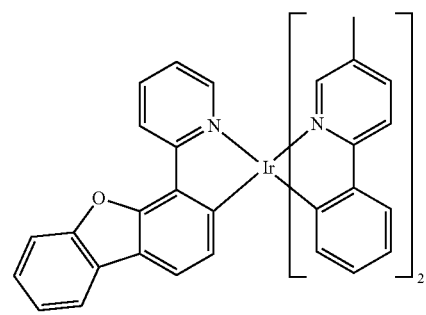
D-50
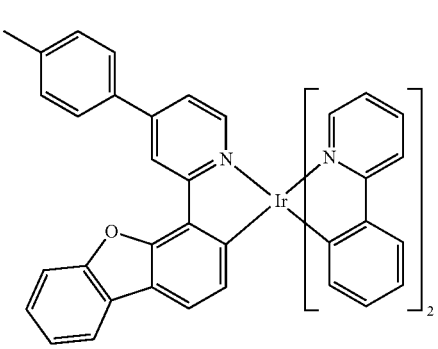
D-51
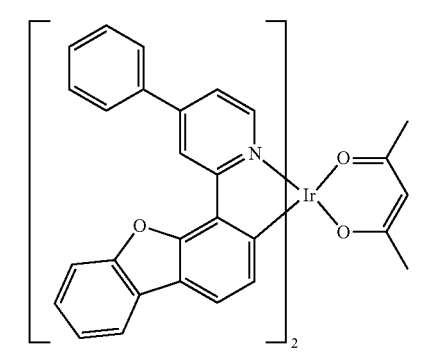
D-52
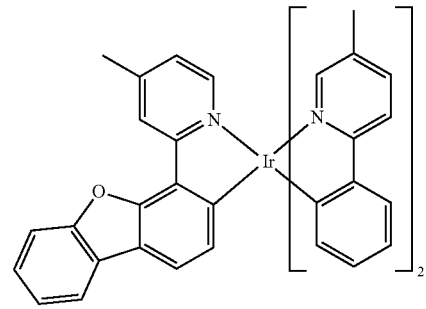
D-53

-continued
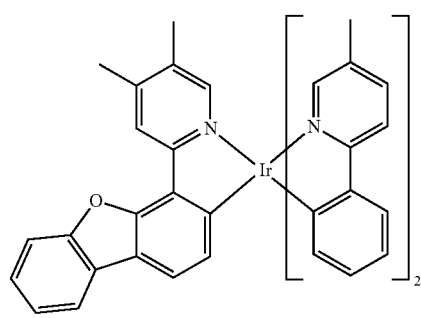
D-54
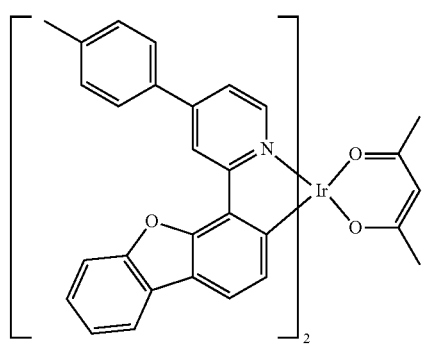
D-55
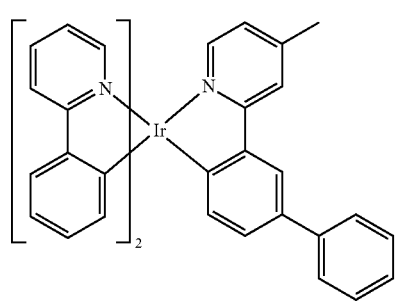
D-56
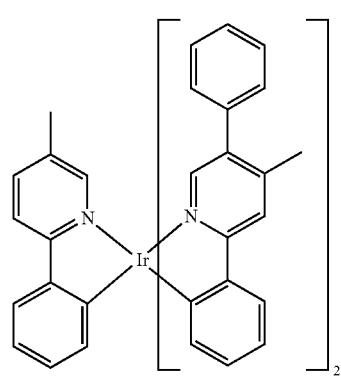
D-57
-continued
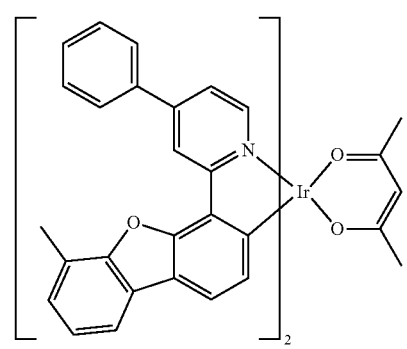
D-58
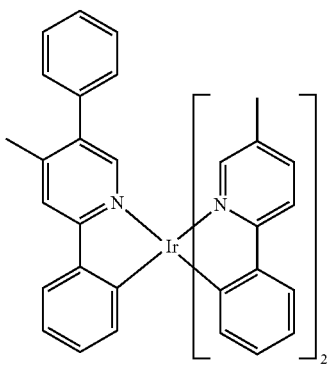
D-59
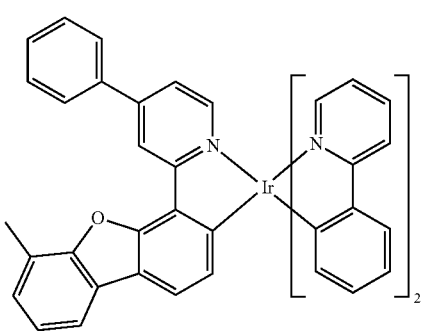
D-60
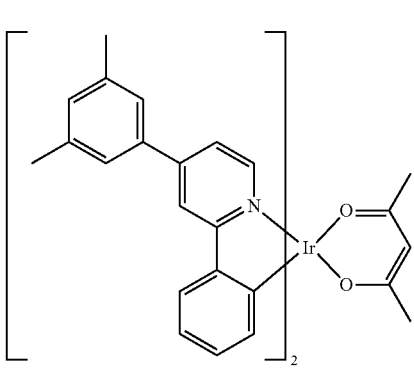
D-61

-continued
D-62
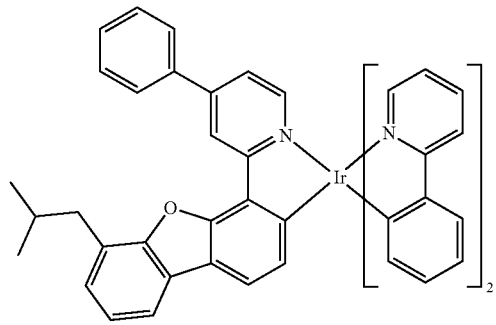
D-63
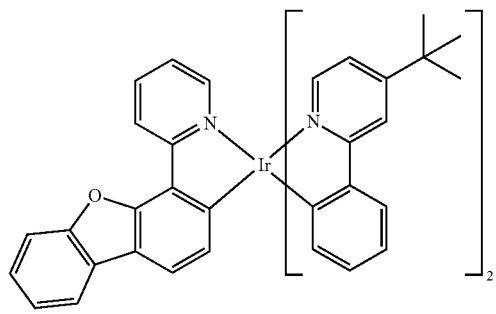
D-64
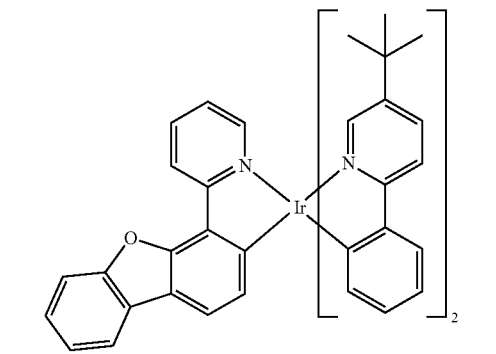
D-65
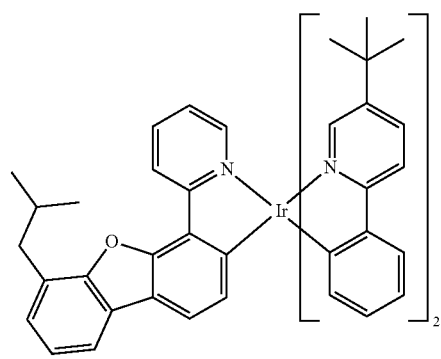
-continued
D-66
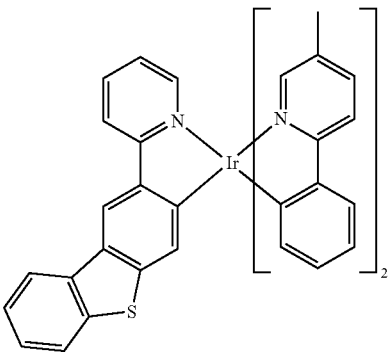
D-67
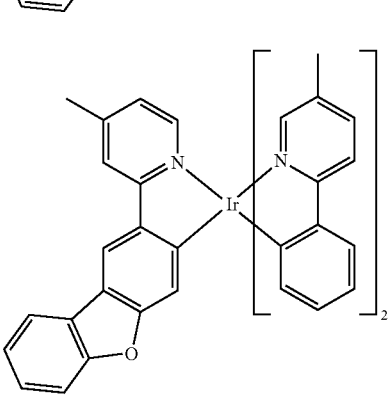
D-68
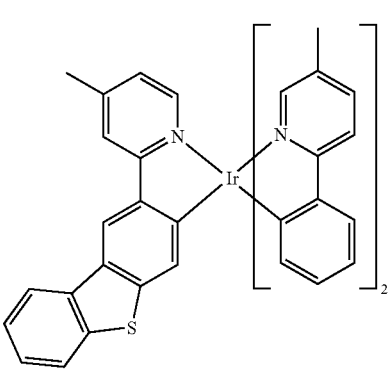
D-69
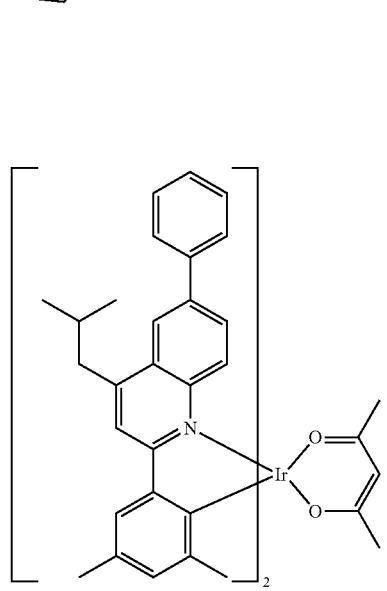

D-70
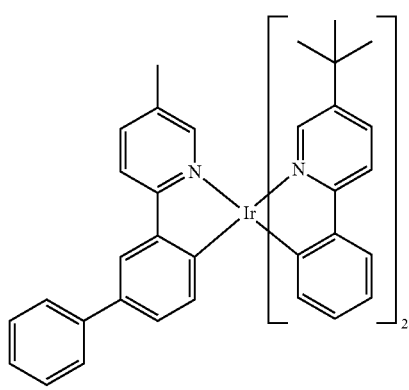
D-71
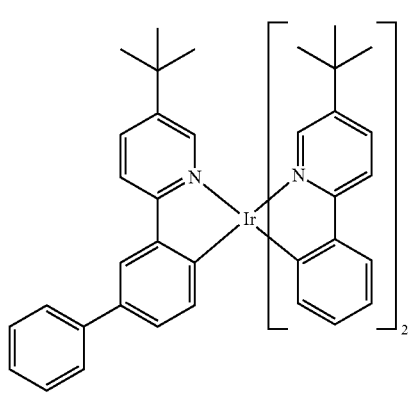
D-72
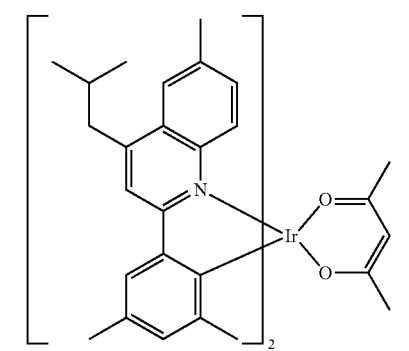
D-73
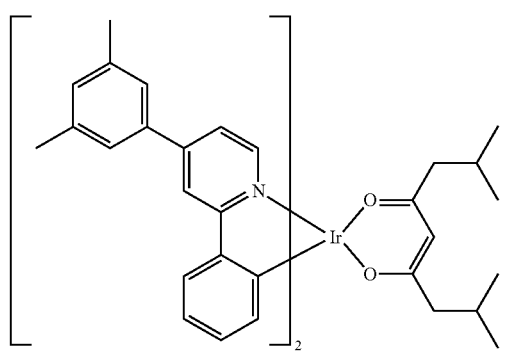
D-74
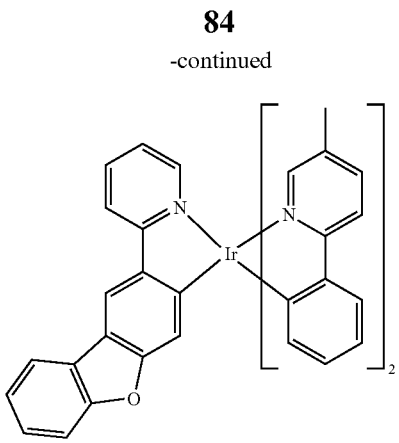
D-75
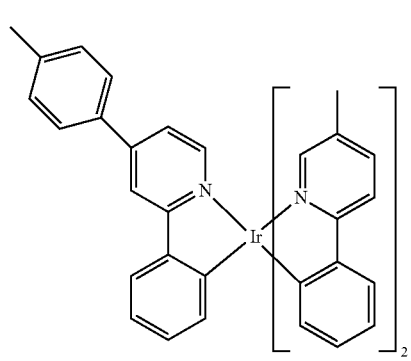
D-76
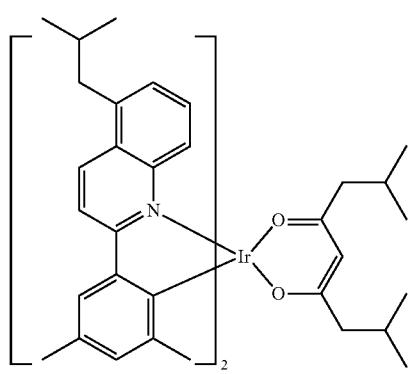
D-77
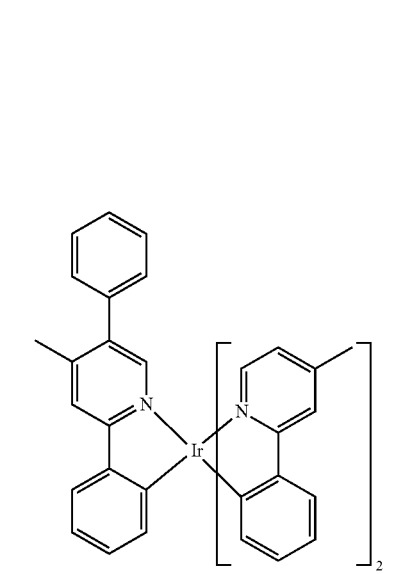

-continued
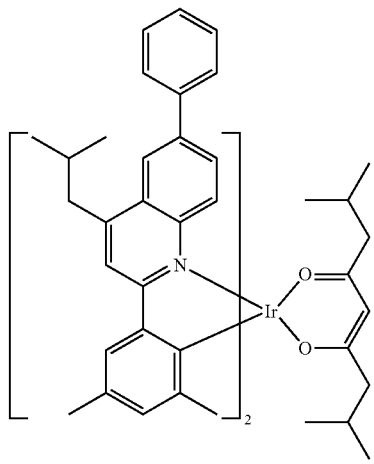
D-78
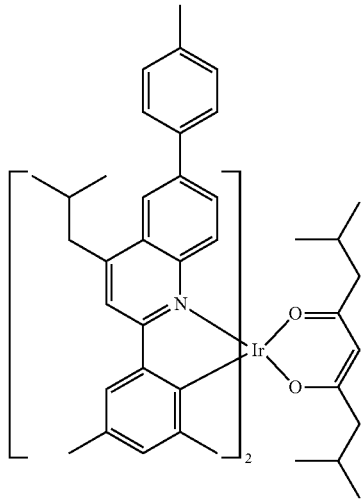
D-81
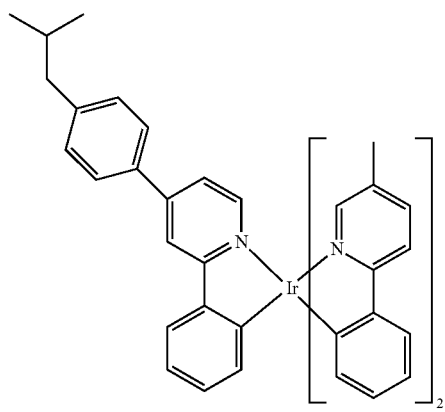
D-79
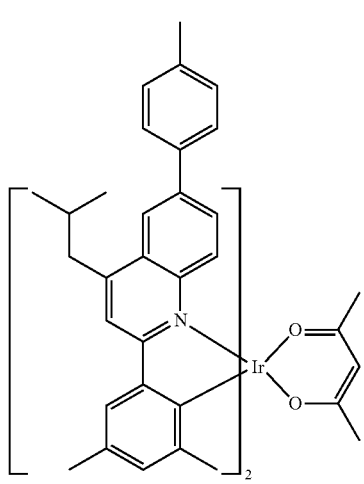
D-82
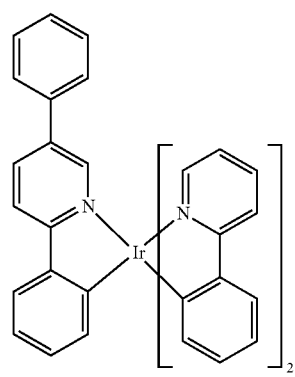
D-80
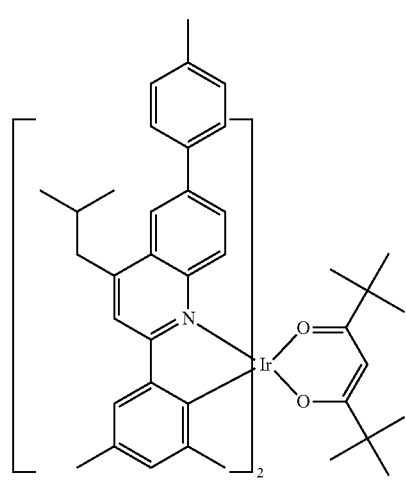
D-83

D-84
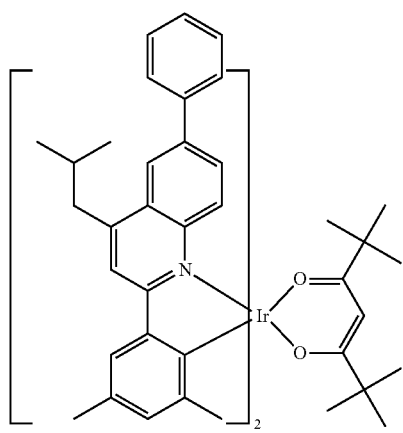
D-85
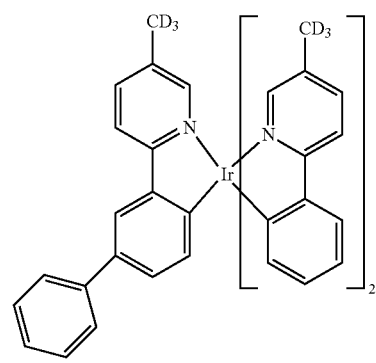
D-86
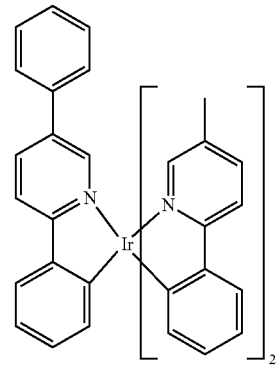
D-87
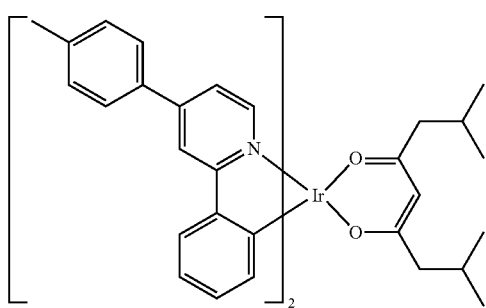
D-88
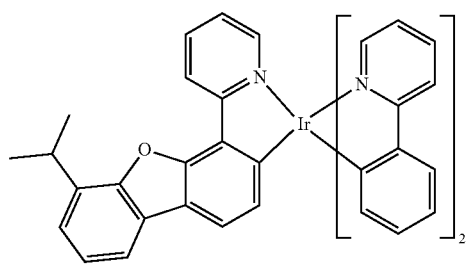
D-89
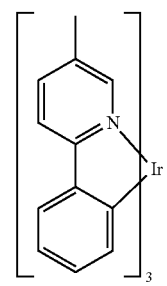
D-90
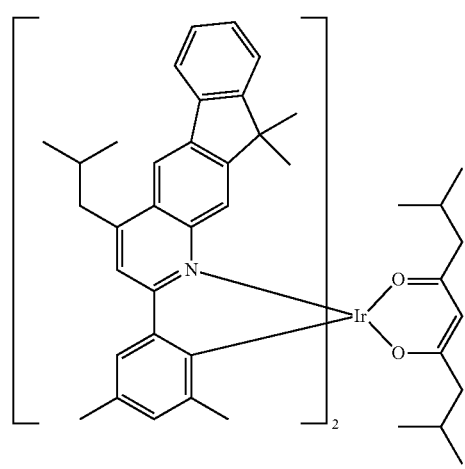
D-91
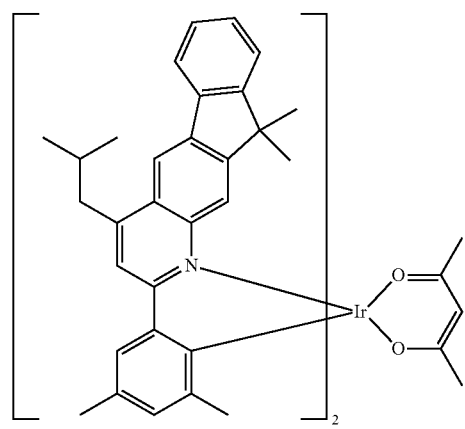

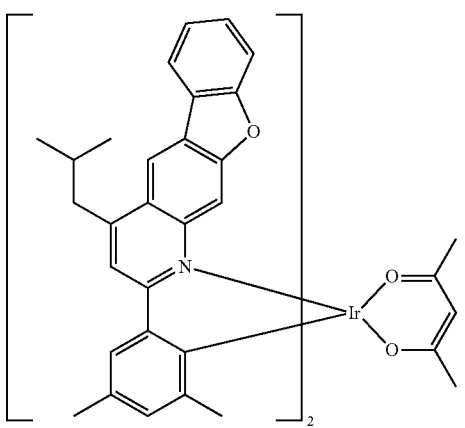
D-92
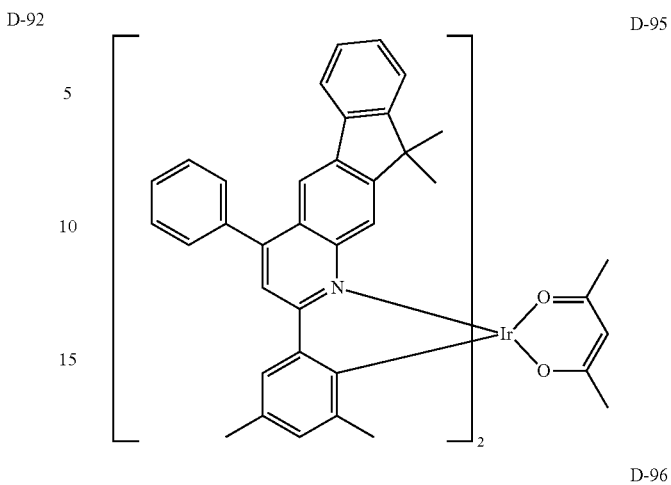
D-95
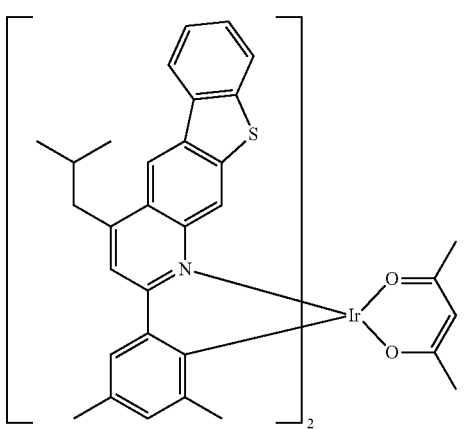
D-93
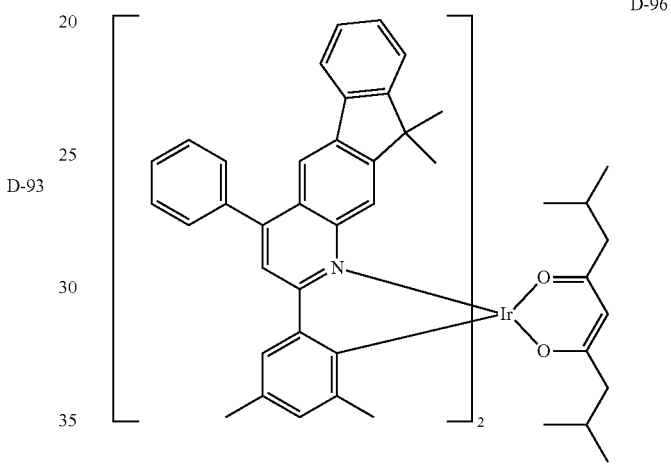
D-96
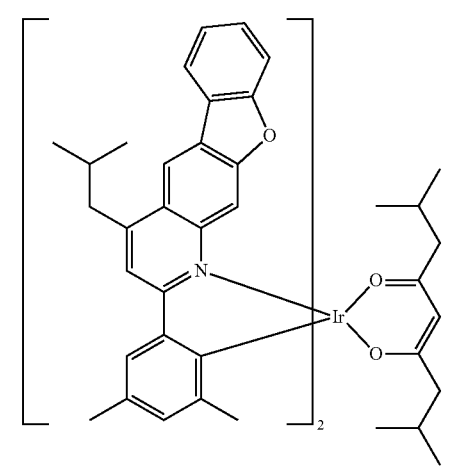
D-94
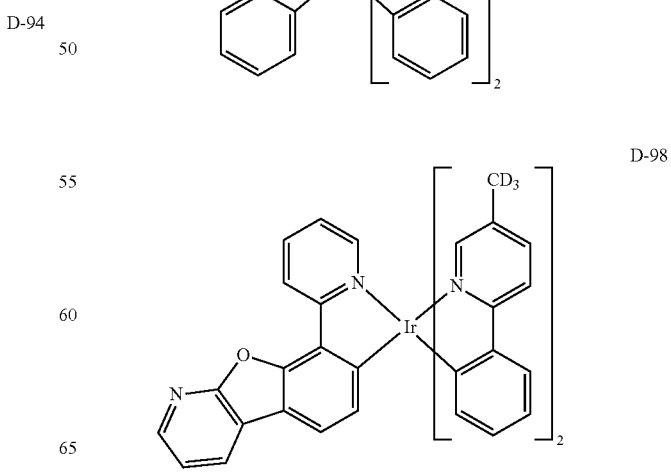
D-97
D-98

D-99
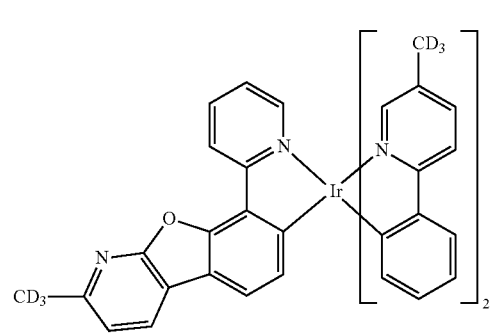
D-100
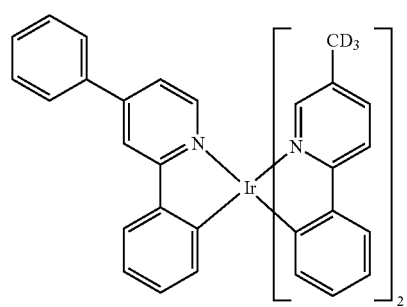
D-101
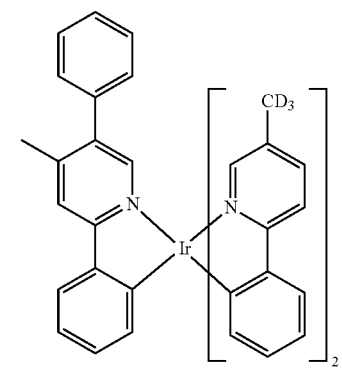
D-102
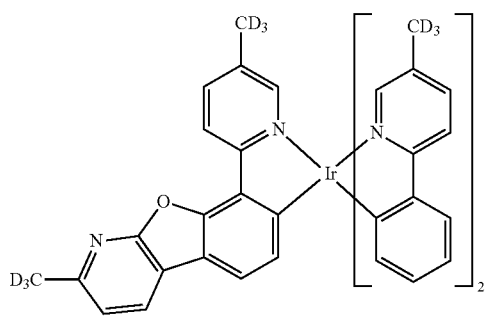
D-103
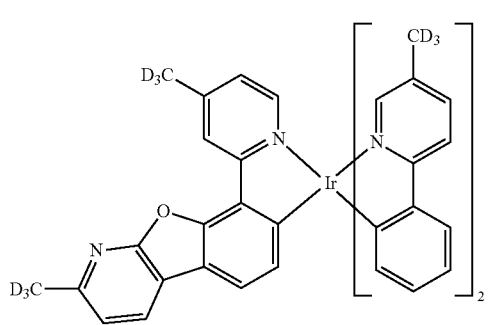
D-104
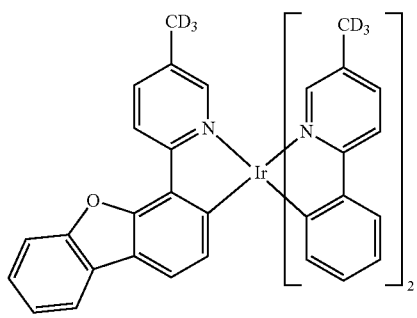
D-105
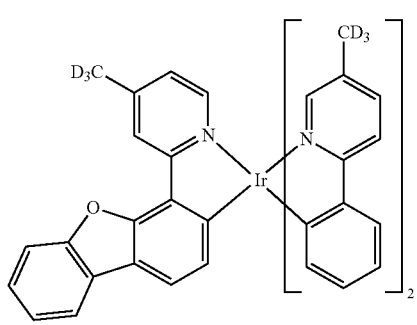
D-106
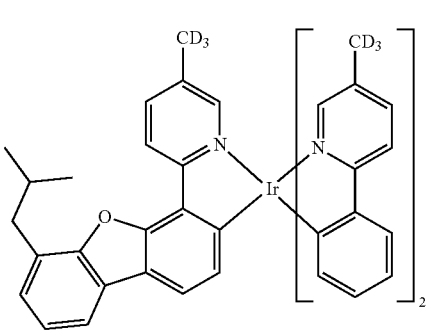
D-107
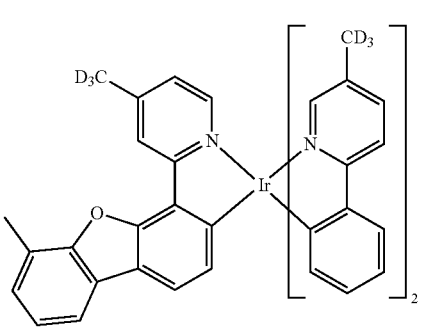
D-108
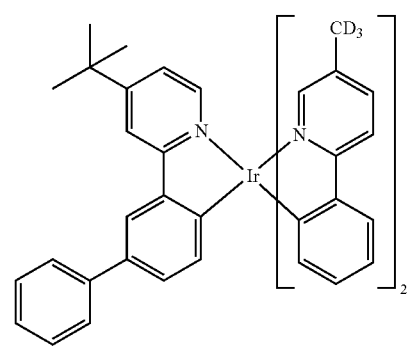

D-109
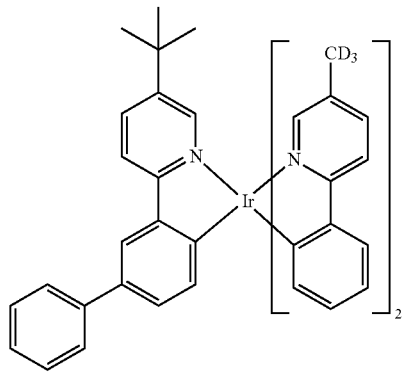
D-110
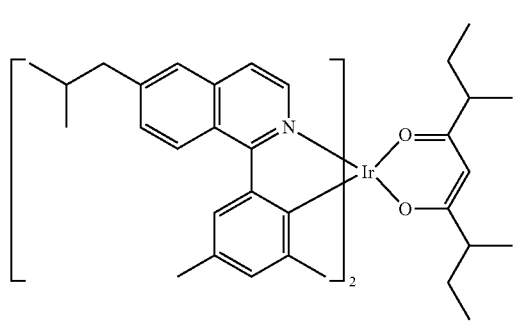
D-111
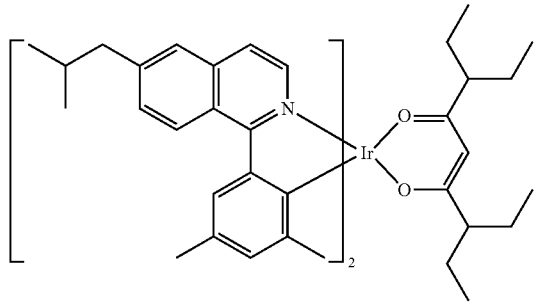
D-112
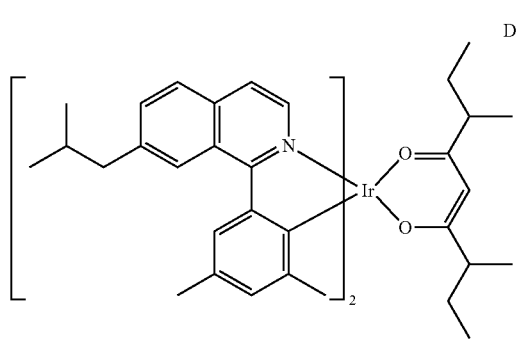
D-113
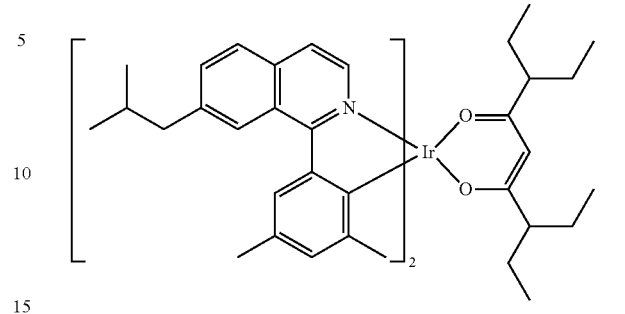
D-114
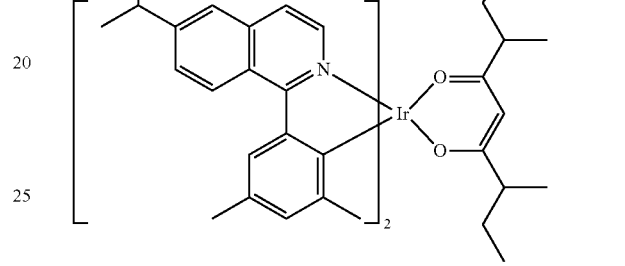
D-115
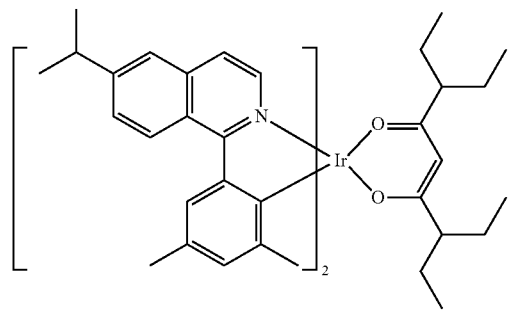
D-116
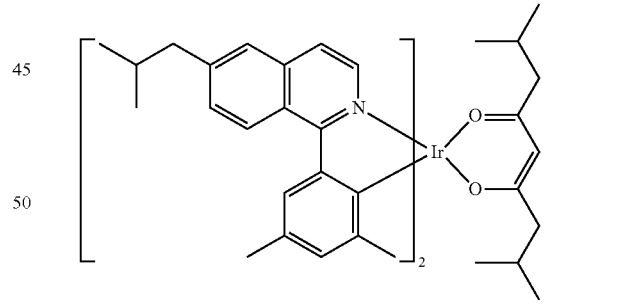
D-117
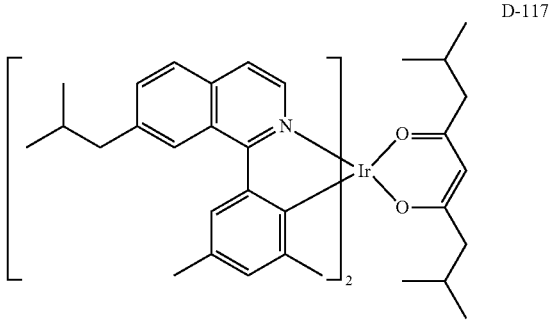

D-118
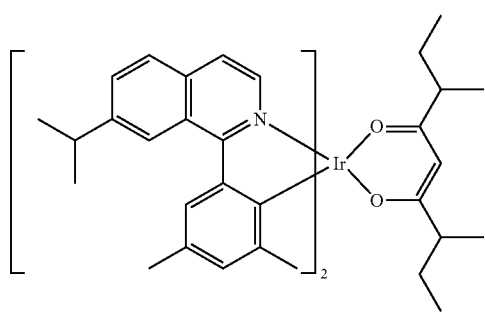
D-119
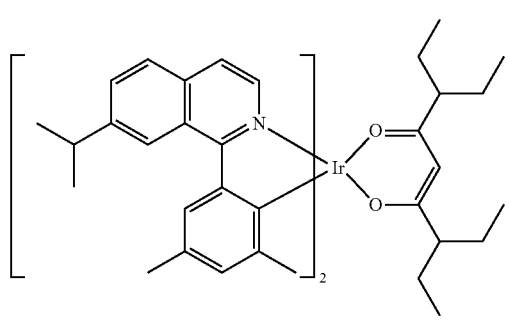
D-120
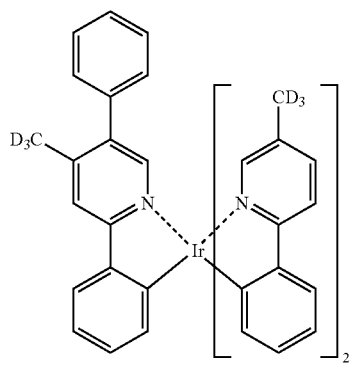
D-121
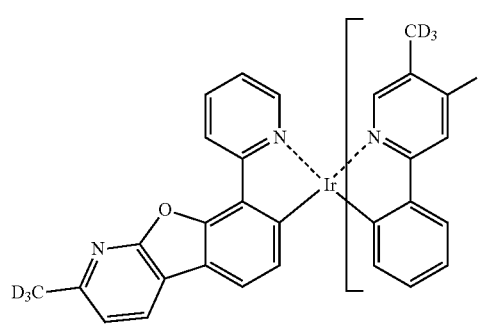
D-122
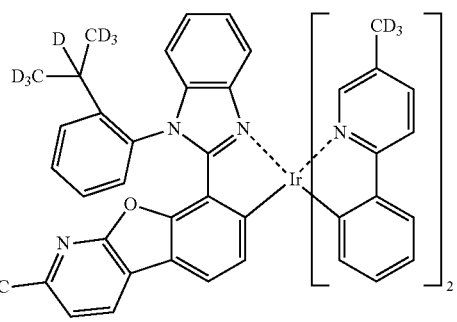
D-123
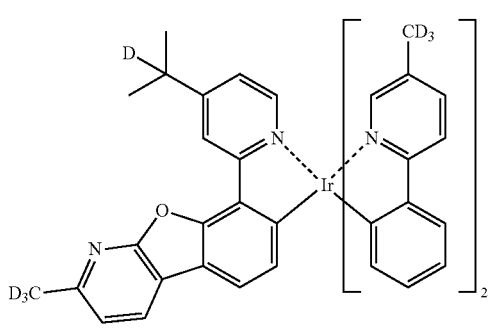
D-124
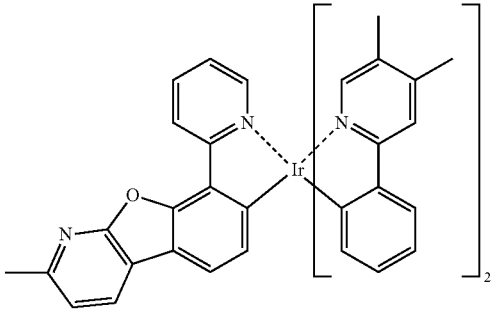
D-125
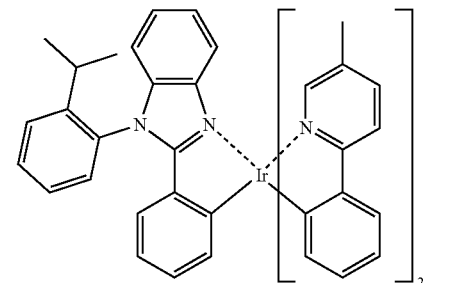
D-126
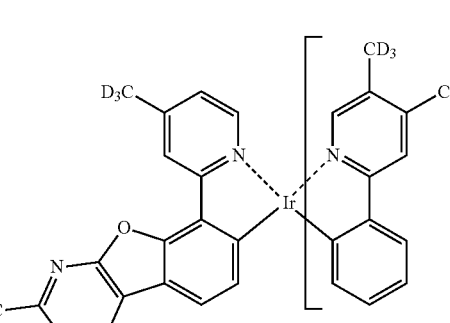

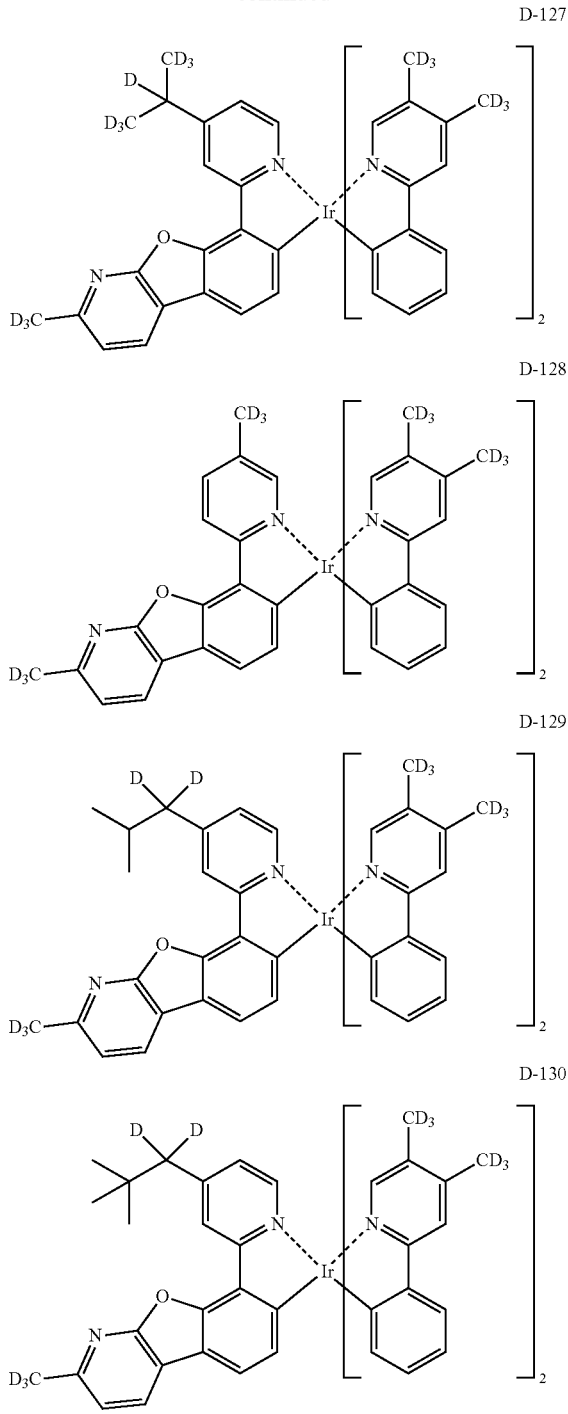

In another embodiment of the present disclosure, a composition for preparing an organic electroluminescent device is provided. The composition is preferably for preparing a hole transport layer, a hole auxiliary layer, or a light-emitting auxiliary layer of an organic electroluminescent device and comprises the compound of the present disclosure. When there are two or more hole transport layers, the compound of the present disclosure may be comprised in the composition for preparing a hole transport layer (hole auxiliary layer) adjacent to the light-emitting layer.

In addition, the organic electroluminescent device according to the present disclosure comprises a first electrode; a second electrode; and at least one organic layer between the first and second electrodes. The organic layer comprises a hole transport layer, a hole auxiliary layer, or a light-emitting auxiliary layer, and the hole transport layer, the hole auxiliary layer, or the light-emitting auxiliary layer may comprise the composition for preparing the organic electroluminescent device according to the present disclosure.

The organic electroluminescent device according to the present disclosure may further comprise, in addition to the organic electroluminescent compound represented by formula 1, at least one compound selected from the group consisting of arylamine-based compounds and styrylarylamine-based compounds.

In the organic electroluminescent device of the present disclosure, the organic layer may further comprise, besides the organic electroluminescent compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x$ ($1 \leq X \leq 2$), $AlO_x$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

Herein, the hole auxiliary layer or the light-emitting auxiliary layer is placed between the hole transport layer and the light-emitting layer, and may be used for controlling the hole transport speed. The hole auxiliary layer or the light-emitting auxiliary layer may provide an effect of improving the efficiency and lifespan of the organic electroluminescent device.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers and emitting white light.

In addition, the organic electroluminescent compound or the plurality of host materials according to the present disclosure can also be used in an organic electroluminescent device comprising a quantum dot (QD).

In order to form each layer constituting the organic EL device of the present disclosure, dry film-forming methods such as vacuum deposition, sputtering, plasma, ion plating methods, etc., or wet film-forming methods such as ink jet printing, spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure. However, the present disclosure is not limited by the following examples.

Example 1: Preparation of Compound C-109

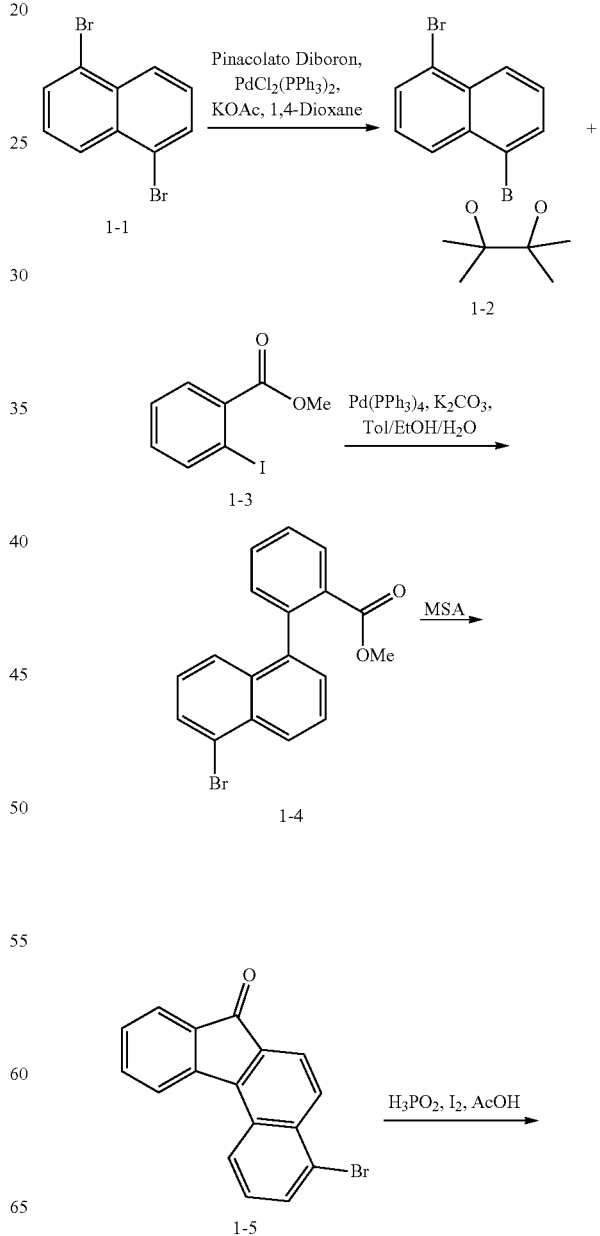

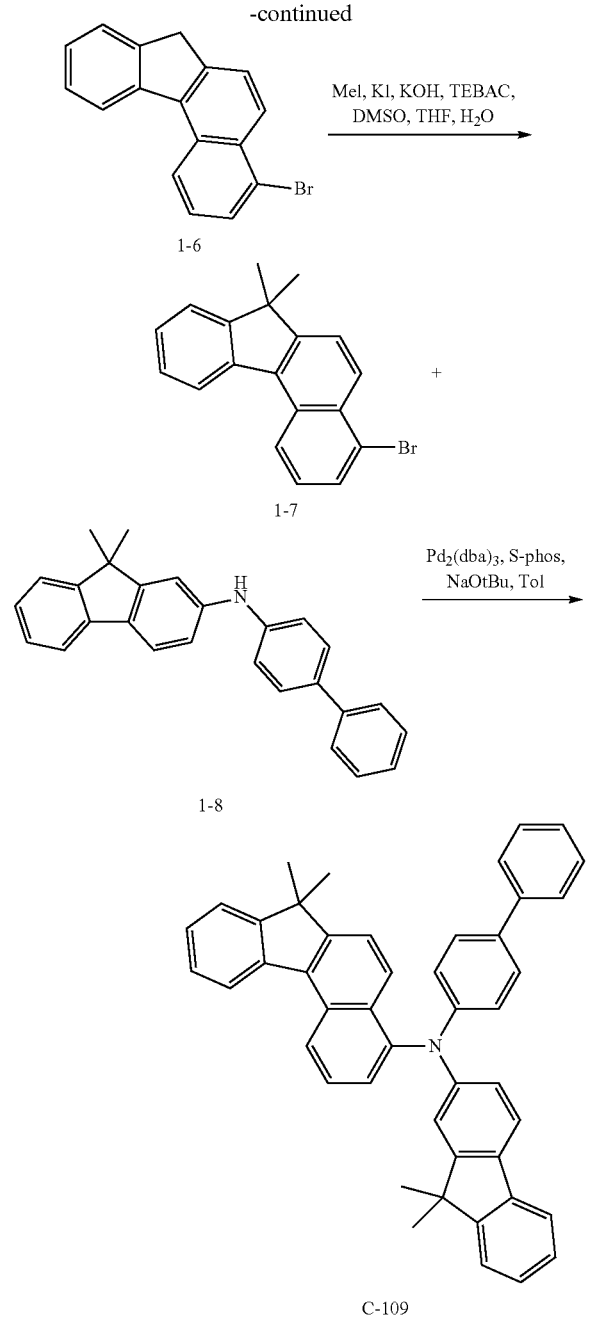

Preparation of Compound 1-2

99.0 g of compound 1-1 (346.5 mmol), 88.0 g of pinacolato diboron (346.5 mmol), 12.1 g of PdCl$_2$(PPh$_3$)$_2$ (17.3 mmol), and 68.0 g of KOAc (693.0 mmol) were dissolved in 1400 mL of 1,4-dioxane in a flask, and the mixture was stirred under reflux for 4 hours. Distilled water was added thereto to complete the reaction, and the mixture was extracted with ethyl acetate (EA)/H$_2$O to obtain 115.0 g of compound 1-2 (yield: 100%).

Preparation of Compound 1-4

115.0 g of compound 1-2 (346.5 mmol), 52.0 mL of compound 1-3 (346.5 mmol), 20.0 g of Pd(PPh$_3$)$_4$ (17.3 mmol), 120.0 g of K$_2$CO$_3$ (866.25 mmol), 1400 mL of toluene, 350 mL of EtOH, and 400 mL of H$_2$O were introduced into a flask and dissolved, and the mixture was stirred under reflux for 5 hours. After completion of the reaction, the mixture was extracted with EA/H$_2$O and separated with column chromatography to obtain 40.5 g of compound 1-4 (yield: 30.8%).

Preparation of Compound 1-5

40.5 g of compound 1-4 (118.7 mmol) and 300 mL of methanesulfonic acid (MSA) were introduced into a flask, and the mixture was stirred at 60° C. for 6 hours. After completion of the reaction, the mixture was added dropwise to H$_2$O, filtered, and separated with column chromatography to obtain 13.6 g of compound 1-5 (yield: 37%).

Preparation of Compound 1-6

9.1 mL of H$_3$PO$_2$ (83.3 mmol), 6.9 g of I$_2$ (27.0 mmol), and 220 mL of AcOH were introduced into a flask and dissolved, and the mixture was stirred under reflux for 1 hour. 16.1 g of compound 1-5 (52.0 mmol) was then added thereto and the mixture was stirred under reflux for 19 hours. After completion of the reaction, the mixture was extracted with EA/H$_2$O and separated with column chromatography to obtain 10.8 g of compound 1-6 (yield: 70%).

Preparation of Compound 1-7

10.8 g of compound 1-6 (36.6 mmol), 608 mg of KI (3.7 mmol), 10.3 g of KOH (183.0 mmol), 417 mg of triethylbenzyl ammoniumchloride (TEBAC) (1.8 mmol), 200 mL of dimethyl sulfoxide (DMSO), 20 mL of H$_2$O, and 40 mL of tetrahydrofuran (THF) were introduced into a flask, and the mixture was stirred at room temperature for 30 minutes. 5.7 mL of MeI (91.5 mmol) was then added thereto and the mixture was stirred at room temperature for 20 hours. After completion of the reaction, the mixture was extracted with methylene chloride (MC)/H$_2$O and separated with column chromatography to obtain 9.5 g of compound 1-7 (yield: 80%).

Preparation of Compound C-109

4.6 g of compound 1-7 (14.2 mmol), 5.4 g of compound 1-8 (14.9 mmol), 650 mg of Pd$_2$(dba)$_3$ (0.71 mmol), 583 mg of 2-dicyclohexylphosphino-2',6'-dimethoxybiphenyl (S-phos) (1.4 mmol), 3.4 g of NaOtBu (35.5 mmol), and 100 mL of toluene were introduced into a flask, and the mixture was stirred under reflux for 1 hour. After completion of the reaction, the mixture was extracted with EA/H$_2$O and separated with column chromatography to obtain 6.7 g of compound C-109 (yield: 78%).

| Compound | MW | M.P. |
|---|---|---|
| C-109 | 603.81 | 158° C. |

Device Example 1: Production of an OLED Comprising the Organic Electroluminescent Compound According to the Present Disclosure An OLED comprising the organic electroluminescent compound of the present disclosure was produced as follows. A transparent electrode indium tin oxide (ITO) thin film (10 Ω/sq) on a glass substrate for an organic light-emitting diode (OLED) device (Geomatec, Japan) was subjected to an ultrasonic washing with acetone and isopropyl alcohol, sequentially, and was then stored in isopropyl alcohol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound C-109 was introduced into another cell of said vacuum vapor depositing apparatus, and was evaporated by applying an electric current to the cell, thereby forming a second hole transport layer (auxiliary layer) having a thickness of 60 nm on the first hole transport layer. After forming the hole injection layers and the hole transport layers, a light-emitting layer was then deposited as follows. Compound H-1 was introduced into one cell of the vacuum vapor depositing apparatus as a host of the light-emitting layer, and compound D-39 was introduced into another cell as a dopant. The two materials were evaporated and were deposited in a doping amount of 2 wt % (the amount of dopant) based on the total amount of the host and dopant to form a light-emitting layer having a thickness of 40 nm on the second hole transport layer. Compound ET-1 and compound EI-1 were then introduced into another two cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED was produced.

Comparative Example 1: Production of an OLED Comprising a Conventional Compound as a Second Hole Transport Material An OLED was produced in the same manner as in Device Example 1, except for using compound T-1 for the second hole transport material.

The driving voltage, luminous efficiency, and CIE color coordinate at a luminance of 1,000 nit, and the time taken for the luminance to decrease from 100% to 97% at a luminance of 5,000 nit at a constant current (T97) of the OLEDs produced as above are provided in Table 1 below.

TABLE 1

| | Second Hole Transport Material | Driving Voltage (V) | Luminous Efficiency (cd/A) | CE (x, y) | Lifespan (T97, hr) |
|---|---|---|---|---|---|
| Device Example 1 | C-109 | 2.8 | 25.6 | 0.669 0.331 | 107.3 |
| Comparative Example 1 | T-1 | 3.2 | 14.4 | 0.662 0.335 | 39.9 |

The materials used in Device Example 1 and Comparative Example 1 are as follows:

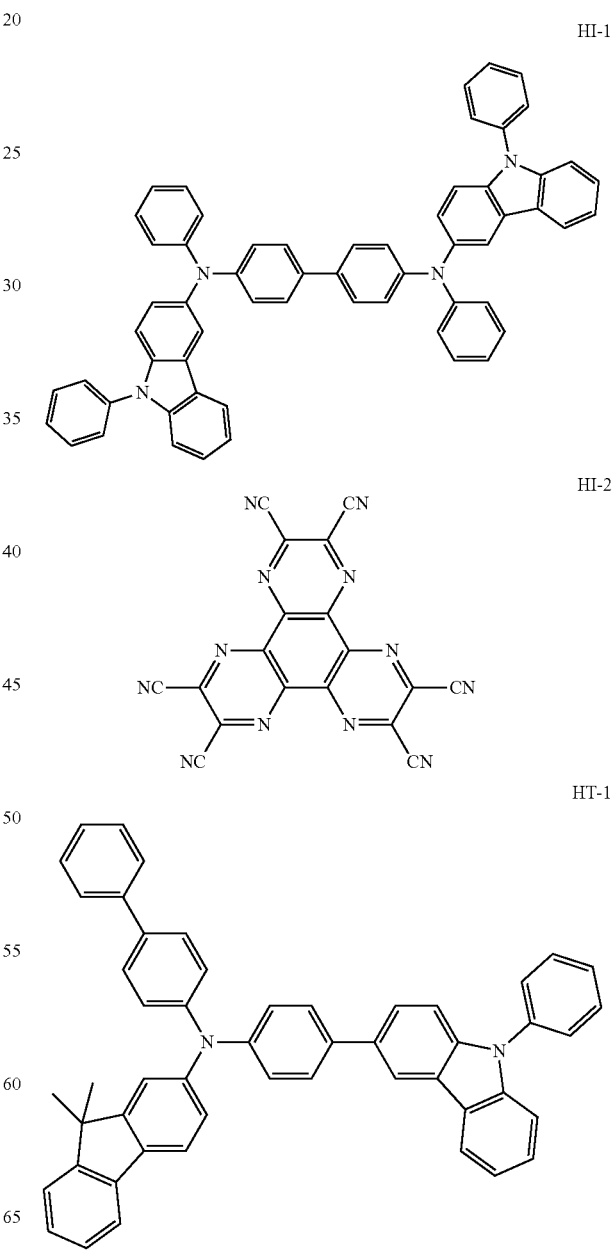

D-39

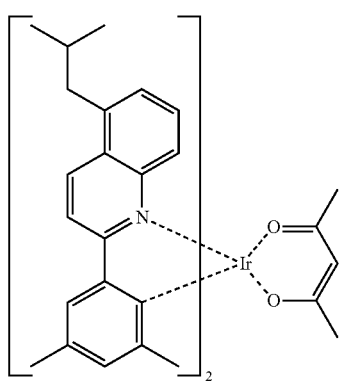

H-1

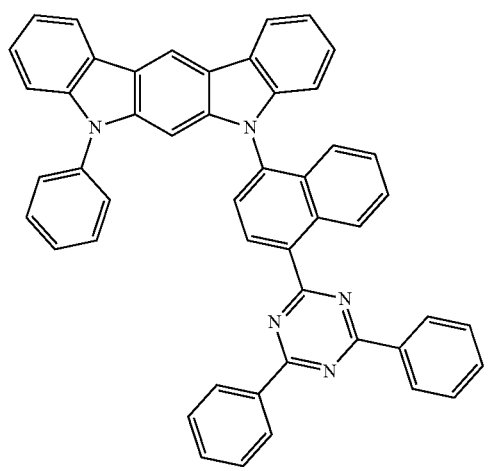

C-109

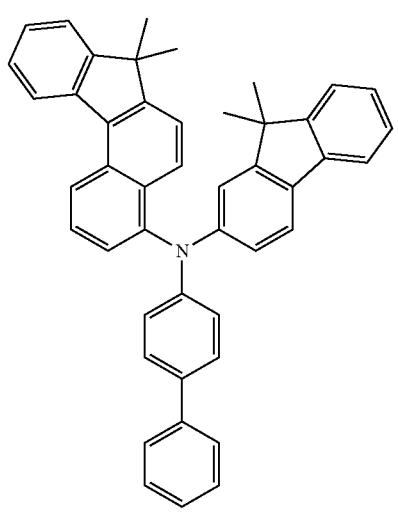

T-1

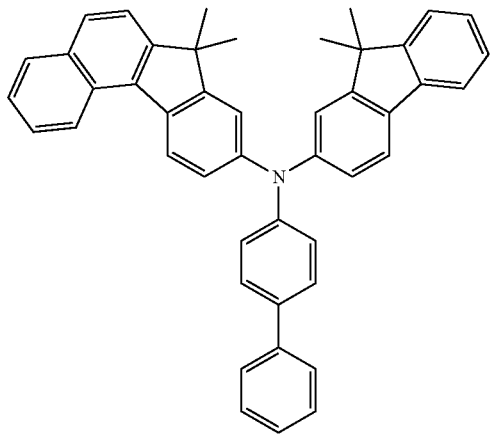

ET-1

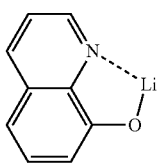

EI-1

As confirmed in Table 1, the organic electroluminescent compound according to the present disclosure showed superior driving voltage, luminous efficiency, and/or lifespan characteristics, compared to the conventional material, when used as a second hole transport material. Particularly, the second hole transport materials used in Device Example 1 and Comparative Example 1 are identical compounds except for the bonding position of the dibenzofluorene with the nitrogen atom, yet such difference occurred.

The invention claimed is:
1. An organic electroluminescent compound represented by the following formula 1:
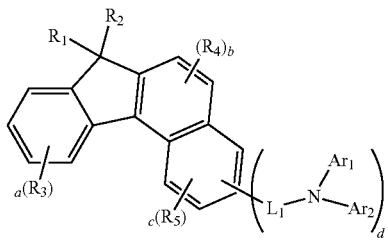
wherein Ar₁ and Ar₂ each independently are selected from the following structures:
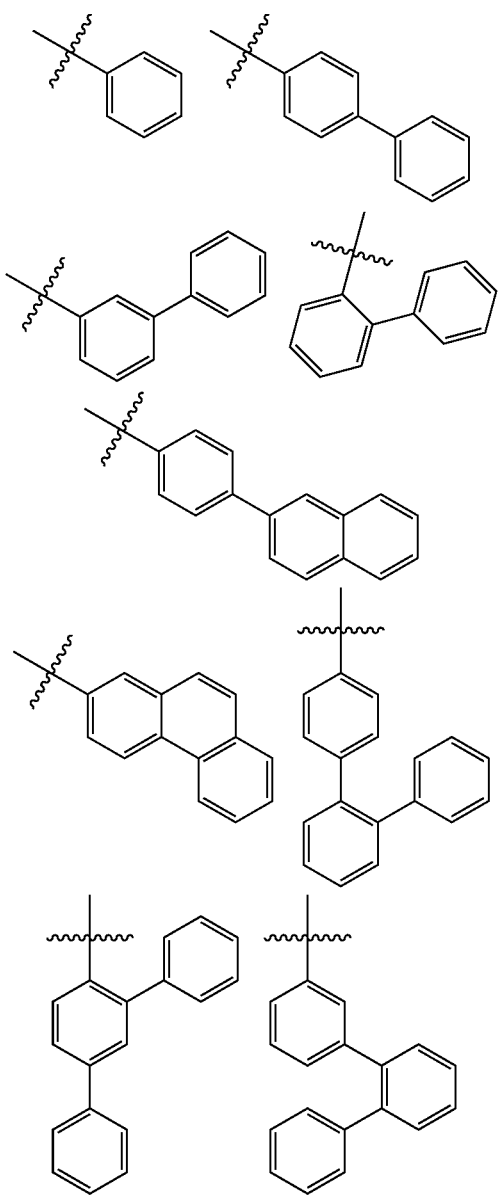
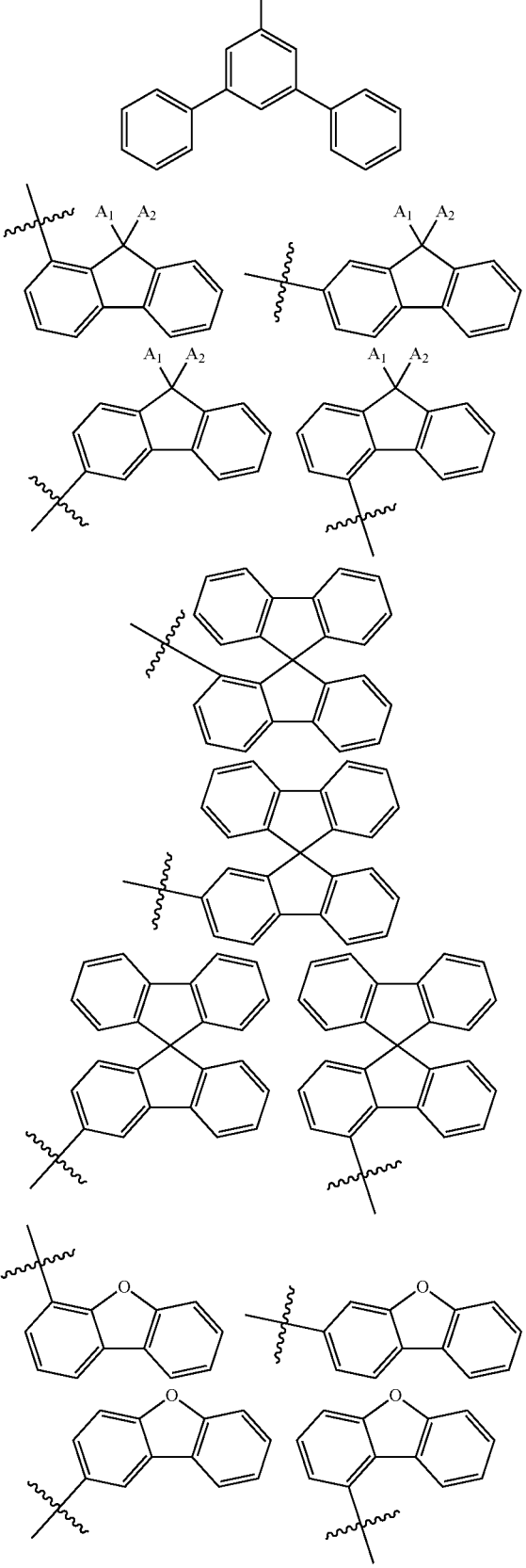

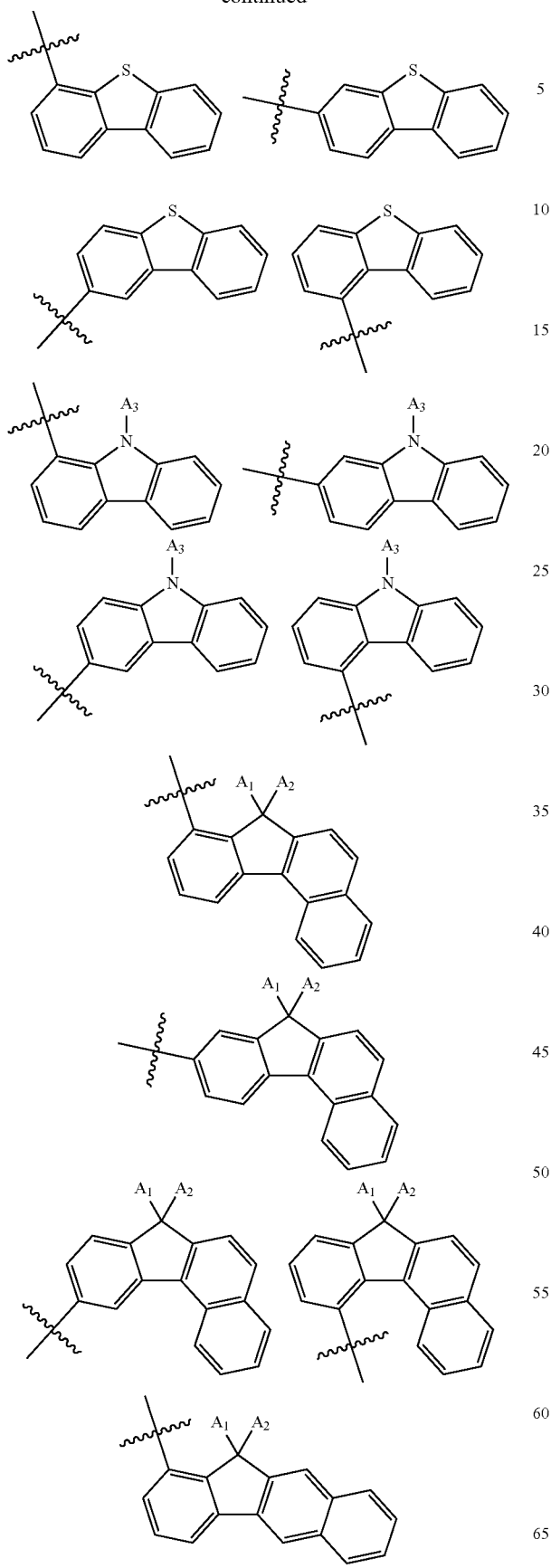
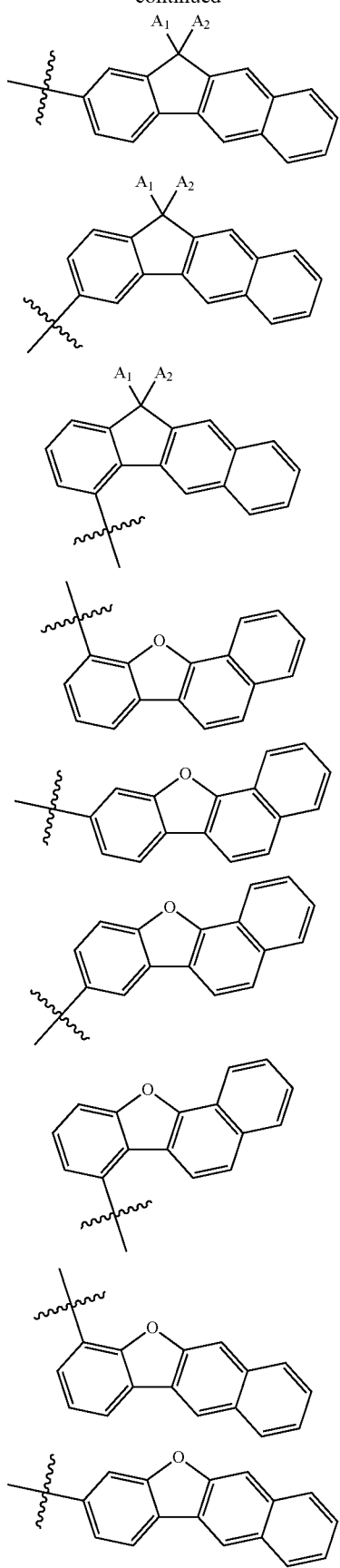

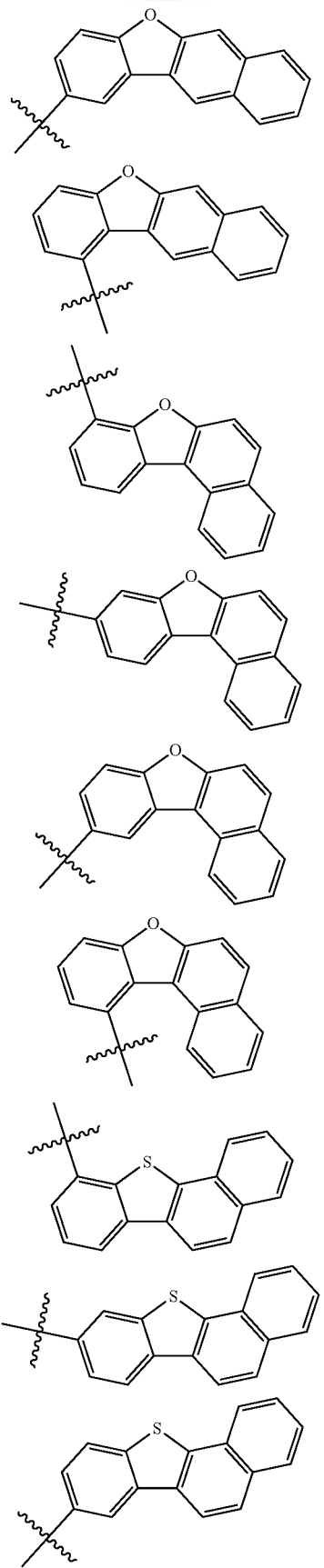

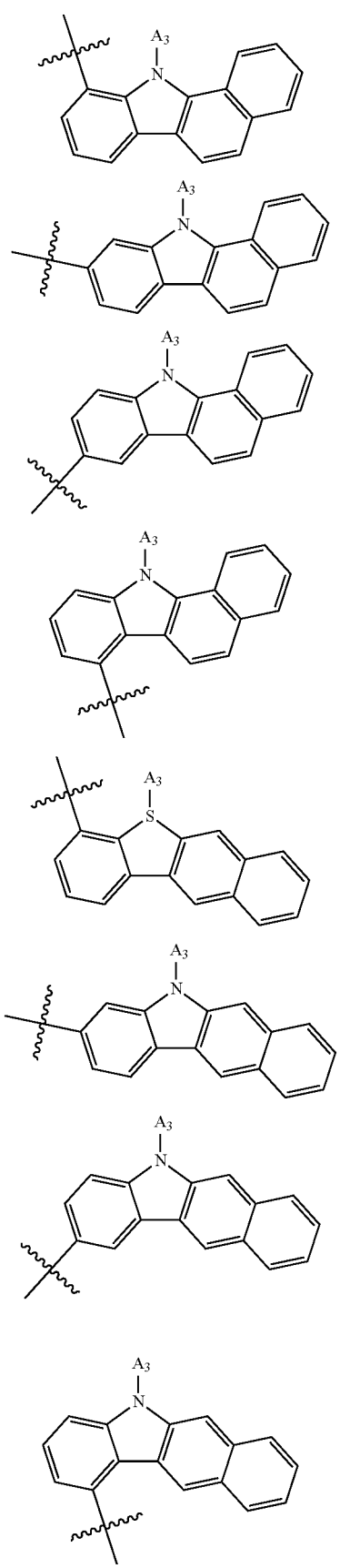
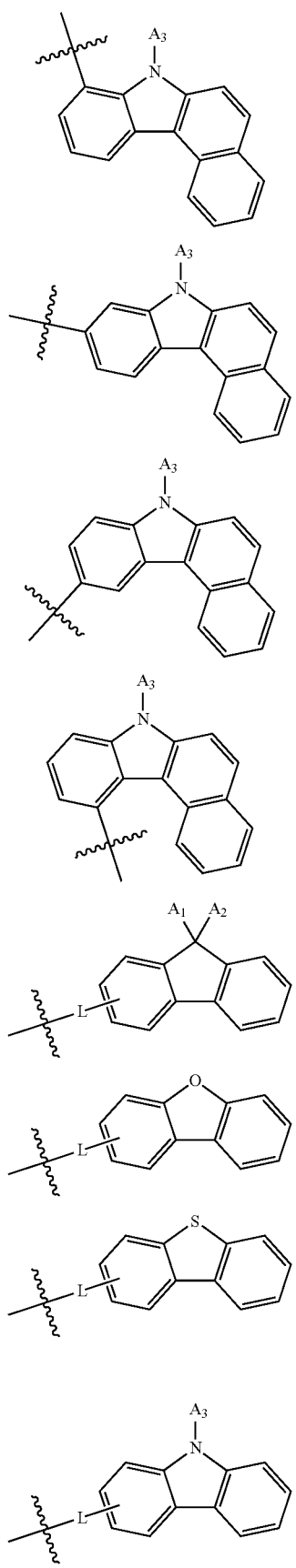

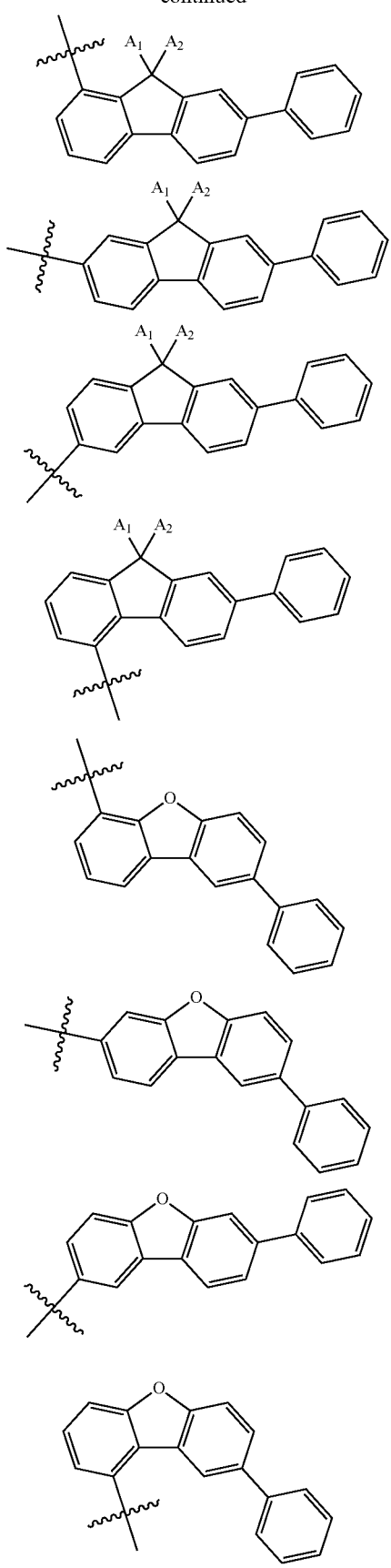
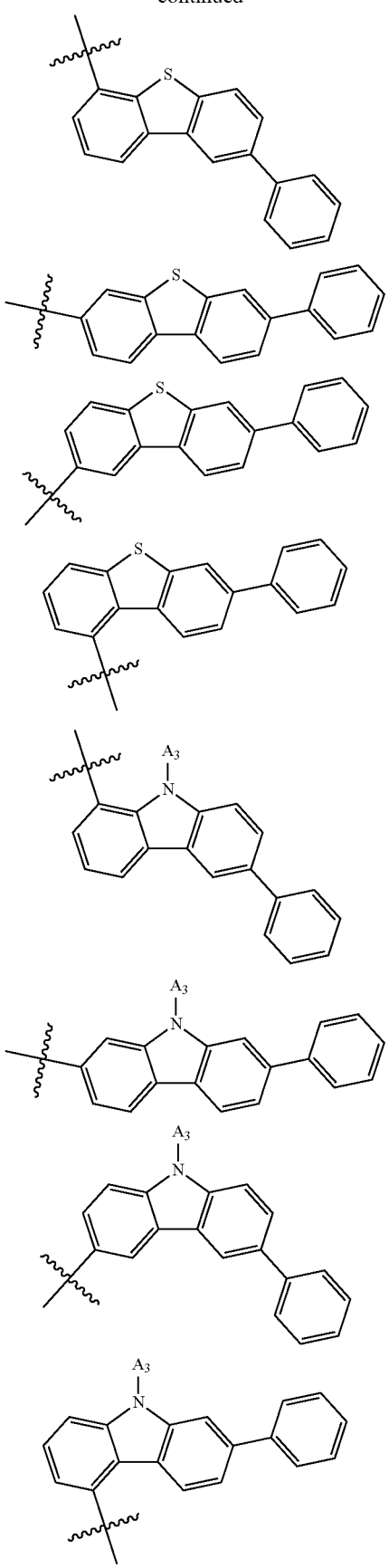

-continued

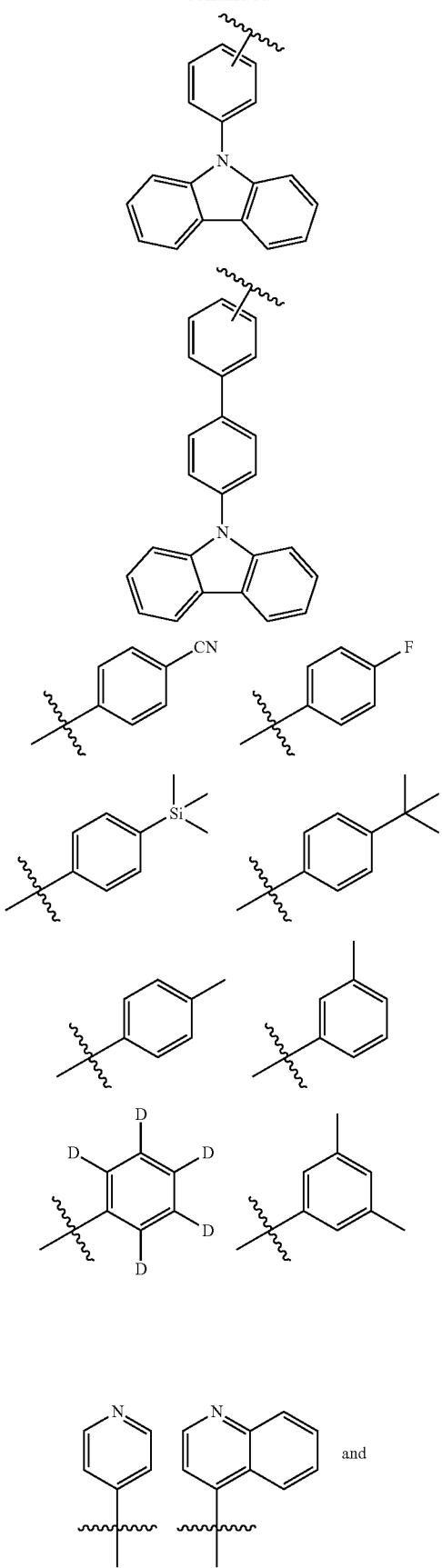

-continued

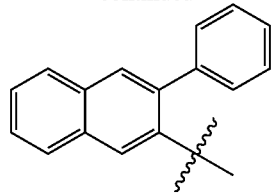

wherein
A₁ to A₃ each independently represent a substituted or unsubstituted (C1-C30)alkyl, a substituted or unsubstituted (C6-C30)aryl, or a substituted or unsubstituted (3- to 30-membered)heteroaryl;
L represents a substituted or unsubstituted (C6-C30) arylene, or a substituted or unsubstituted (3- to 30-membered)heteroarylene,
$L_1$ represents a single bond, an unsubstituted (C6-C30) arylene, or an unsubstituted (3- to 30-membered)heteroarylene, where if a plurality of $L_1$ is present, each of $L_1$ may be the same or different;
$R_1$ and $R_2$ each independently represent a substituted or unsubstituted (C1-C30)alkyl, or a substituted or unsubstituted (3- to 30-membered)heteroaryl;
$R_3$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl;
$R_4$ to $R_5$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino,
where if a plurality of $R_3$ to $R_5$ is present, each of $R_3$, each of $R_4$, and each of $R_5$ may be the same or different; and
a represents an integer of 1 to 4, b represents 1 or 2, c represents an integer of 1 to 3, d represents 1 or 2, and c+d is 4, where if a, b, c, and d each independently are 2 or more, each of $R_3$, each of $R_4$, each of $R_5$, and each of -$L_1$-$NAr_1Ar_2$ may be the same or different.

2. The organic electroluminescent compound according to claim 1, wherein
$L_1$ represents a single bond, an unsubstituted (C6-C12) arylene, or an unsubstituted (5- to 15-membered)heteroarylene;
$R_1$ and $R_2$ each independently represent a substituted or unsubstituted (C1-C6)alkyl; and
$R_3$ to $R_5$ each independently represent hydrogen, or a substituted or unsubstituted (C6-C12)aryl.

3. The organic electroluminescent compound according to claim 1, wherein

L₁ represents a single bond, an unsubstituted (C6-C12) arylene, or an unsubstituted (5- to 15-membered)heteroarylene;

R₁ and R₂ each independently represent an unsubstituted (C1-C6)alkyl; and

R₃ to R₅ each independently represent hydrogen, or an unsubstituted (C6-C12)aryl.

4. An organic electroluminescent compound selected from the following compounds:

C-1
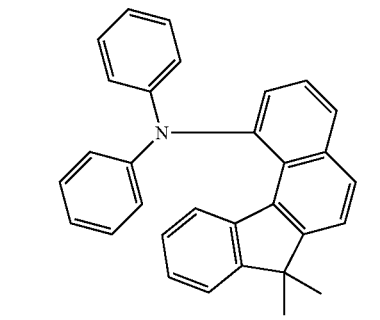

C-2
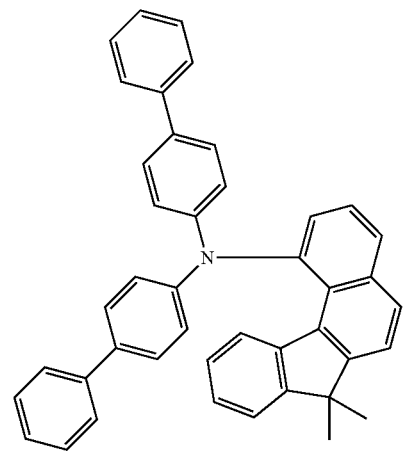

C-3
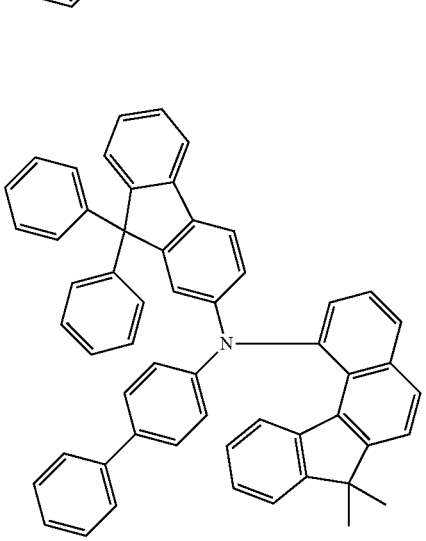

C-4
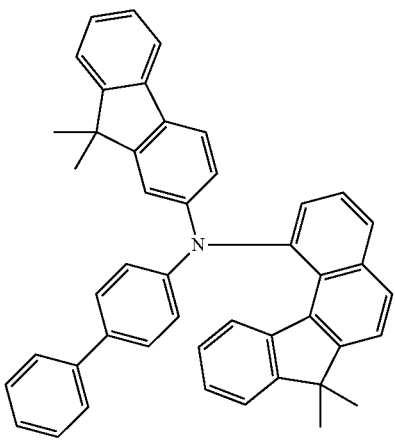

C-5
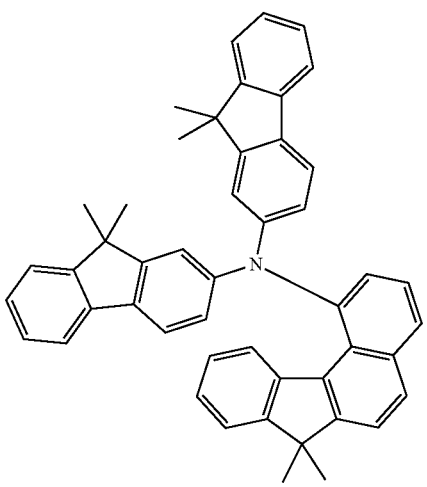

C-6
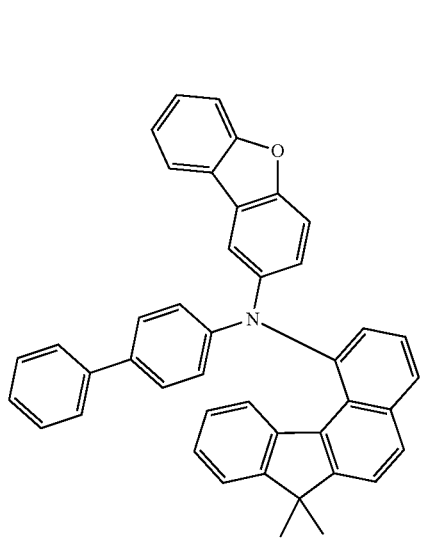

-continued
C-7
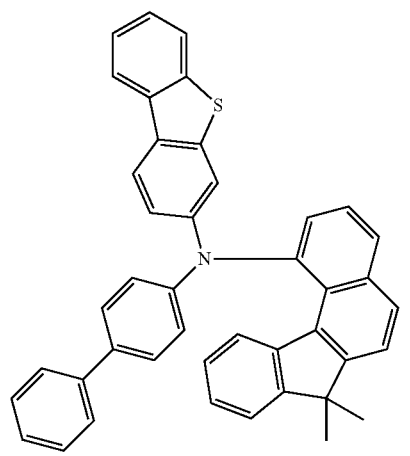
C-8
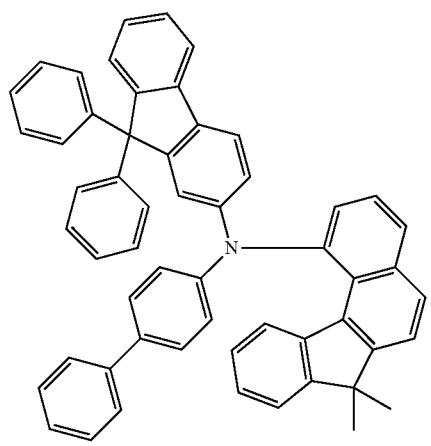
C-9
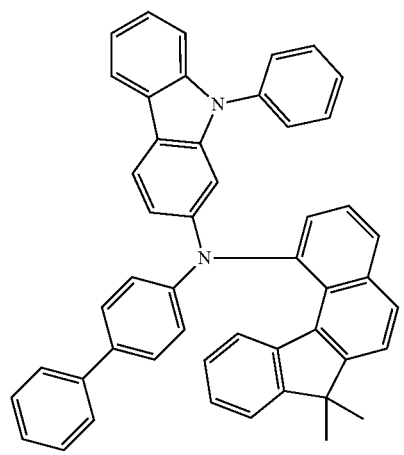
-continued
C-10
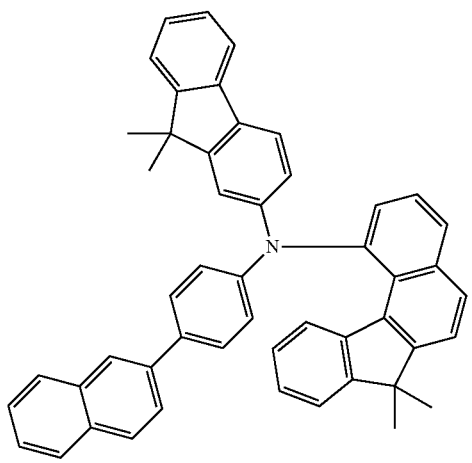
C-11
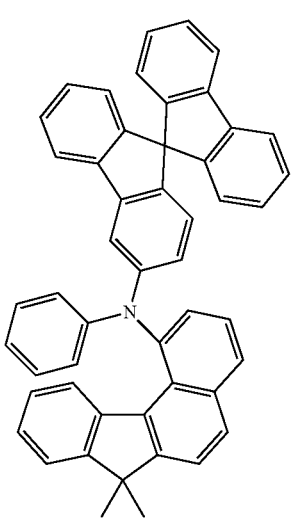
C-12
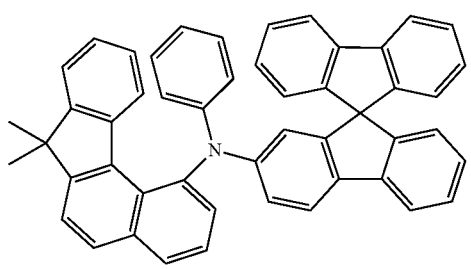
C-13
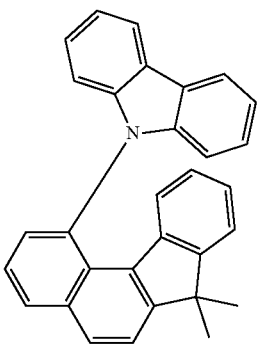

C-14
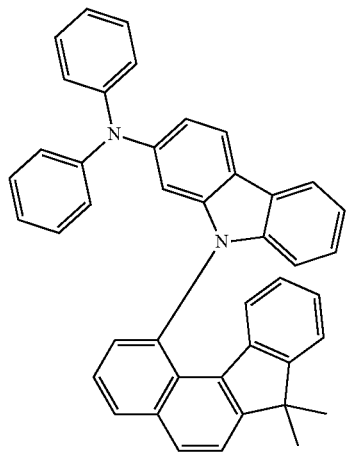
C-19
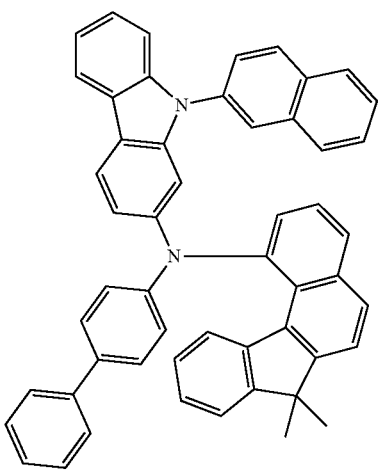
C-16
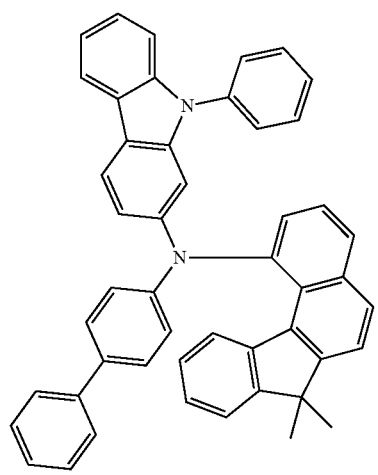
C-21
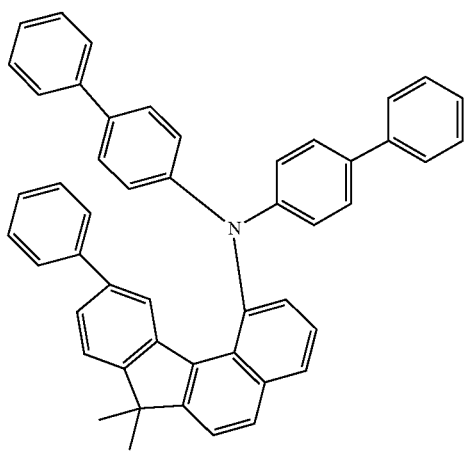
C-18
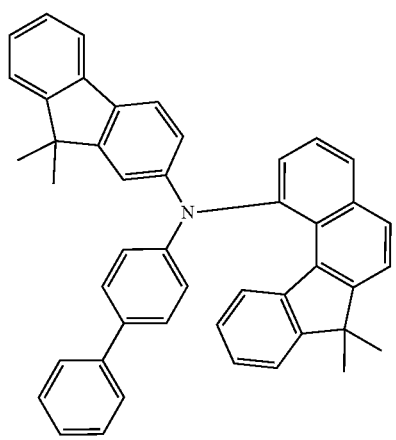
C-22
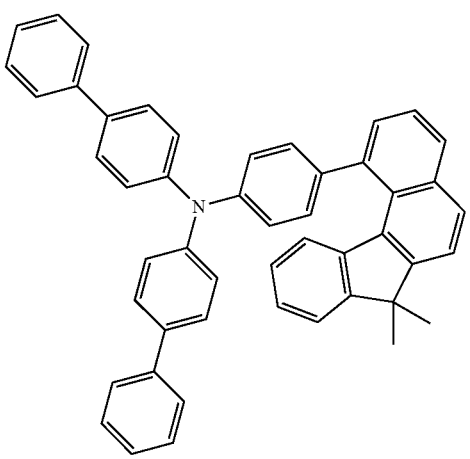

C-23
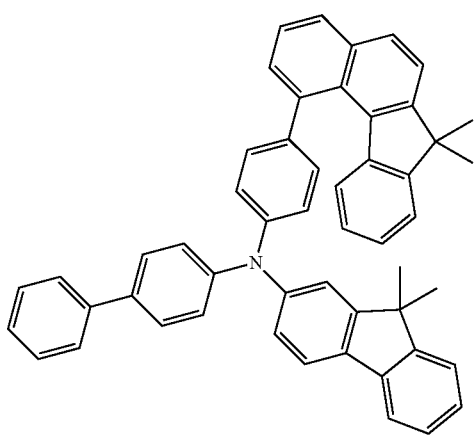
C-26
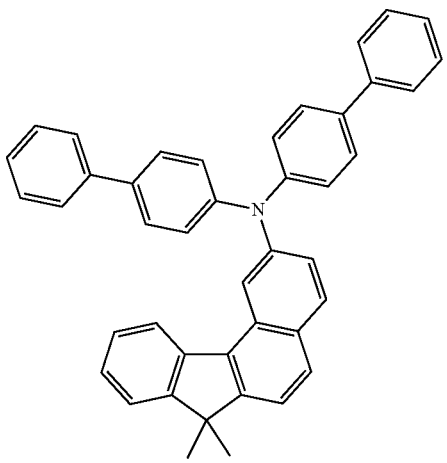
C-24
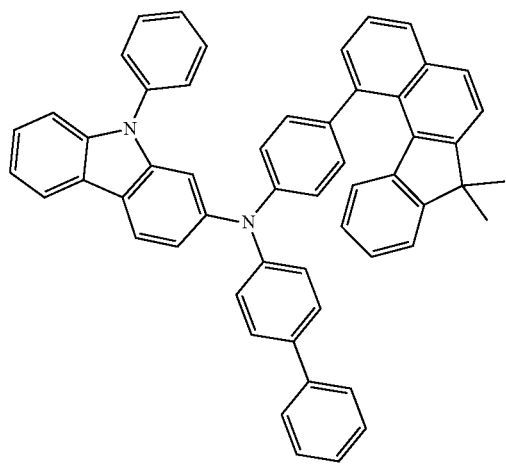
C-27
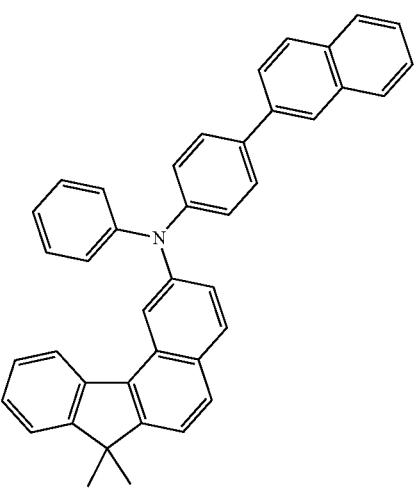
C-25
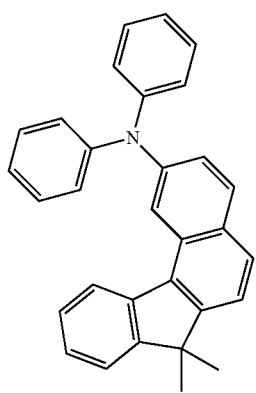
C-28
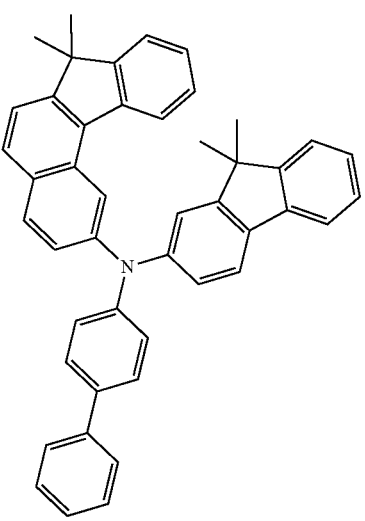

C-29
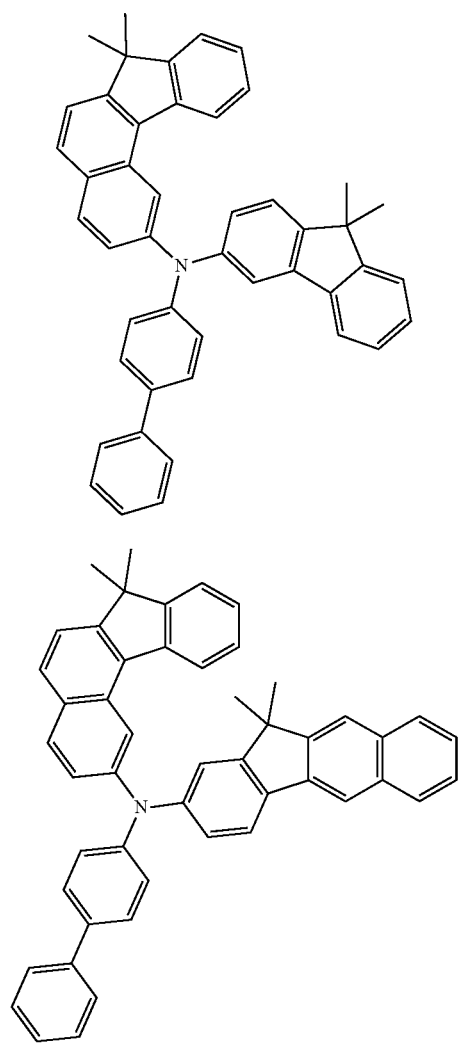
C-32
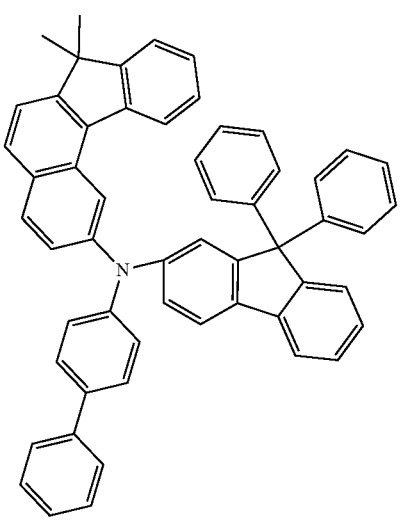
C-30
C-33
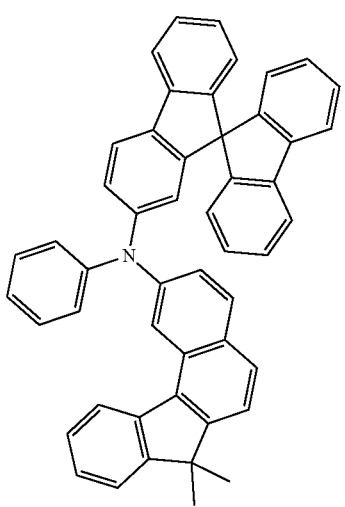
C-31
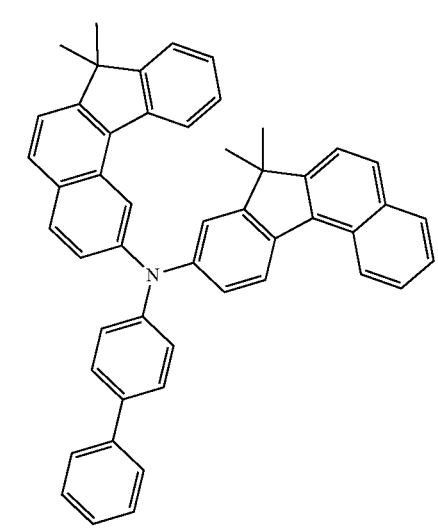
C-34
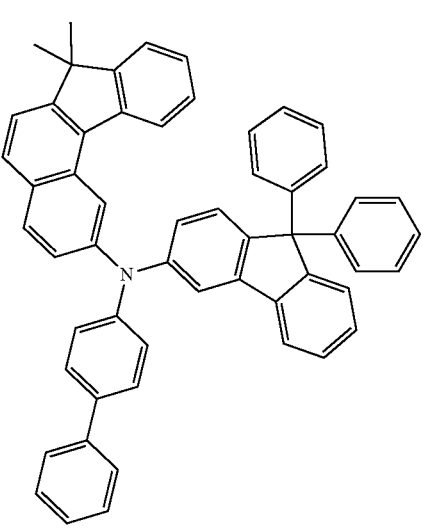

C-35 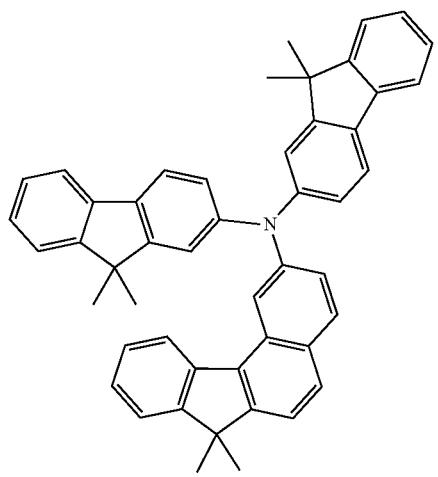
C-38 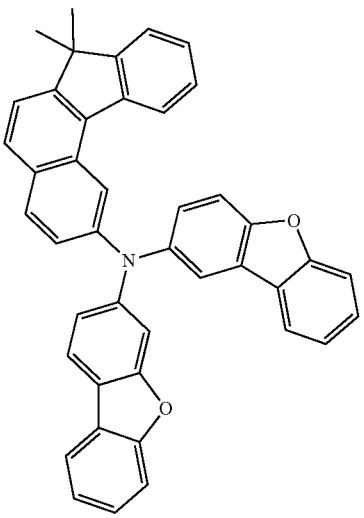
C-36 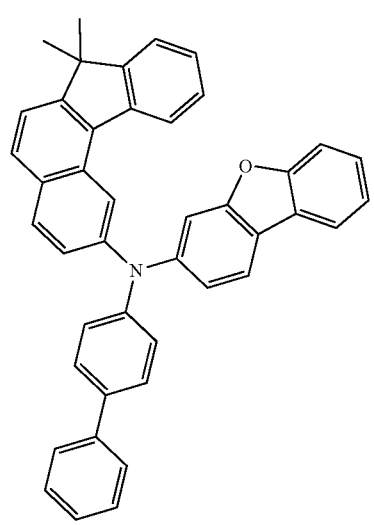
C-39 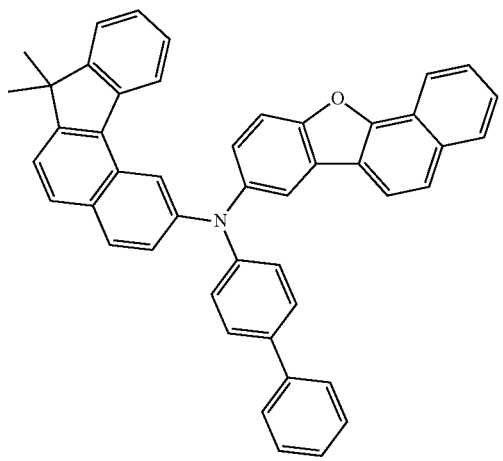
C-37 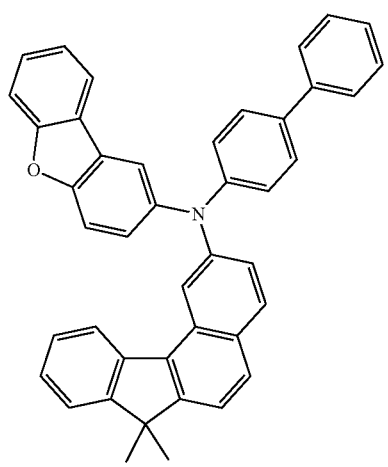
C-40 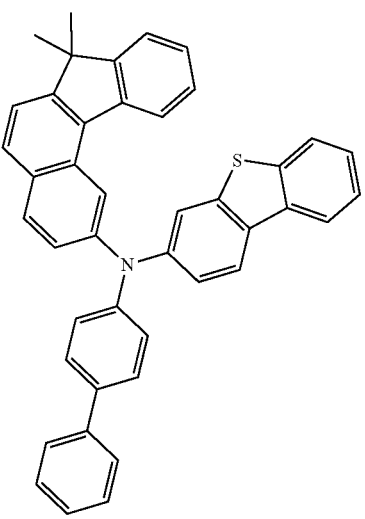

-continued
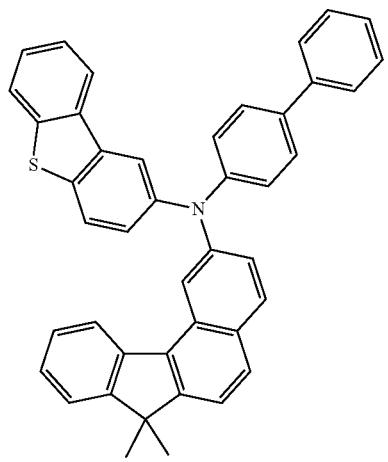
C-41
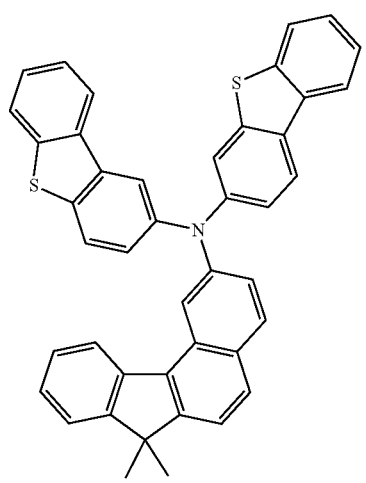
C-42
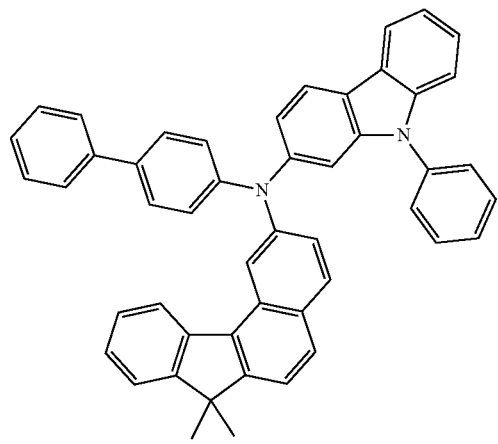
C-43
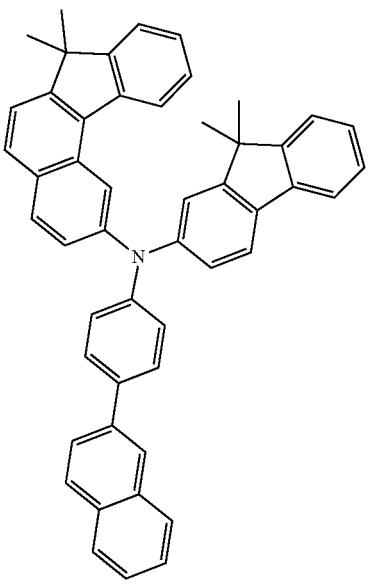
C-44
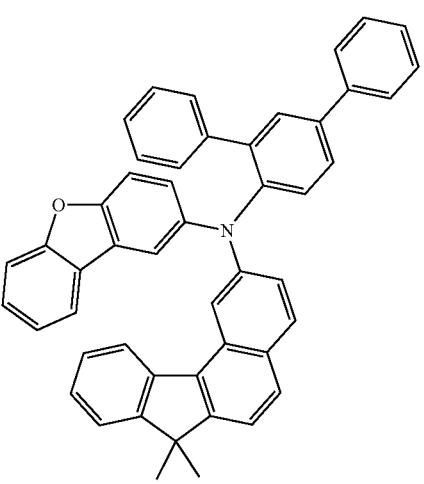
C-45
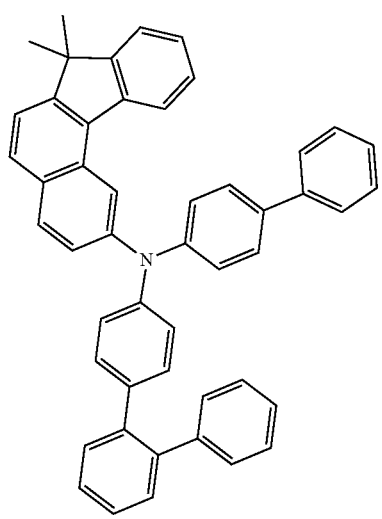
C-46

C-47
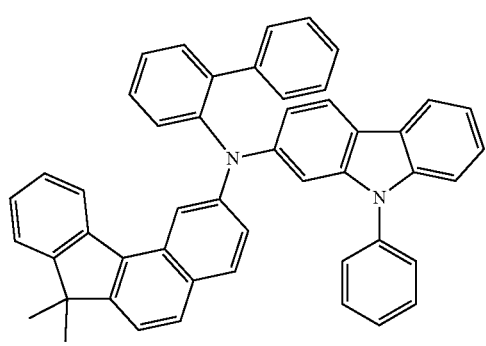
C-48
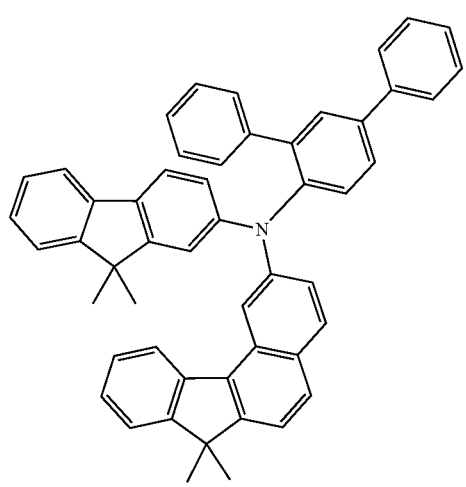
C-49
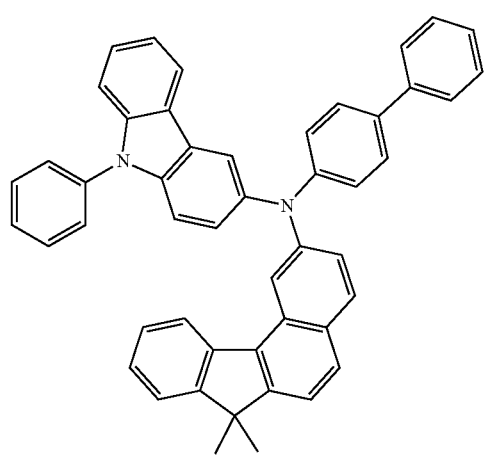
C-51
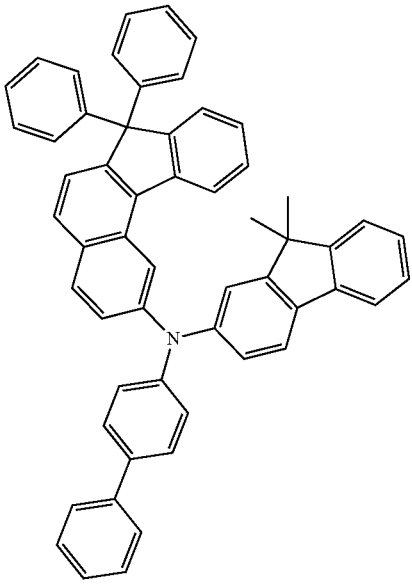
C-52
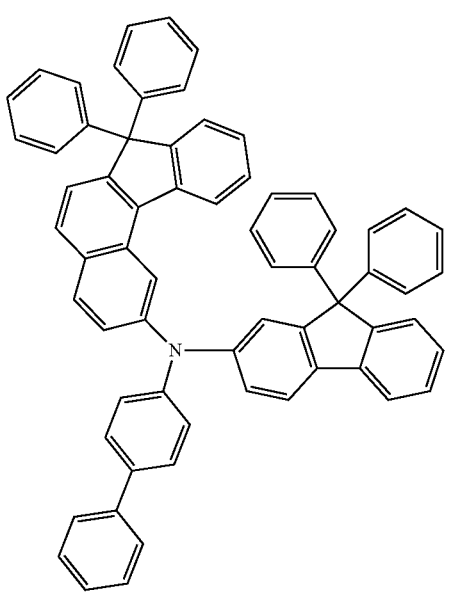
C-53
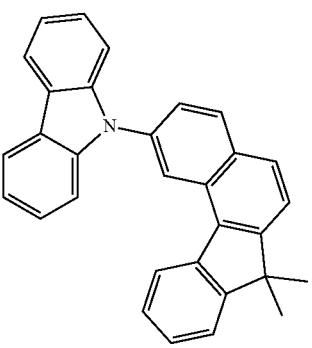

C-54
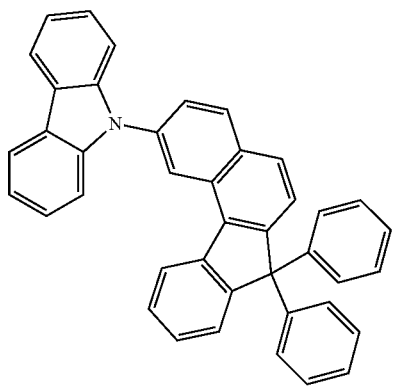
C-55
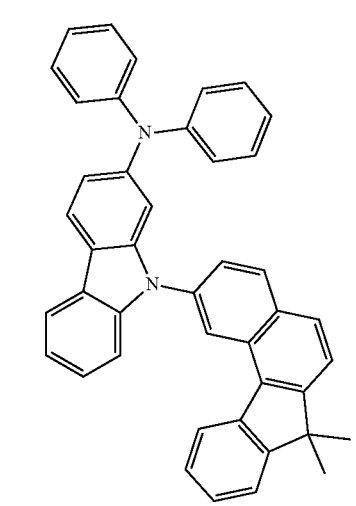
C-53
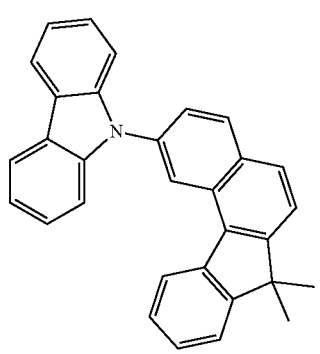
C-55
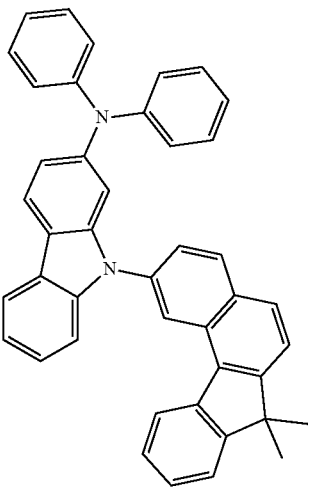
C-60
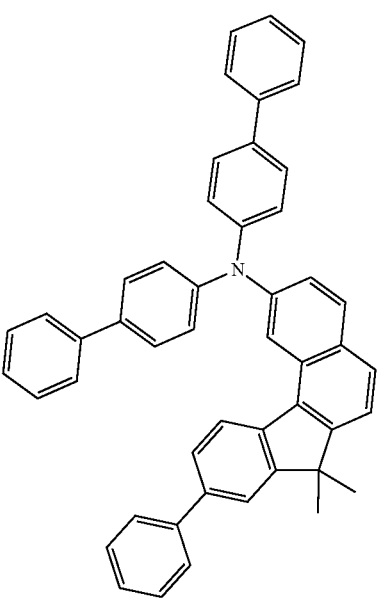
C-61
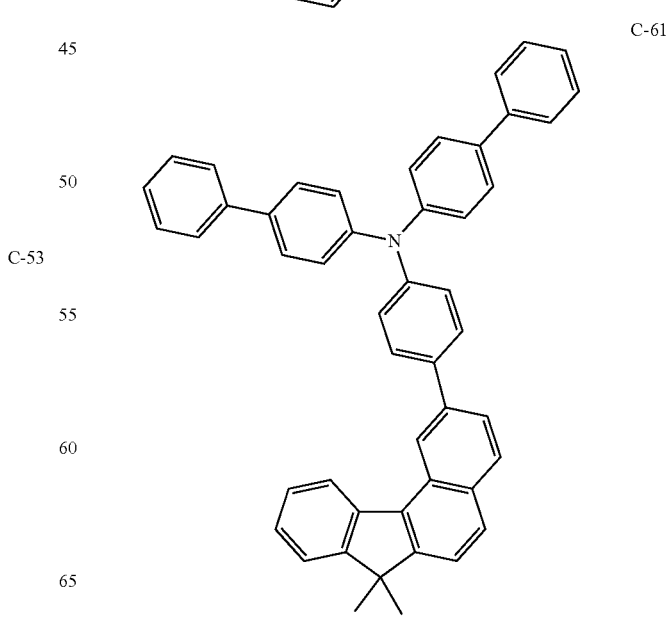

-continued
C-63
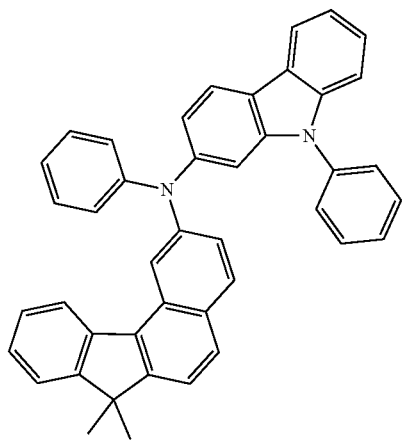
C-64
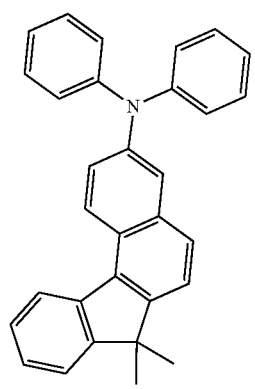
C-65
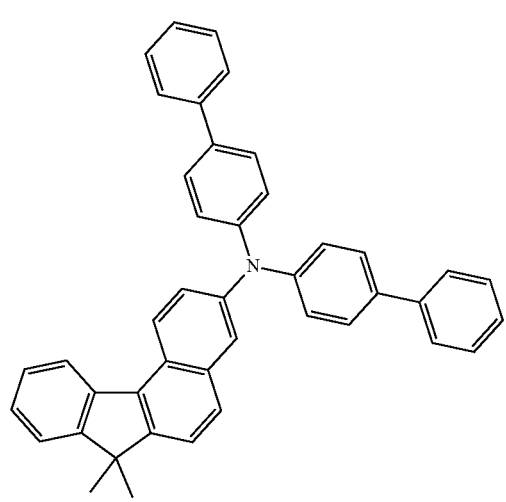
-continued
C-66
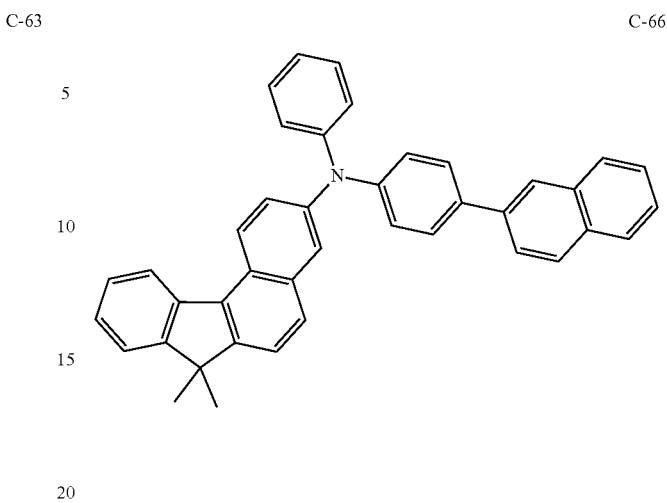
C-67
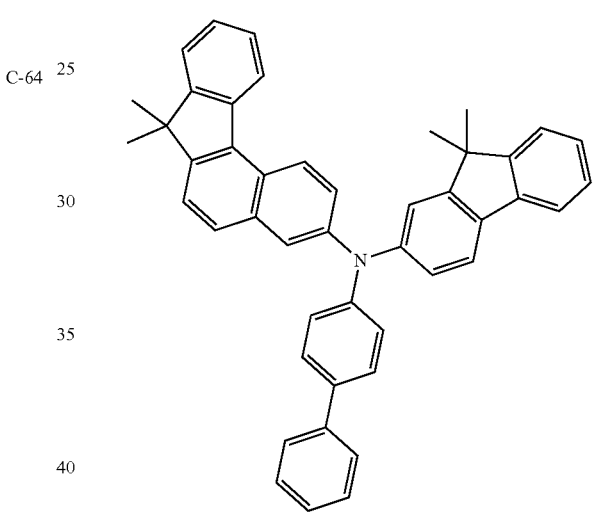
C-68
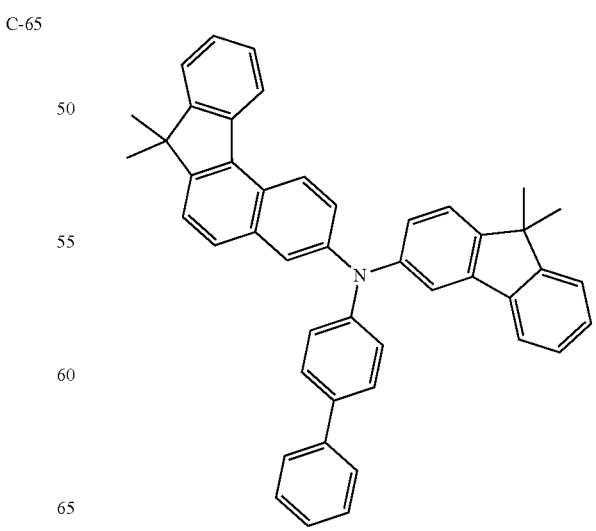

-continued
C-69
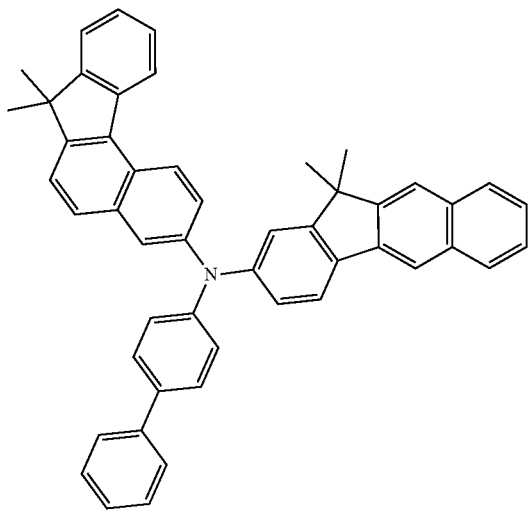
C-70
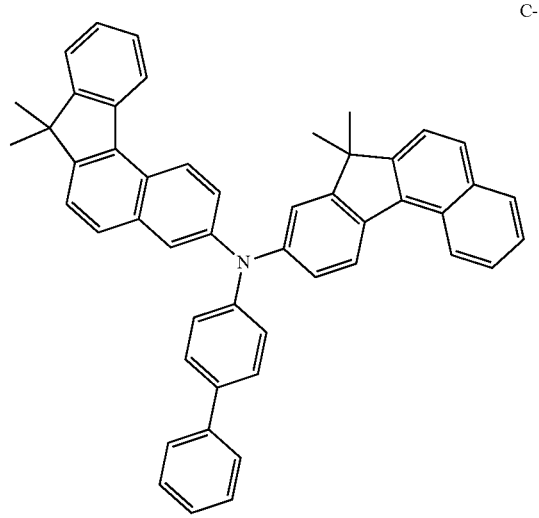
C-71
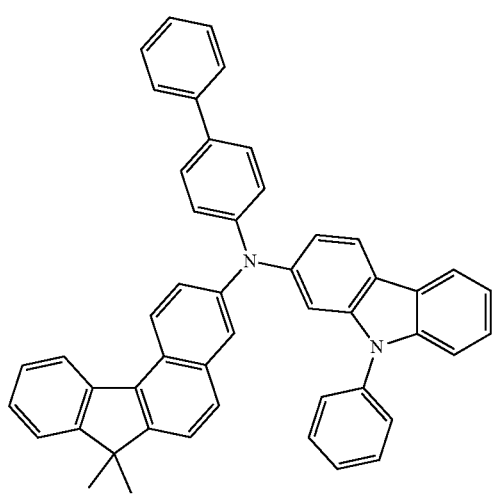
-continued
C-72
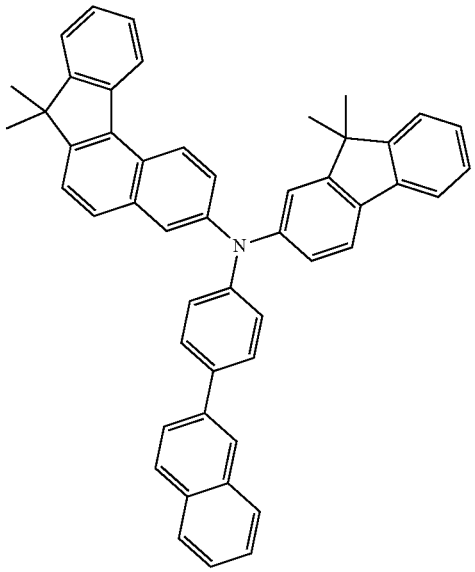
C-73
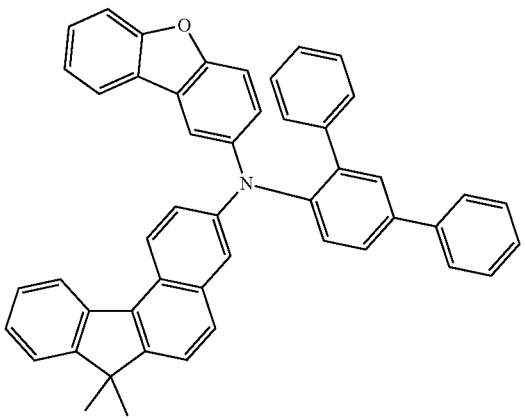
C-74
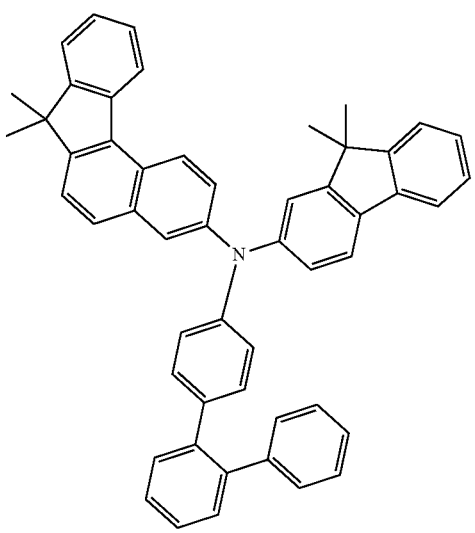

C-75
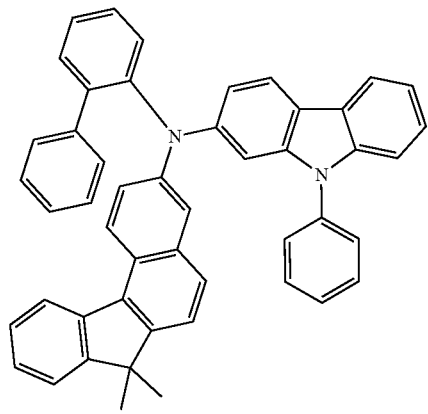
C-80
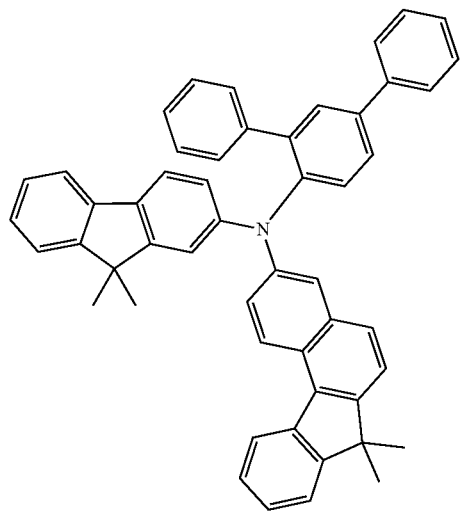
C-76
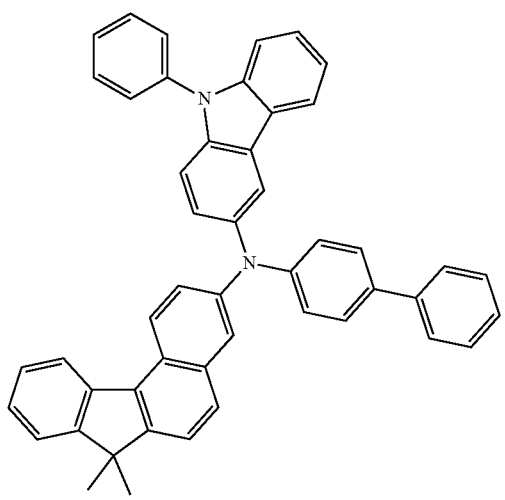
C-85
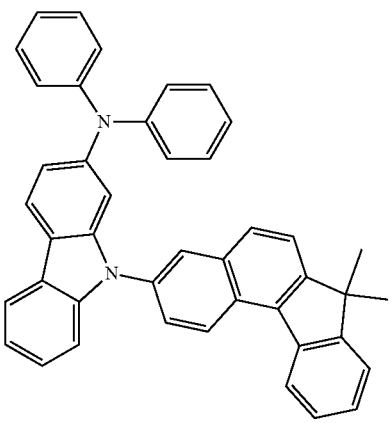
C-79
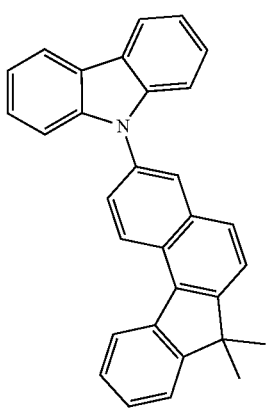
C-86
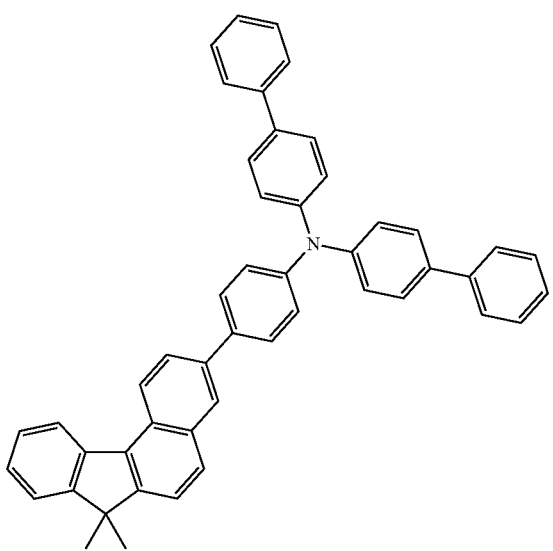

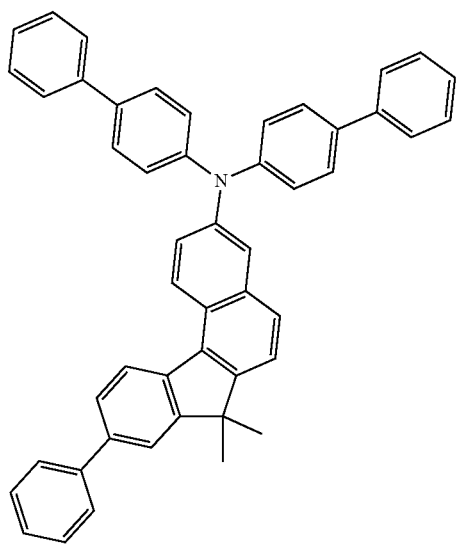
C-90
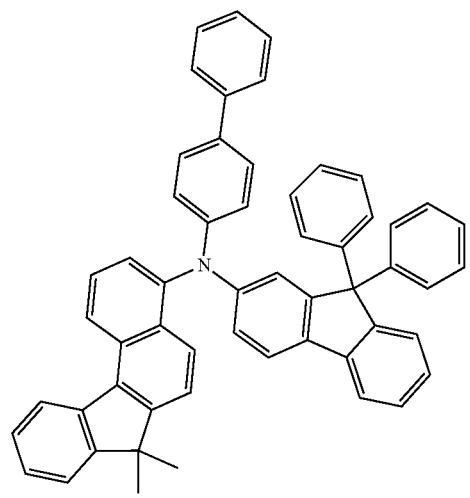
C-93
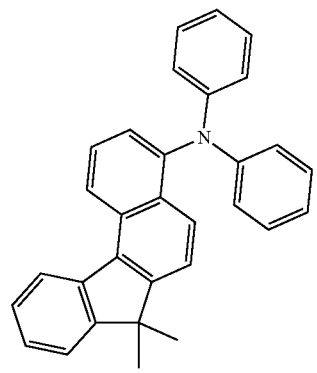
C-91
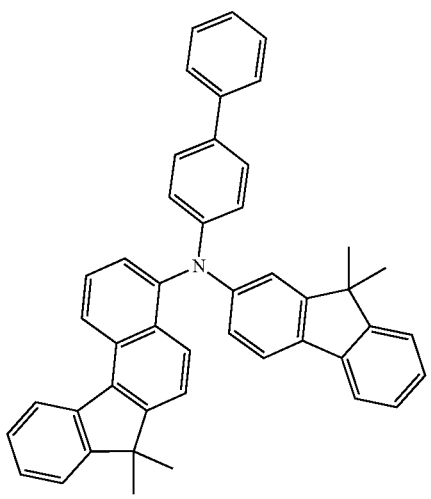
C-94
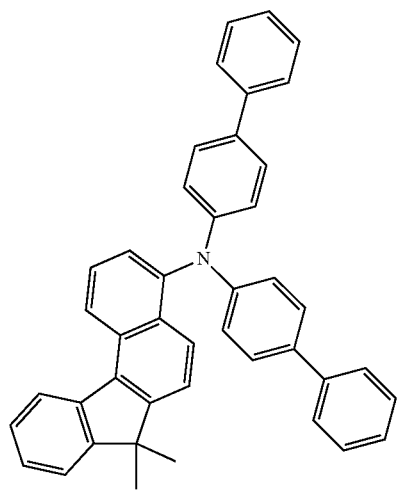
C-92
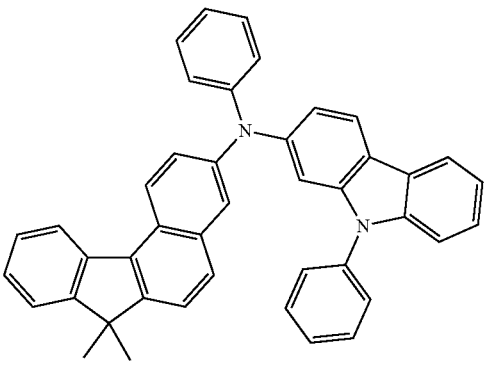
C-95

C-96
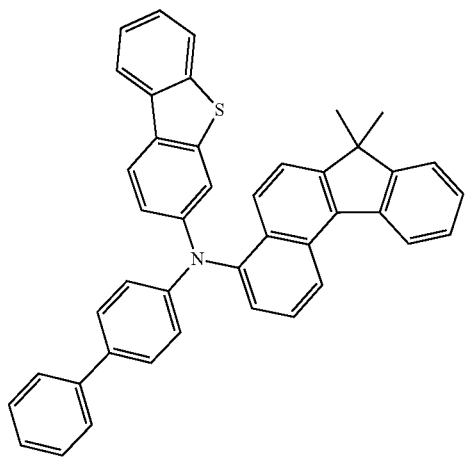
C-97
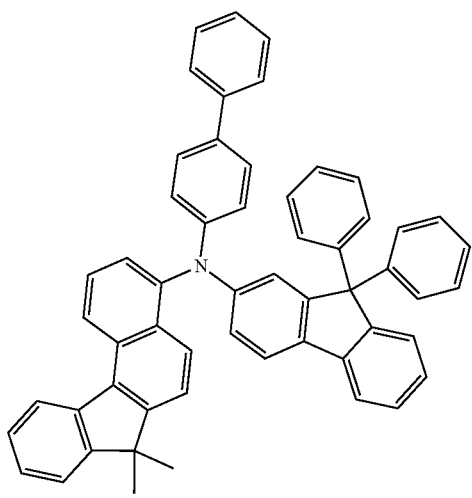
C-98
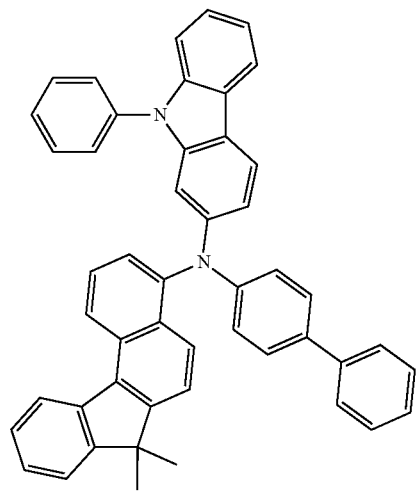
C-99
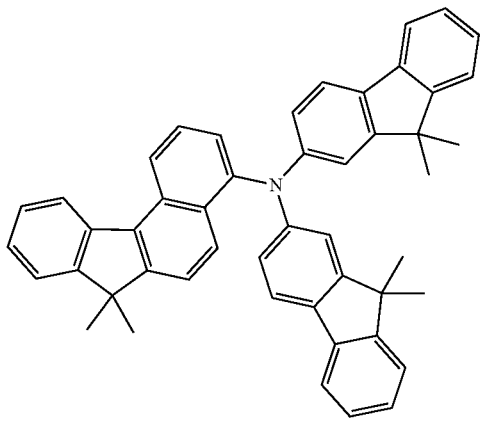
C-100
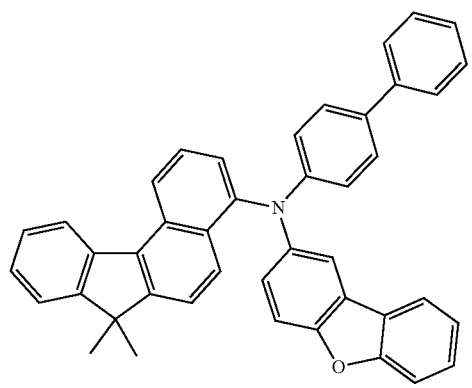
C-101
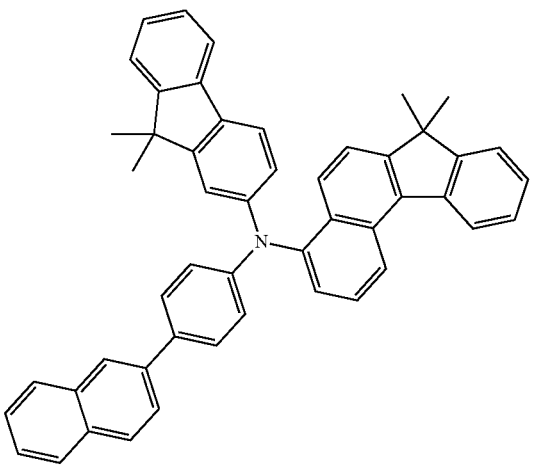

-continued
C-102
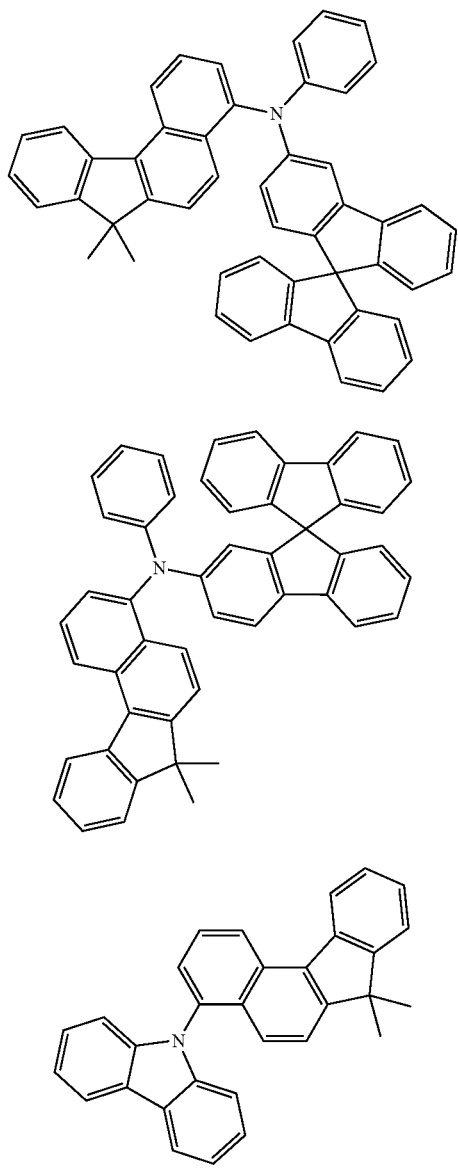
C-103
C-104
C-105
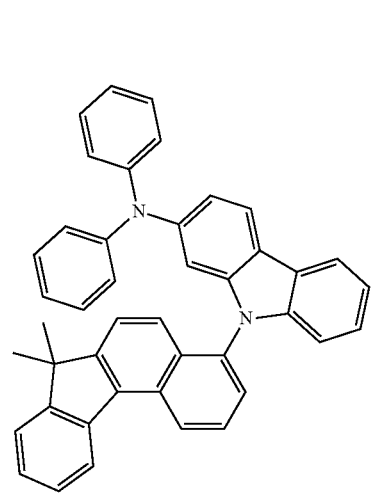
-continued
C-106
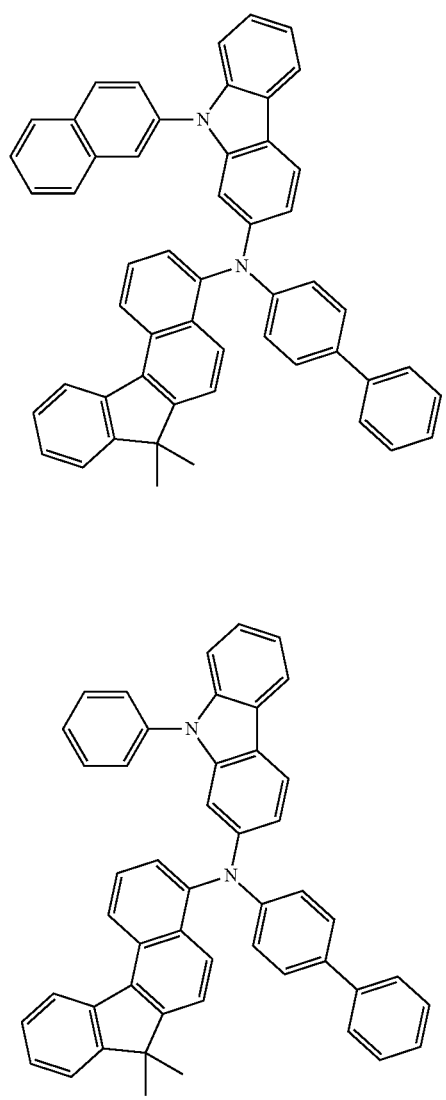
C-108
C-109
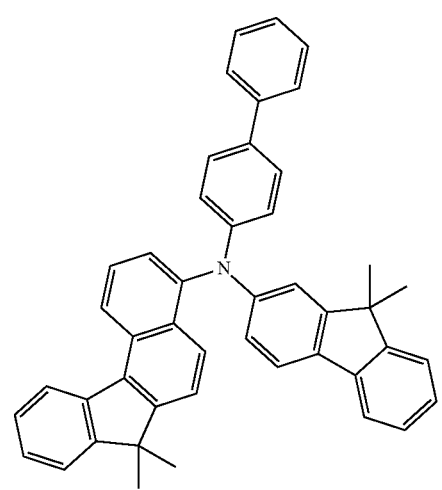

-continued
C-112
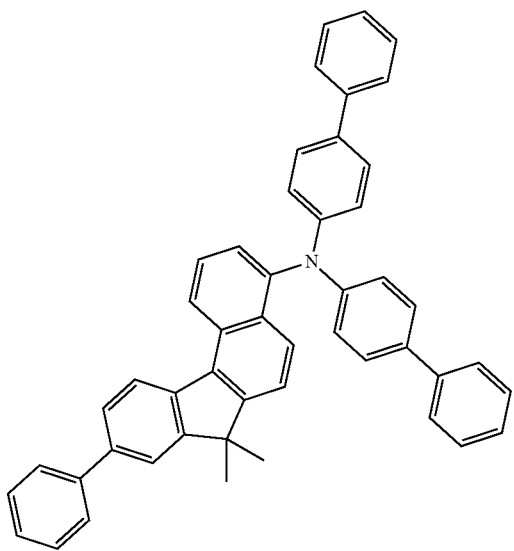
C-113
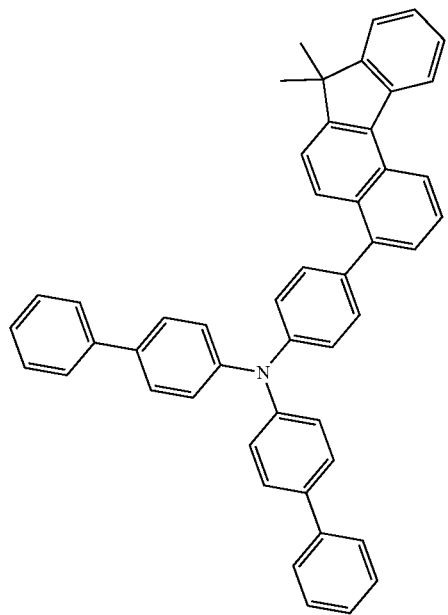
C-114
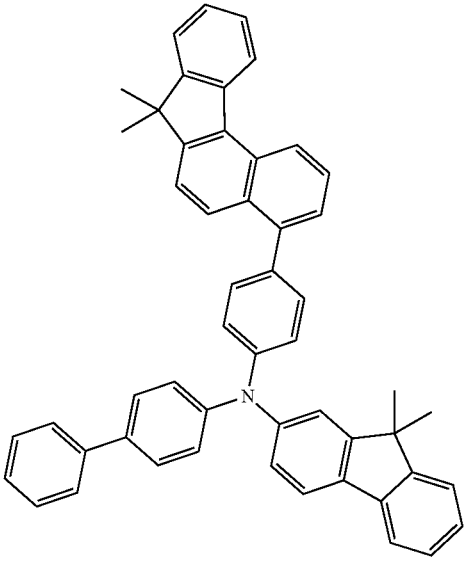
C-115
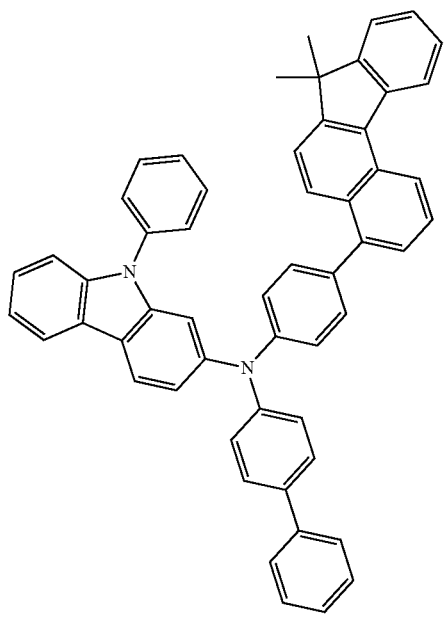
C-116
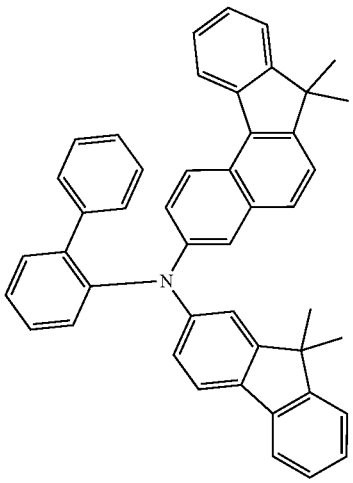

-continued

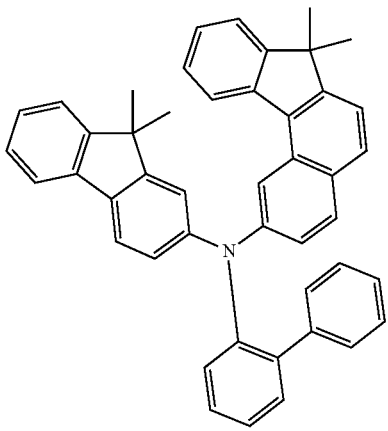
C-118 and

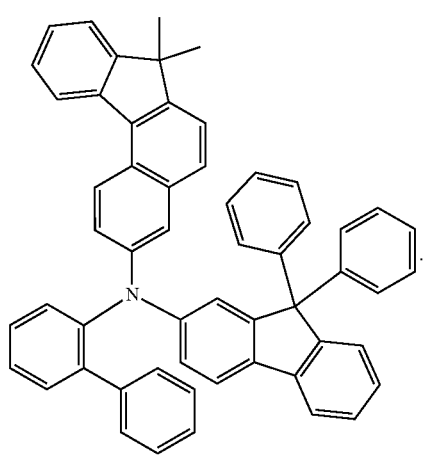
C-120

5. An organic electroluminescent material comprising the organic electroluminescent compound according to claim 1.

6. An organic electroluminescent device comprising the organic electroluminescent compound according to claim 1.

7. The organic electroluminescent device according to claim 6, wherein the organic electroluminescent compound is comprised in a hole transport zone.

8. The organic electroluminescent compound according to claim 1, wherein the substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino in $L_1$, and $R_1$ to $R_5$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered) heteroaryl unsubstituted or substituted with a (C6-C30)aryl(s); a (C6-C30)aryl unsubstituted or substituted with a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

9. The organic electroluminescent compound according to claim 1, wherein formula 1 is represented by any one of the following formulas 2 to 7:

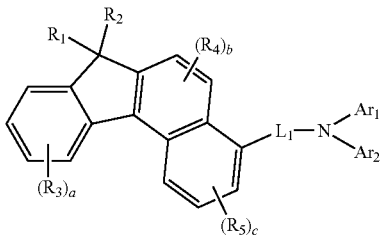
(2)

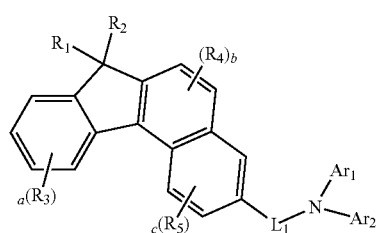
(3)

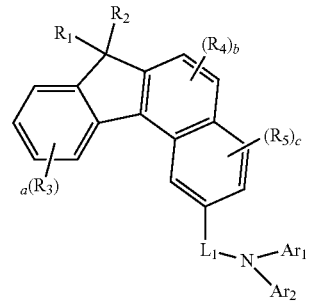
(4)

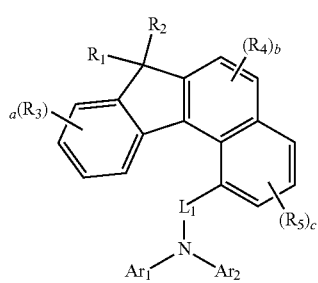
(5)

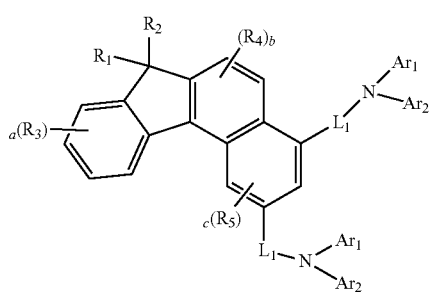
(6)

-continued
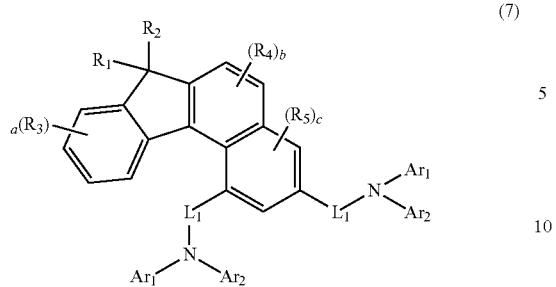
(7)
wherein
Ar$_1$, Ar$_2$, L$_1$, R$_1$ to R$_5$, and a to c are as defined in claim 4, and
in formulas 6 and 7, each of L$_1$, each of Ar$_1$, and each of Ar$_2$ may be the same or different.
* * * * *

UNITED STATES PATENT AND TRADEMARK OFFICE
CERTIFICATE OF CORRECTION

PATENT NO.         : 11,653,562 B2  
APPLICATION NO.    : 17/267469  
DATED              : May 16, 2023  
INVENTOR(S)        : Jin-Ri Hong Page 1 of 1

It is certified that error appears in the above-identified patent and that said Letters Patent is hereby corrected as shown below:

In the Claims

Column 153, Line 17, In Claim 9, Should read as follows:
- $Ar_1$, $Ar_2$, $L_1$, $R_1$ to $R_5$, and a to c are as defined in Claim 1 -

Signed and Sealed this  
Eighteenth Day of July, 2023

Katherine Kelly Vidal  
*Director of the United States Patent and Trademark Office*